US007795002B2

(12) United States Patent
Davidson et al.

(10) Patent No.: US 7,795,002 B2
(45) Date of Patent: *Sep. 14, 2010

(54) PRODUCTION OF GALACTOSYLATED GLYCOPROTEINS IN LOWER EUKARYOTES

(75) Inventors: Robert Davidson, Enfield, NH (US); Tillman Ulf Gerngross, Hanover, NH (US); Stefan Wildt, Lebanon, NH (US); Byung-Kwon Choi, Norwich, VT (US); Juergen Hermann Nett, Grantham, NH (US); Piotr Bobrowicz, White River Junction, VT (US); Stephen Robin Hamilton, Enfield, NH (US)

(73) Assignee: Glycofi, Inc., Lebanon, NH (US)

( * ) Notice: Subject to any disclaimer, the term of this patent is extended or adjusted under 35 U.S.C. 154(b) by 142 days.

This patent is subject to a terminal disclaimer.

(21) Appl. No.: 11/108,088

(22) Filed: Apr. 15, 2005

(65) Prior Publication Data

US 2006/0040353 A1 Feb. 23, 2006

Related U.S. Application Data

(63) Continuation-in-part of application No. 10/371,877, filed on Feb. 20, 2003, which is a continuation-in-part of application No. 09/892,591, filed on Jun. 27, 2001, now Pat. No. 7,029,872, application No. 11/108,088, which is a continuation-in-part of application No. PCT/US02/41510, filed on Dec. 24, 2002.

(60) Provisional application No. 60/562,424, filed on Apr. 15, 2004, provisional application No. 60/344,169, filed on Dec. 27, 2001, provisional application No. 60/279,997, filed on Mar. 30, 2001, provisional application No. 60/215,638, filed on Jun. 30, 2000, provisional application No. 60/214,358, filed on Jun. 28, 2000.

(51) Int. Cl.
*C12N 15/04* (2006.01)
*A61K 38/00* (2006.01)

(52) U.S. Cl. .................. 435/254.1; 435/254.2; 435/911

(58) Field of Classification Search ........................ None
See application file for complete search history.

(56) References Cited

U.S. PATENT DOCUMENTS

| | | | |
|---|---|---|---|
| 5,037,743 | A | 8/1991 | Welch et al. |
| 5,143,830 | A | 9/1992 | Holland et al. |
| 5,595,900 | A | 1/1997 | Lowe |
| 5,696,088 | A * | 12/1997 | Innis et al. ..................... 514/12 |
| 7,029,872 | B2 * | 4/2006 | Gerngross .................. 435/69.1 |
| 2006/0160179 | A1 | 7/2006 | Bobrowicz et al. |
| 2006/0211085 | A1 | 9/2006 | Bobrowicz |

FOREIGN PATENT DOCUMENTS

WO WO 02/00879 1/2002

WO WO 03/056914 7/2003

OTHER PUBLICATIONS

Chiba et al. (1998) "Production of human compatible high mannose-type (Man5GlcNAc2) sugar chains in *Saccharomyces cerevisiae*", J. Biol. Chem. vol. 273, No. 41, pp. 26298-26304.*
Takeuchi, M (1997) "Trial for Molecular Breeding of Yeast for the Production of Glycoprotein Therapeutics", Trends Glycosci. Glycotechnol., vol. 9, pp. S29-S35.*
Schwientek et al. (1998) "Cloning of a novel member of the UDP-galactose:beta-N-acetylglucosamine beta1,4-galactosyltransferase family, beta4Gal-T4, involved in glycosphingolipid biosynthesis", J. Biol. Chem., vol. 273, No. 45, pp. 29331-29340.*
Wildt et al. (2005) "The humanization of N-glycosylation pathways in yeast", Nat. Rev. Microbiol., vol. 3, No. 2, pp. 119-128.*
Orlean, P. (1990) "Dolichol phosphate mannose synthase is required in vivo for glycosyl phosphatidylinositol membrane anchoring, O mannosylation, and N glycosylation of protein in *Saccharomyces cerevisiae*", Mol. Cell. Biol., vol. 10, No. 11, pp. 5796-5805.*
Bobrowicz et al. (2004) Engineering of an artificial glycosylation pathway blocked in core oligosaccharide assembly in the yeast *Pichia pastoris*: production of complex humanized glycoproteins with terminal galactose, Glycobiology, vol. 14, No. 9, pp. 757-766.*
Fisher et al. (1999) Towards molecular farming in the future: *Pichia pastoris*-based production of single-chain antibody fragments, Biotechnol. Appl. Biochem., vol. 30, pp. 117-120.*
Malissard et al. (Jan. 2000) Expression of functional soluble forms of human β-1, 4-galactosyltransferase I, alpha-2,6-sialyltransferase, and alpha-1, 3-fucosyltransferase VI in the methylotrophic yeast *Pichia pastoris*, Biochem. Biophys. Res. Commun., vol. 267, No. 1, pp. 169-173.*
Ramasamy et al. (2005) Oligosaccharide Preferences of β1,4-Galactosyltransferase-I: Crystal Structures of Met340His Mutant of Human β1,4-Galactosyltransferase-I with a Pentasaccharide and Trisaccharides of the N-Glycan Moiety, J. Mol. Bol., vol. 353, pp. 53-67.*
Gerard et al. (1988) Prepro-alpha-factor has a cleavable signal sequence, J. Biol. Chem., vol. 263, No. 13, pp. 6209-6214.*
Davidson et al. (2004) Functional analysis of the ALG3 gene encoding the Dol-P-Man: Man5GlcNAc2-PP-Dol mannosyltransferase enzyme of *P. pastoris*, Glycobiol., vol. 14, No. 5, pp. 399-407.*
Wildt et al. (2005) The humanization of N-glycosylation pathways in yeast., Nat. Rev. Microbiol., vol. 3, pp. 119-127.*
Kawar et al. (Apr. 2000) N-Glycan processing by a lepidopteran insect 1,2-mannosidase, Glycobiol., vol. 10, No. 4, pp. 347-355.*
van Die et al. (1996) Glycosylation in lepidopteran insect cells: identification of a beta 1—>4-N-acetylgalactosaminyltransferase involved in the synthesis of complex-type oligosaccharide chains, Glycobiol., vol. 6, No. 2, pp. 157-164.*

(Continued)

*Primary Examiner*—Anand U Desai
*Assistant Examiner*—Samuel Liu

(57) ABSTRACT

The present invention provides a novel lower eukaryotic host cell producing human-like glycoproteins characterized as having a terminal β-galactose residue and essentially lacking fucose and sialic acid residues. The present invention also provides a method for catalyzing the transfer of a galactose residue from UDP-galactose onto an acceptor substrate in a recombinant lower eukaryotic host cell, which can be used as a therapeutic glycoprotein.

36 Claims, 17 Drawing Sheets

OTHER PUBLICATIONS

Jacobs et al. (2009) Engineering complex-type N-glycosylation in *Pichia pastoris* using GlycoSwitch technology, Nat. Protoc., vol. 4, No. 1, pp. 58-70.*

Velardo et al. (1993) The presence of UDP-N-acetylglucosamine:alpha-3-D-mannoside beta 1,2-N-acetylglucosaminyltransferase I activity in *Spodoptera frugiperda* cells (IPLB-SF-21AE) and its enhancement as a result of baculovirus infection, J. Biol. Chem., vol. 268, No. 24, pp. 17902-17907.*

Ren et al. (1997) Purification and properties of alpha-mannosidase II from Golgi-like membranes of baculovirus-infected *Spodoptera frugiperda* (IPLB-SF-21AE) cells, Biochem. J., vol. 324, Pt.3, pp. 951-956.*

Schwienetek et al. (1996) Golgi Localization and in Vivo Activity of a Mammalian Glycosyltransferase (Human 1,4-Galactosyltransferase) in Yeast, J. Biol. Chem., vol. 271, No. 7, pp. 3398-3405.*

Palacpac et al. (1999) Stable expression of human beta 1,4-galactosyltransferase in plant cells modifies N-linked glycosylation patterns, Proc. Natl. Acad. Sci. U S A., vol. 96, No. 8, pp. 4692-4697.*

Wu et al. (1996) The methylotrophic yeast *Pichia pastoris* synthesizes a functionally active chromophore precursor of the plant photoreceptor phytochrome, Proc. Natl. Acad. Sci. U S A., vol. 93, No. 17, pp. 8989-8994.*

Yang et al., Biotechnol. Bioeng., vol. 68 (2000), pp. 370-380, "Effects of ammonia on CHO cell growth, erythropoietin production, and glycosylation".

Stanley et al., Somatic Cell Genetics, vol. 3 (1977), pp. 391-405, "Complementation between mutants of CHO cells resistant to a variety of plant lectins".

Weikert et al., Nature Biotech., vol. 17 (1999), pp. 1116-1121, "Engineering Chinese hamster ovary cells to maximize sialic acid content of recombinant glycoproteins".

Umana et al., Nature Biotech., vol. 17 (1999), pp. 176-180, "Engineered glycoforms of an antineuroblastorna IgG1 withoptimized antibody-dependent cellular cytotoxic activity".

Umana et al., Biotech. Bioeng., vol. 65 (1999), pp. 542-549, "Tetracycline-regulated overexpression of glycosyltransferases in Chinese hamster ovary cells".

Stockert, Physiol. Rev., vol. 75 (1995), pp. 591-609, "The Asialoglycoprotein receptor: relationships between structure, function, and expression".

Thoden et al., J. Biol. Chem., vol. 276 (2001), pp. 15131-15136, "Human UDP-galactose 4-epimerase".

Svetina et al., J. of Biotech., vol. 76 (2000), pp. 245-251, "Expression of catalytic subunit of bovine enterokinase in the filamentous fungus *Aspergillus niger*".

Schwientek et al., J. Biol. Chem., vol. 271 (1996), pp. 3398-3405, "Golgi localization and in vivo activity of a mammalian glycosyltransferase . . . ".

Segawa et al., FEBS Letters, vol. 451 (1999), pp. 295-298, "*Schizosaccharomyces pombe* UDP-galactose transporter: identification of its functional form . . . ".

Harris et al., J. Biol. Chem., vol. 257 (1982), pp. 811-815, "Irreversible inhibition of bovine lung angiotensin I-converting enzyme with p-{N,N-Bis(chloroethyl)amino]phenylbutyric acid . . . ".

Romero et al., J. Biol. Chem., vol. 275 (2000), pp. 11071-11074, "Mutation of Arg273 to Leu alters the specificity of the yeast N-Glycan processing class I alpha1,2-mannosidase".

Malissard et al., Biochem. & Biophys. Res. Comm., vol. 287 (2000), pp. 169-173, "Expression of functional soluble forms of human beta-1,4-galactosyltranferase I, . . . ".

Majumdar et al., Eur. J. Biochem., vol. 271 (2004), pp. 753-759, "UDPgalactose 4-epimerase from *Saccharomyces cerevisiae*".

Lopez-Avalos et al., Glycobiology, vol. 11 (2001), pp. 413-422, The UDPase activity of the *Kluyveromyces lactis* Golgi GDPase has a role in uridine nucleotide sugar transport into Golgi vesicles.

Khatra et al., Eur. J. Biochem., vol. 44 (1974), pp. 537-560, "Some kinetic properties of human-milk galactosyl transferase".

Perez et al., Methods in Enzymology, vol. 138 (1987), pp. 709-715, "Transport of sugar nucleotides into the lumen of vesicles derived from rat liver rough endoplasmic . . . ".

Sommers et al., J. Cell Biol., vol. 91 (1981), pp. A406, Abstract 24001, "Transport of sugar nucleotides into rat liver Golgi".

Kainuma et al., Glycobiology, vol. 9 (1999), p. 133-141, "Coexpression of alpha 1,2-galactosyltransferase and UDP-galactose transporter efficiently galactosylates . . . ".

Huffaker et al., PNAS USA, vol. 80 (1983), pp. 7466-7470, "Yeast mutants deficient in protein glycosylation".

Abeijon et al., J. Cell Biol., vol. 122 (1993), pp. 307-323, "Guanosine diphosphatase is required for protein and Sphingolipid glycosylation in the Golgi lumen of *Saccharomyces cerevisiae*".

Fukuta et al., Arch. Biochem. & Biophys., vol. 392 (2001), pp. 79-86, "The widespread effect of beta1,4-galactosyltransferase on N-glycan processing".

Gao et al., J. Biol. Chem., vol. 274 (1999), pp. 21450-21456, "YND1, a homologue of GDA1, encodes membrane-bound apyrase rquired for Golgi . . . ".

Graham et al., J. Cell Biol., vol. 114 (1991), pp. 207-218, "Compartmental organization of Golgi-specific protein modification and vacuolar protein sorting events defined in a yeast sec18 (NSF) mutant".

Guillen et al., PNAS USA, vol. 95 (1998), pp. 7888-7892, "Mammalian Golgi apparatus UDP-N-acetylglucosamine transporter: molecular cloning by phenotype . . . ".

D'Alessio et al., J. Biol. Chem., vol. 278 (2003), pp. 22379-22387, "Nucleoside diphosphatase and glycosyltransferase activities can localize . . . ".

Beaudet et al., Methods in Enzymology, vol. 292 (1998), pp. 397-413, "High-level expression of mouse Mdr3 P-Glycoprotein in yeast *Pichia pastoris* . . . ".

Berninsone et al., J. Biol. Chem., vol. 270 (1995), pp. 14564-14567 (1995), "Regulation of yeast Golgi glycosylation".

Andersen et al., Curr. Opin. In Biotech., vol. 5 (1994), pp. 546-549, "The effect of cell-culture conditions on the oligosaccharide structures of secreted glycoproteins".

Berninsone et al., J. Biol. Chem., vol. 269 (1994), pp. 207-211, "The Golgi guanosine diphosphatase is required for transport of GDP-mannose into the lumen . . . ".

Aoki et al., J. Biochem., vol. 126 (1999), pp. 940-950, "Expression and activity of chimeric molecules between Human UDP-Galactose transporter . . . ".

Nett et al., Yeast, vol. 20 (2003), pp. 1279-1290, "Cloning and disruption of the PpURA5 gene and construction of a set of integration vectors for the stable genetic modification of *Pichia pastoris*".

Lin Cereghino et al., FEMS Microbiol. Rev., vol. 24 (2000), pp. 45-66, "Heterologous protein expression in the methyloptrophic yeast *Pichia pastoris*".

Hamilton et al., Science, vol. 301 (2003), pp. 1244-1246, "Production of complex human glycoproteins in yeast".

Choi et al., PNAS, vol. 100 (2003), pp. 5022-5027, "Use of combinatorial genetic libraries to humanize N-linked glycosylation in the yeast *Pichia pastoris*".

Goldstein et al., Yeast, vol. 15 (1999), pp. 1541-1553, "Three new dominant drug resistance cassettes for gene disruption in *Saccharomyces cerevisiae*".

Harkki et al., Bio/Technology, vol. 7 (1989), pp. 596-603, "A novel fungal expression system: secretion of active calf chymosin from the filamentous fungus *Trichoderma reesei*".

Genbank No. X55415, "Human mRNA for UDP_galactose:N-acetylglucosamine-(beta 1->4) galactosyltransferase", submitted Nov. 1, 1990.

Genbank No. AF016032, "*Homo sapiens* guanosine-diphosphatase like protein mRNA, complete cds", submitted Jul. 24, 1997.

Genbank No. AF038661 "*Homo sapiens* chromosome 1q21-1q23 beta-1,4-galactosyltransferase mRNA, complete cpds", submitted Dec. 16, 1997.

Genbank No. AF038660, "*Homo sapiens* chromosome 1p33-p34 beta-1,4-galactosyltransferase mRNA, complete cds", submitted Dec. 16, 1977.

Genbank No. BAA95614, "UDP-galactose transporter 2 [*Homo sapiens*]", submitted May 8, 2000.

Genbank No. BAA95615, "UDP-galactose transporter 1 [*Homo sapiens*]", submitted May 8, 2000.
Genbank No. NP 593447, Hypothetical protein SPAC824.08 [*Schizosaccaromyces pombe* 972h-], submitted Jun. 3, 2005.
Genbank No. AL022598, "*S. pombe* chromosme III cosmid c1795", submitted Apr. 22, 1998.
Genbank No. AH003575, Biochem. Biophys. Res. Comm., vol. 176 (1991), pp. 1269-1276, "Genomic structure and expression of human beta-1,4-galactosyltransferase".
Genbank No. CAC21576, "Guanosine diphosphatase [*Kluyveromyces lactis*]," submitted Jul. 11, 2000.
Genbank No. NP 010872, "Gdalp [*Saccharomyces cerevisiae*]", submitted Nov. 17, 1999.
Genbank No. NP 010920, "Apyrase with wide substrate specificity, involved in preventing the inhibition of glycosylation of hyrolyzing nucleoside tri- and diphosphates which are inhibitors of glycotransferases; . . . ", submitted Nov. 10, 1999.
Berka et al., Am. Chem. Soc., vol. 203 (1992), 203rd ACS National Meeting, San Francisco, CA, Abstract No. 121, "The filamentous fungus *Aspergillus niger* var. awamori as host for the expression . . . ".
Werner et al., Arzeimittelforschung, vol. 48 (1998), pp. 870-880, "Appropriate mammalian expression systems for biopharmaceuticals".

* cited by examiner

Figure 6A

SpGalE
amino acid sequence

MTGVHEGTVLVTGGAGYIGSHTCVVLLEKGYDVVIVDNLCNSRVEAVHRIEKLTGKKVIFHQVDLLDEPAL
DKVFANQNISAVIHFAGLKAVGESVQVPLSYYKNNISGTINLIECMKKYNVRDFVFSSSATVYGDPTRPGG
TIPIPESCPREGTSPYGRTKLFIENIIEDETKVNKSLNAALLRYFNPGGAHPSGELGEDPLGIPNNLLPYI
AQVAVGRLDHLNVFGDDYPTSDGTPIRDYIHVCDLAEAHVAALDYLRQHFVSCRPWNLGSGTGSTVFQVLN
AFSKAVGRDLPYKVTPRRAGDVVNLTANPTRANEELKWKTSRSIYEICVDTWRWQQKYPYGFDLTHTKTYK

Figure 6B

SpGalE
1068bp Coding sequence atgactggtgttcatgaagggactgtgttggttactggcggcgctggttatataggttctcatacgtgcgttgttttgtt
agaaaaaggatatgatgttgtaattgtcgataatttatgcaattctcgcgttgaagccgtgcaccgcattgaaaaactca
ctgggaaaaaagtcatattccaccaggtggatttgcttgatgagccagctttggacaaggtcttcgcaaatcaaaacata
tctgctgtcattcattttgctggtctcaaagcagttggtgaatctgtacaggttcctttgagttattacaaaaataacat
ttccggtaccattaatttaatagagtgcatgaagaagtataatgtacgtgacttcgtcttttcttcatctgctaccgtgt
atggcgatcctactagacctggtggtaccattcctattccagagtcatgccctcgtgaaggtacaagcccatatggtcgc
acaaagcttttcattgaaaatatcattgaggatgagaccaaggtgaacaaatcgcttaatgcagctttattacgctattt
taatcccggaggtgctcatccctctggtgaactcggtgaagatcctcttggcatccctaataacttgcttccttatatcg
cgcaagttgctgtaggaagattggatcatttgaatgtatttggcgacgattatcccacatctgacggtactccaattcgt
gactacattcacgtatgcgatttggcagaggctcatgttgctgctctcgattacctgcgccaacattttgttagttgccg
cccttggaatttgggatcaggaactggtagtactgttttttcaggtgctcaatgcgttttcgaaagctgttggaagagatc
ttccttataaggtcacccctagaagagcaggggacgttgttaacctaaccgccaaccccactcgcgctaacgaggagtta
aaatggaaaaccagtcgtagcatttatgaaatttgcgttgacacttggagatggcaacagaagtatccctatggctttga
cctgacccataccaagacatataagtaa

| | | |
|---|---|---|
| 1 | MTGVHEGT-----VLVTGGAGYIGSHTCVMLLEKGYDVVIV | SpGalEp |
| 1 | MAEK---------VLVTGGAGYIGSHTVLELLEAGYLPVVI | hGalEp |
| 1 | M--R---------VLVTGGSGYIGSHTCVQLLQNGHDVIIL | EcGalEp |
| 1 | MTAQLQSESTSKIVLVTGGAGYIGSHTVVELIENGYDCVVA | ScGal10p |
| 37 | DNLCNSRV------EAVHRIEKLTGKKVIFHQVDLLDEPAL | SpGalEp |
| 33 | DNFHNAFRGGGSLPESLRRVQELTGRSVEFEEMDILDQGAL | hGalEp |
| 31 | DNLCNSKRSV------LPVIERLGGKHPTFVEGDIRNEALM | EcGalEp |
| 42 | DNLSNSTY------DSVARLEVLTKHHIPFYEVDLCDRKGL | ScGal10p |
| 72 | DKVFANQNISAVIHFAGLKAVGESVQLVPLSYYKNNISGTIN | SpGalEp |
| 74 | QRLFNKYSEMAVIHFAGLKAVGESVQKPLDYYRVNLTGTIQ | hGalEp |
| 66 | TEILHDHAIDTVIHFAGLKAVGESVQKPLEYYDNNVNGTLR | EcGalEp |
| 77 | EKVFKEYKIDSVIHFAGLKAVGESTQTPLRYYHNNILGTVV | ScGal10p |
| 113 | LLECMKKYNVRDFVFSSSATVYGDPTRPGGTIPIPESCPRE | SpGalEp |
| 115 | LLEIMKAHGVKNLVFSSSATVYGNPQY----LPLDEAHPTG | hGalEp |
| 107 | LISAMRAANVKNFIFSSSATVYGDNPK----IPYVESIPTG | EcGalEp |
| 118 | LLELMQQYNVSKFVFSSSATVYGDATRFPNMIPIPEECPLG | ScGal10p |
| 154 | G-TSPYGRTKLFIENIIEDETKVNK-SLNAALLRYFNPGGA | SpGalEp |
| 152 | GCTNPYGKSKFFIEEMLRDLCQADK-TWNVVLLRYFNPTGA | hGalEp |
| 144 | TPQSPYGKSKLMVEQILTDLQKAQP-DWSIALLRYFNPVGA | EcGalEp |
| 159 | P-TNPYGRTKYAIENILNDLYNSDKSWKFATLRYFNPIGA | ScGal10p |
| 193 | HPSGELGEDPLGIPNNLLPYIAQVAVGRLDHLNVFGDDYPT | SpGalEp |
| 192 | HASGCIGEDPGIPNNLMPYVSQVATGRREALNVFGNDYDT | hGalEp |
| 184 | HPSGDMGEDPQGIPNNLMPYIAQVAVGRRDSLAIFGNDYPT | EcGalEp |
| 199 | HPSGLIGEDPLGIPNNLLPYMAQVAVGRREKLYIFGDDYDS | ScGal10p |
| 234 | SDGTPIRDYIHVCDLAEAHVAALDYL---RQHFVSCRPWNL | SpGalEp |
| 233 | EDGTGVRDYIHVVDLAKGHTAAIRKL----KEQCGCRIYNL | hGalEp |
| 225 | EDGTGVRDYIHVMDLADGHVVAMEKL----ANKPGVHIYNL | EcGalEp |
| 240 | RDGTPIRDYIHVVDLAKGHTAALQYLEAYNENEGLCREWNL | ScGal10p |
| 272 | GSGTGSTVEQVLNAFSKAVGRDLPYKVTPRRAGDVVNLTAN | SpGalEp |
| 270 | GTGTGYSVLQMVQAMEKASGKKIPYKVVARREGDVAACYAN | hGalEp |
| 262 | GAGVGNSVLDVVNAFSKACGKPVNYHFAPRREGDLPAYWAD | EcGalEp |
| 281 | GSGKGSTVFEVYHAFCKASGIDLPYKVTGRRAGDVLNLTAK | ScGal10p |
| 313 | PTRANEELKWKTSRSIYEICVDTWRWQQKYPYGFDLTHTKT | SpGalEp |
| 311 | PSLAQEELGWTAALGLDRMCEDLWRWQKNPSGFGTQA | hGalEp |
| 303 | ASKADRELNWRVTRTLDEMAQDTWHWQSRHPQGY--PD | EcGalEp |
| 322 | PDRAKRELKWQTELQVEDSCKDLKWTTENPFGYQLRGVEA | ScGal10p |

Fig. 7

```
                        SEQUENCE LISTING

<160> NUMBER OF SEQ ID NOS: 71

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gccgcgacct gagccgcctg ccccaac                                          27

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctagctcggt gtcccgatgt ccactgt                                          27

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 3
cttaggcgcg ccggccgcga cctgagccgc ctgccc                                36

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggggcatatc tgccgcccat c                                                21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gatgggcggc agatatgccc c                                                21

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cttcttaatt aactagctcg gtgtcccgat gtccac                                36

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccttgcggcc gcatggctgt caagggcgac gatgtcaaa                             39

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
attcgagaat agttaagtgt caaaatcaat gcactatttt                            40

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
```
aaaatagtgc attgattttg acacttaact attctcgaat                             40

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10 cctttaatt aattaatgct tatgatcaac gtccttagc                               39

<210> SEQ ID NO 11
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggctcgagcg gccgccacca tgaatagcat acacatgaac gccaatacg                   49

<210> SEQ ID NO 12
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccctcgagtt aattaactag acgcgcggca gcagcttctc ctcatcg                     47

<210> SEQ ID NO 13
<211> LENGTH: 355
<212> TYPE: PRT
<213> ORGANISM: Schizosaccharomyces pombe

<400> SEQUENCE: 13

Met Thr Gly Val His Glu Gly Thr Val Leu Val Thr Gly Ala Gly
  1               5                  10                  15

Tyr Ile Gly Ser His Thr Cys Val Val Leu Glu Lys Gly Tyr Asp
                 20                  25                  30

Val Val Ile Val Asp Asn Leu Cys Asn Ser Arg Val Glu Ala Val His
             35                  40                  45

Arg Ile Glu Lys Leu Thr Gly Lys Lys Val Ile Phe His Gln Val Asp
         50                  55                  60

Leu Leu Asp Glu Pro Ala Leu Asp Lys Val Phe Ala Asn Gln Asn Ile
 65                  70                  75                  80

Ser Ala Val Ile His Phe Ala Gly Leu Lys Ala Val Gly Glu Ser Val
                 85                  90                  95

Gln Val Pro Leu Ser Tyr Tyr Lys Asn Asn Ile Ser Gly Thr Ile Asn
                100                 105                 110

Leu Ile Glu Cys Met Lys Lys Tyr Asn Val Arg Asp Phe Val Phe Ser
            115                 120                 125

Ser Ser Ala Thr Val Tyr Gly Asp Pro Thr Arg Pro Gly Gly Thr Ile
        130                 135                 140

Pro Ile Pro Glu Ser Cys Pro Arg Glu Gly Thr Ser Pro Tyr Gly Arg
145                 150                 155                 160

```
Thr Lys Leu Phe Ile Glu Asn Ile Ile Glu Asp Glu Thr Lys Val Asn
                165                 170                 175
Lys Ser Leu Asn Ala Ala Leu Leu Arg Tyr Phe Asn Pro Gly Gly Ala
            180                 185                 190
His Pro Ser Gly Glu Leu Gly Glu Asp Pro Leu Gly Ile Pro Asn Asn
        195                 200                 205
Leu Leu Pro Tyr Ile Ala Gln Val Ala Val Gly Arg Leu Asp His Leu
    210                 215                 220
Asn Val Phe Gly Asp Asp Tyr Pro Thr Ser Asp Gly Thr Pro Ile Arg
225                 230                 235                 240
Asp Tyr Ile His Val Cys Asp Leu Ala Glu Ala His Val Ala Ala Leu
                245                 250                 255
Asp Tyr Leu Arg Gln His Phe Val Ser Cys Arg Pro Trp Asn Leu Gly
            260                 265                 270
Ser Gly Thr Gly Ser Thr Val Phe Gln Val Leu Asn Ala Phe Ser Lys
        275                 280                 285
Ala Val Gly Arg Asp Leu Pro Tyr Lys Val Thr Pro Arg Arg Ala Gly
    290                 295                 300
Asp Val Val Asn Leu Thr Ala Asn Pro Thr Arg Ala Asn Glu Glu Leu
305                 310                 315                 320
Lys Trp Lys Thr Ser Arg Ser Ile Tyr Glu Ile Cys Val Asp Thr Trp
                325                 330                 335
Arg Trp Gln Gln Lys Tyr Pro Tyr Gly Phe Asp Leu Thr His Thr Lys
            340                 345                 350
Thr Tyr Lys
        355

<210> SEQ ID NO 14
<211> LENGTH: 1068
<212> TYPE: DNA
<213> ORGANISM: Schizosaccharomyces pombe

<400> SEQUENCE: 14
atgactggtg ttcatgaagg gactgtgttg gttactggcg gcgctggtta tataggttct      60
catacgtgcg ttgttttgtt agaaaaagga tatgatgttg taattgtcga taatttatgc     120
aattctcgcg ttgaagccgt gcaccgcatt gaaaaactca ctgggaaaaa agtcatattc     180
caccaggtgg atttgcttga tgagccagct ttggacaagg tcttcgcaaa tcaaaacata     240
tctgctgtca ttcattttgc tggtctcaaa gcagttggtg aatctgtaca ggttcctttg     300
agttattaca aaaataacat ttccggtacc attaatttaa tagagtgcat gaagaagtat     360
aatgtacgtg acttcgtctt ttcttcatct gctaccgtgt atggcgatcc tactagacct     420
ggtggtacca ttcctattcc agagtcatgc cctcgtgaag gtacaagccc atatggtcgc     480
acaaagcttt tcattgaaaa tatcattgag atgagaccaa ggtgaacaa atcgcttaat      540 gcagctttat tacgctattt taatcccgga ggtgctcatc cctctggtga actcggtgaa     600
gatcctcttg gcatccctaa taacttgctt ccttatatcg cgcaagttgc tgtaggaaga     660
ttggatcatt tgaatgtatt tggcgacgat tatcccacat ctgacggtac tccaattcgt     720
gactacattc acgtatgcga tttggcagag gctcatgttg ctgctctcga ttacctgcgc     780
caacattttg ttagttgccg cccttggaat ttgggatcag gaactggtag tactgttttt     840
caggtgctca atgcgttttc gaagctgttg gaagagatc ttcctttataa ggtcaccccct    900 agaagagcag gggacgttgt taacctaacc gccaacccca ctcgcgctaa cgaggagtta     960
```

```
aaatggaaaa ccagtcgtag catttatgaa atttgcgttg acacttggag atggcaacag    1020
aagtatccct atggctttga cctgacccat accaagacat ataagtaa                1068
```

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

```
tatgcggccg cggctgatga tatttgctac ga                                  32
```

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

```
cctctcgagt ggacacagga gactcagaaa cag                                 33
```

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

```
cttctcgagg aagtaaagtt ggcgaaactt                                     30
```

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18

```
cttagcggcc gcgattgttc gtttgagtag ttt                                 33
```

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

```
cttctcgagg gcattcaaag aagccttggg                                     30
```

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cttagcggcc gctgagtggt catgtgggaa ctt                        33

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cctggatcca acagactaca atgacaggag                            30

<210> SEQ ID NO 22
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cctgcatgcc tcgagcttgc cggcgtctaa atagccgttg aag             43

<210> SEQ ID NO 23
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cctgtcgacg ctgccggcaa gctcgagttt aagcggtgct gc              42

<210> SEQ ID NO 24
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cctggatcct ttggcaaaaa ccagccctgg tgag                       34

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tccttaatta agaaaagcta gagtaaaata gat                        33

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tccctcgagg atcatgttga tcaactgaga ccg                                    33

<210> SEQ ID NO 27
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggctcgagcg gccgccacca tggcagcggt tggggctggt ggttc                       45

<210> SEQ ID NO 28
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ccctcgagtt aattaatcac ttcaccagca ctgactttgg cag                         43

<210> SEQ ID NO 29
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggctcgagcg gccgccacca tggcagcggt tggggctggt ggttc                       45

<210> SEQ ID NO 30
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ccctcgagtt aattaactag gaacccttca ccttggtgag caac                        44

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tagcggccgc atgacagctc agttacaaag tgaaag                                 36

<210> SEQ ID NO 32
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

```
cgttaattaa tcaggaaaat ctgtagacaa tcttgg                                      36

<210> SEQ ID NO 33
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gcggccgcat ggcagagaag gtgctggta                                              29

<210> SEQ ID NO 34
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ttaattaatc aggcttgcgt gccaaagcc                                              29

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
atgactggtg ttcatgaagg g                                                     21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ttacttatat gtcttggtat g                                                     21

<210> SEQ ID NO 37
<211> LENGTH: 94
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gcggccgcat gactggtgtt catgaaggga ctgtgttggt tactggcggc gctggttata           60
taggttctca tacgtgcgtt gttttgttag aaaa                                       94

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
```
ttaattaatt acttatatgt cttggtatg                                29

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cttaggcgcg cccagcacct ggccttcttc agc                            33

<210> SEQ ID NO 40
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cttgttaatt aatcagcccc gaggggccca cgacgg                         36

<210> SEQ ID NO 41
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cttaggcgcg cccgaagtct cagtgcccta tttggc                         36

<210> SEQ ID NO 42
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cttgttaatt aatcagtgtg aacctcggag ggctgt                         36

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tacgagattc ccaaatatga ttcc                                      24

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
atagtgtctc catatggctt gttc                                                    24

<210> SEQ ID NO 45
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
cttggcgcgc catgactggt gttcatgaag ggact                                        35

<210> SEQ ID NO 46
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cctggatccc ttatatgtct tggtatgggt cag                                          33

<210> SEQ ID NO 47
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cttggatccg gtggtggccg cgacctgagc cgcctgccc                                    39

<210> SEQ ID NO 48
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cttcttaatt aactagctcg gtgtcccgat gtccac                                       36

<210> SEQ ID NO 49
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)
<223> OTHER INFORMATION: Thr or Val
<220> FEATURE:
<221> NAME/KEY: MOD_RES
<222> LOCATION: (16)
<223> OTHER INFORMATION: Val, Lys or Ile
<220> FEATURE:
<221> NAME/KEY: MOD_RES
<222> LOCATION: (19)
<223> OTHER INFORMATION: Ser, Asp, Glu or Arg

<400> SEQUENCE: 49

Val Ile His Phe Ala Gly Leu Lys Ala Val Gly Glu Ser Xaa Gln Xaa
1               5                   10                  15

```
Pro Leu Xaa Tyr Tyr
            20
```

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)
<223> OTHER INFORMATION: Asp or Asn

<400> SEQUENCE: 50

```
Phe Ser Ser Ser Ala Thr Val Tyr Gly Xaa
 1               5                  10
```

<210> SEQ ID NO 51
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Gly, Thr, Val or Ile
<220> FEATURE:
<221> NAME/KEY: MOD_RES
<222> LOCATION: (11)
<223> OTHER INFORMATION: Pro or Ala
<220> FEATURE:
<221> NAME/KEY: MOD_RES
<222> LOCATION: (14)
<223> OTHER INFORMATION: Glu, Cys, Asp or Leu
<220> FEATURE:
<221> NAME/KEY: MOD_RES
<222> LOCATION: (15)
<223> OTHER INFORMATION: Leu, Ile or Met
<220> FEATURE:
<221> NAME/KEY: MOD_RES
<222> LOCATION: (20)
<223> OTHER INFORMATION: Leu or Gln
<220> FEATURE:
<221> NAME/KEY: MOD_RES
<222> LOCATION: (27)
<223> OTHER INFORMATION: Leu or Met
<220> FEATURE:
<221> NAME/KEY: MOD_RES
<222> LOCATION: (30)
<223> OTHER INFORMATION: Ile, Val or Met
<220> FEATURE:
<221> NAME/KEY: MOD_RES
<222> LOCATION: (31)
<223> OTHER INFORMATION: Ala or Ser
<220> FEATURE:
<221> NAME/KEY: MOD_RES
<222> LOCATION: (35)
<223> OTHER INFORMATION: Val or Ile
<220> FEATURE:
<221> NAME/KEY: MOD_RES
<222> LOCATION: (38)
<223> OTHER INFORMATION: Leu or Arg

<400> SEQUENCE: 51

```
Leu Arg Tyr Phe Asn Pro Xaa Gly Ala His Xaa Ser Gly Xaa Xaa Gly
 1               5                  10                  15

Glu Asp Pro Xaa Gly Ile Pro Asn Asn Leu Xaa Pro Tyr Xaa Xaa Gln
            20                  25                  30
```

Val Ala Xaa Gly Arg Xaa
            35

<210> SEQ ID NO 52
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Asn, Ala or Tyr
<220> FEATURE:
<221> NAME/KEY: MOD_RES
<222> LOCATION: (3)
<223> OTHER INFORMATION: Val or Ile
<220> FEATURE:
<221> NAME/KEY: MOD_RES
<222> LOCATION: (6)
<223> OTHER INFORMATION: Asp or Asn
<220> FEATURE:
<221> NAME/KEY: MOD_RES
<222> LOCATION: (9)
<223> OTHER INFORMATION: Pro or Asp
<220> FEATURE:
<221> NAME/KEY: MOD_RES
<222> LOCATION: (10)
<223> OTHER INFORMATION: Thr or Ser
<220> FEATURE:
<221> NAME/KEY: MOD_RES
<222> LOCATION: (11)
<223> OTHER INFORMATION: Ser, Glu or Arg
<220> FEATURE:
<221> NAME/KEY: MOD_RES
<222> LOCATION: (15)
<223> OTHER INFORMATION: Pro or Gly
<220> FEATURE:
<221> NAME/KEY: MOD_RES
<222> LOCATION: (16)
<223> OTHER INFORMATION: Ile or Val
<220> FEATURE:
<221> NAME/KEY: MOD_RES
<222> LOCATION: (23)
<223> OTHER INFORMATION: Cys, Val or Met
<220> FEATURE:
<221> NAME/KEY: MOD_RES
<222> LOCATION: (27)
<223> OTHER INFORMATION: Glu, Lys or Asp
<220> FEATURE:
<221> NAME/KEY: MOD_RES
<222> LOCATION: (28)
<223> OTHER INFORMATION: Ala or Gly
<220> FEATURE:
<221> NAME/KEY: MOD_RES
<222> LOCATION: (30)
<223> OTHER INFORMATION: Val or Ile
<220> FEATURE:
<221> NAME/KEY: MOD_RES
<222> LOCATION: (31)
<223> OTHER INFORMATION: Ala or Val
<220> FEATURE:
<221> NAME/KEY: MOD_RES
<222> LOCATION: (33)
<223> OTHER INFORMATION: Leu or Met

<400> SEQUENCE: 52

Leu Xaa Xaa Phe Gly Xaa Asp Tyr Xaa Xaa Xaa Asp Gly Thr Xaa Xaa
 1               5                  10                  15

Arg Asp Tyr Ile His Val Xaa Asp Leu Ala Xaa Xaa His Xaa Xaa Ala
                20                  25                  30

Xaa

```
<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: Ser or Ala

<400> SEQUENCE: 53

Val Leu Val Thr Gly Gly Xaa Gly Tyr Ile Gly Ser His Thr
 1               5                  10

<210> SEQ ID NO 54
<211> LENGTH: 1303
<212> TYPE: DNA
<213> ORGANISM: Schizosaccharomyces pombe

<400> SEQUENCE: 54
atggtatgaa taactttttt aattaatcaa aagcattctt ttgtatgaaa atactaatta      60
tgattcatag actggtgttc atgaagggac tgtgttggtt actggcggcg ctggttatat     120
aggttctcat acggtacgta gagagcttga agatacagaa gaggattagt aatgtacatg     180
taaatgtttt aagcacgcat cttttgtgaa tatagcttgc tgctctttac ttttatacaa     240
tttcgtccat attctataaa gctcttcttt gagatatttt gctaaccaca atctgcaata     300
gtgcgttgtt ttgttagaaa aaggatatga tgttgtaatt gtcgataatt tatgcaattc     360
tcgcgttgaa gccgtgcacc gcattgaaaa actcactggg aaaaaagtca tattccacca     420
ggtggatttg cttgatgagc cagctttgga caaggtcttc gcaaatcaaa acatatctgc     480
tgtcattcat tttgctggtc tcaaagcagt tggtgaatct gtacaggttc ctttgagtta     540
ttacaaaaat aacatttccg gtaccattaa tttaatagag tgcatgaaga agtataatgt     600
acgtgacttc gtcttttctt catctgctac cgtgtatggc gatcctacta gacctggtgg     660
taccattcct attccagagt catgccctcg tgaaggtaca agcccatatg gtcgcacaaa     720
gcttttcatt gaaaatatca ttgaggatga gaccaaggtg aacaaatcgc ttaatgcagc     780
tttattacgc tattttaatc ccggaggtgc tcatccctct ggtgaactcg gtgaagatcc     840
tcttggcatc cctaataact tgcttcctta tatcgcgcaa gttgctgtag aagattgga     900 tcatttgaat gtatttggcg acgattatcc cacatctgac ggtactccaa ttcgtgacta     960
cattcacgta tgcgatttgg cagaggctca tgttgctgct ctcgattacc tgcgccaaca    1020
ttttgttagt tgccgccctt ggaatttggg atcaggaact ggtagtactg ttttttcaggt    1080 gctcaatgcg tttttcgaaag ctgttggaag agatcttcct tataaggtca ccctagaag    1140 agcaggggac gttgttaacc taaccgccaa ccccactcgc gctaacgagg agttaaaatg    1200
gaaaaccagt cgtagcattt atgaaatttg cgttgacact tggagatggc aacagaagta    1260
tccctatggc tttgacctga cccataccaa gacatataag taa                      1303

<210> SEQ ID NO 55
<211> LENGTH: 355
<212> TYPE: PRT
<213> ORGANISM: Homo sapiens

<400> SEQUENCE: 55

Gly Arg Asp Leu Ser Arg Leu Pro Gln Leu Val Gly Val Ser Thr Pro
 1               5                  10                  15
```

Leu Gln Gly Gly Ser Asn Ser Ala Ala Ala Ile Gly Gln Ser Ser Gly
                20                  25                  30

Glu Leu Arg Thr Gly Gly Ala Arg Pro Pro Pro Leu Gly Ala Ser
         35                  40                  45

Ser Gln Pro Arg Pro Gly Gly Asp Ser Ser Pro Val Val Asp Ser Gly
         50                  55                  60

Pro Gly Pro Ala Ser Asn Leu Thr Ser Val Pro Val Pro His Thr Thr
 65                  70                  75                  80

Ala Leu Ser Leu Pro Ala Cys Pro Glu Glu Ser Pro Leu Leu Val Gly
                 85                  90                  95

Pro Met Leu Ile Glu Phe Asn Met Pro Val Asp Leu Glu Leu Val Ala
                100                 105                 110

Lys Gln Asn Pro Asn Val Lys Met Gly Gly Arg Tyr Ala Pro Arg Asp
            115                 120                 125

Cys Val Ser Pro His Lys Val Ala Ile Ile Pro Phe Arg Asn Arg
        130                 135                 140

Gln Glu His Leu Lys Tyr Trp Leu Tyr Tyr Leu His Pro Val Leu Gln
145                 150                 155                 160

Arg Gln Gln Leu Asp Tyr Gly Ile Tyr Val Ile Asn Gln Ala Gly Asp
                165                 170                 175

Thr Ile Phe Asn Arg Ala Lys Leu Leu Asn Val Gly Phe Gln Glu Ala
            180                 185                 190

Leu Lys Asp Tyr Asp Tyr Thr Cys Phe Val Phe Ser Asp Val Asp Leu
            195                 200                 205

Ile Pro Met Asn Asp His Asn Ala Tyr Arg Cys Phe Ser Gln Pro Arg
        210                 215                 220

His Ile Ser Val Ala Met Asp Lys Phe Gly Phe Ser Leu Pro Tyr Val
225                 230                 235                 240

Gln Tyr Phe Gly Gly Val Ser Ala Leu Ser Lys Gln Gln Phe Leu Thr
                245                 250                 255

Ile Asn Gly Phe Pro Asn Asn Tyr Trp Gly Trp Gly Gly Glu Asp Asp
            260                 265                 270

Asp Ile Phe Asn Arg Leu Val Phe Arg Gly Met Ser Ile Ser Arg Pro
        275                 280                 285

Asn Ala Val Val Gly Arg Cys Arg Met Ile Arg His Ser Arg Asp Lys
    290                 295                 300

Lys Asn Glu Pro Asn Pro Gln Arg Phe Asp Arg Ile Ala His Thr Lys
305                 310                 315                 320

Glu Thr Met Leu Ser Asp Gly Leu Asn Ser Leu Thr Tyr Gln Val Leu
                325                 330                 335

Asp Val Gln Arg Tyr Pro Leu Tyr Thr Gln Ile Thr Val Asp Ile Gly
            340                 345                 350

Thr Pro Ser
        355

<210> SEQ ID NO 56
<211> LENGTH: 337
<212> TYPE: PRT
<213> ORGANISM: Homo sapiens

<400> SEQUENCE: 56

Ala Gln His Leu Ala Phe Phe Ser Arg Phe Ser Ala Arg Gly Pro Ala
 1               5                  10                  15

His Ala Leu His Pro Ala Ala Ser Ser Ser Ser Ser Ser Ser Asn Cys

```
                20                  25                  30
Ser Arg Pro Asn Ala Thr Ala Ser Ser Gly Leu Pro Glu Val Pro
             35                  40                  45

Ser Ala Leu Pro Gly Pro Thr Ala Pro Thr Leu Pro Pro Cys Pro Asp
 50                  55                  60

Ser Pro Pro Gly Leu Val Gly Arg Leu Leu Ile Glu Phe Thr Ser Pro
 65                  70                  75                  80

Met Pro Leu Glu Arg Val Gln Arg Glu Asn Pro Gly Val Leu Met Gly
                 85                  90                  95

Gly Arg Tyr Thr Pro Pro Asp Cys Thr Pro Ala Gln Thr Val Ala Val
                100                 105                 110

Ile Ile Pro Phe Arg His Arg Glu His His Leu Arg Tyr Trp Leu His
            115                 120                 125

Tyr Leu His Pro Ile Leu Arg Arg Gln Arg Leu Arg Tyr Gly Val Tyr
       130                 135                 140

Val Ile Asn Gln His Gly Glu Asp Thr Phe Asn Arg Ala Lys Leu Leu
145                 150                 155                 160

Asn Val Gly Phe Leu Glu Ala Leu Lys Glu Asp Ala Ala Tyr Asp Cys
                165                 170                 175

Phe Ile Phe Ser Asp Val Asp Leu Val Pro Met Asp Asp Arg Asn Leu
            180                 185                 190

Tyr Arg Cys Gly Asp Gln Pro Arg His Phe Ala Ile Ala Met Asp Lys
        195                 200                 205

Phe Gly Phe Arg Leu Pro Tyr Ala Gly Tyr Phe Gly Gly Val Ser Gly
    210                 215                 220

Leu Ser Lys Ala Gln Phe Leu Arg Ile Asn Gly Phe Pro Asn Glu Tyr
225                 230                 235                 240

Trp Gly Trp Gly Gly Glu Asp Asp Asp Ile Phe Asn Arg Ile Ser Leu
                245                 250                 255

Thr Gly Met Lys Ile Ser Arg Pro Asp Ile Arg Ile Gly Arg Tyr Arg
            260                 265                 270

Met Ile Lys His Asp Arg Asp Lys His Asn Glu Pro Asn Pro Gln Arg
        275                 280                 285

Phe Thr Lys Ile Gln Asn Thr Lys Leu Thr Met Lys Arg Asp Gly Ile
    290                 295                 300

Gly Ser Val Arg Tyr Gln Val Leu Glu Val Ser Arg Gln Pro Leu Phe
305                 310                 315                 320

Thr Asn Ile Thr Val Asp Ile Gly Arg Pro Pro Ser Trp Pro Pro Arg
                325                 330                 335

Gly

<210> SEQ ID NO 57
<211> LENGTH: 362
<212> TYPE: PRT
<213> ORGANISM: Homo sapiens

<400> SEQUENCE: 57

Arg Ser Leu Ser Ala Leu Phe Gly Arg Asp Gln Gly Pro Thr Phe Asp
  1               5                  10                  15

Tyr Ser His Pro Arg Asp Val Tyr Ser Asn Leu Ser His Leu Pro Gly
                 20                  25                  30

Arg Pro Gly Gly Pro Ala Pro Gln Gly Leu Pro Tyr Cys Pro Glu
             35                  40                  45

Arg Ser Pro Leu Leu Val Gly Pro Val Ser Val Ser Phe Ser Pro Val
```

```
            50                  55                  60
Pro Ser Leu Ala Glu Ile Val Glu Arg Asn Pro Arg Val Glu Pro Gly
 65                  70                  75                  80

Ala Arg Tyr Arg Pro Ala Gly Cys Glu Pro Arg Ser Arg Thr Ala Ile
                 85                  90                  95

Ile Val Pro His Arg Ala Arg Glu His His Leu Arg Leu Leu Leu Tyr
            100                 105                 110

His Leu His Pro Phe Leu Gln Arg Gln Gln Leu Ala Tyr Gly Ile Tyr
        115                 120                 125

Val Ile His Gln Ala Gly Asn Gly Thr Phe Asn Arg Ala Lys Leu Leu
130                 135                 140

Asn Val Gly Val Arg Glu Ala Leu Arg Asp Glu Glu Trp Asp Cys Leu
145                 150                 155                 160

Phe Leu His Asp Val Asp Leu Leu Pro Glu Asn Asp His Asn Leu Tyr
                165                 170                 175

Val Cys Asp Pro Arg Gly Pro Arg His Val Ala Val Ala Met Asn Ser
            180                 185                 190

Phe Gly Tyr Ser Leu Pro Tyr Pro Gln Tyr Phe Gly Gly Val Ser Ala
        195                 200                 205

Leu Thr Pro Asp Gln Tyr Leu Lys Met Asn Gly Phe Pro Asn Glu Tyr
210                 215                 220

Trp Gly Trp Gly Gly Glu Asp Asp Asp Ile Ala Thr Arg Val Arg Leu
225                 230                 235                 240

Ala Gly Met Lys Ile Ser Arg Pro Pro Thr Ser Val Gly His Tyr Lys
                245                 250                 255

Met Val Lys His Arg Gly Asp Lys Gly Asn Glu Glu Asn Pro His Arg
            260                 265                 270

Phe Asp Leu Leu Val Arg Thr Gln Asn Ser Trp Thr Gln Asp Gly Met
        275                 280                 285

Asn Ser Leu Thr Tyr Gln Leu Leu Ala Arg Glu Leu Gly Pro Leu Tyr
290                 295                 300

Thr Asn Ile Thr Ala Asp Ile Gly Thr Asp Pro Arg Gly Pro Arg Ala
305                 310                 315                 320

Pro Ser Gly Pro Arg Tyr Pro Pro Gly Ser Ser Gln Ala Phe Arg Gln
                325                 330                 335

Glu Met Leu Gln Arg Arg Pro Pro Ala Arg Pro Gly Pro Leu Ser Thr
            340                 345                 350

Ala Asn His Thr Ala Leu Arg Gly Ser His
        355                 360

<210> SEQ ID NO 58
<211> LENGTH: 348
<212> TYPE: PRT
<213> ORGANISM: Homo sapiens

<400> SEQUENCE: 58

Met Ala Glu Lys Val Leu Val Thr Gly Gly Ala Gly Tyr Ile Gly Ser
 1                   5                  10                  15

His Thr Val Leu Glu Leu Leu Glu Ala Gly Tyr Leu Pro Val Val Ile
                 20                  25                  30

Asp Asn Phe His Asn Ala Phe Arg Gly Gly Gly Ser Leu Pro Glu Ser
             35                  40                  45

Leu Arg Arg Val Gln Glu Leu Thr Gly Arg Ser Val Glu Phe Glu Glu
         50                  55                  60
```

```
Met Asp Ile Leu Asp Gln Gly Ala Leu Gln Arg Leu Phe Lys Lys Tyr
 65                  70                  75                  80

Ser Phe Met Ala Val Ile His Phe Ala Gly Leu Lys Ala Val Gly Glu
                 85                  90                  95

Ser Val Gln Lys Pro Leu Asp Tyr Tyr Arg Val Asn Leu Thr Gly Thr
            100                 105                 110

Ile Gln Leu Leu Glu Ile Met Lys Ala His Gly Val Lys Asn Leu Val
        115                 120                 125

Phe Ser Ser Ser Ala Thr Val Tyr Gly Asn Pro Gln Tyr Leu Pro Leu
    130                 135                 140

Asp Glu Ala His Pro Thr Gly Gly Cys Thr Asn Pro Tyr Gly Lys Ser
145                 150                 155                 160

Lys Phe Phe Ile Glu Glu Met Ile Arg Asp Leu Cys Gln Ala Asp Lys
                165                 170                 175

Thr Trp Asn Val Val Leu Leu Arg Tyr Phe Asn Pro Thr Gly Ala His
                180                 185                 190

Ala Ser Gly Cys Ile Gly Glu Asp Pro Gln Gly Ile Pro Asn Asn Leu
                195                 200                 205

Met Pro Tyr Val Ser Gln Val Ala Ile Gly Arg Arg Glu Ala Leu Asn
210                 215                 220

Val Phe Gly Asn Asp Tyr Asp Thr Glu Asp Gly Thr Gly Val Arg Asp
225                 230                 235                 240

Tyr Ile His Val Val Asp Leu Ala Lys Gly His Ile Ala Ala Leu Arg
                245                 250                 255

Lys Leu Lys Glu Gln Cys Gly Cys Arg Ile Tyr Asn Leu Gly Thr Gly
                260                 265                 270

Thr Gly Tyr Ser Val Leu Gln Met Val Gln Ala Met Glu Lys Ala Ser
            275                 280                 285

Gly Lys Lys Ile Pro Tyr Lys Val Val Arg Arg Glu Gly Asp Val
            290                 295                 300

Ala Ala Cys Tyr Ala Asn Pro Ser Leu Ala Gln Glu Glu Leu Gly Trp
305                 310                 315                 320

Thr Ala Ala Leu Gly Leu Asp Arg Met Cys Glu Asp Leu Trp Arg Trp
                325                 330                 335

Gln Lys Gln Asn Pro Ser Gly Phe Gly Thr Gln Ala
            340                 345

<210> SEQ ID NO 59
<211> LENGTH: 699
<212> TYPE: PRT
<213> ORGANISM: Saccharomyces cerevisiae

<400> SEQUENCE: 59

Met Thr Ala Gln Leu Gln Ser Glu Ser Thr Ser Lys Ile Val Leu Val
  1               5                  10                  15

Thr Gly Gly Ala Gly Tyr Ile Gly Ser His Thr Val Val Glu Leu Ile
             20                  25                  30

Glu Asn Gly Tyr Asp Cys Val Val Ala Asp Asn Leu Ser Asn Ser Thr
         35                  40                  45

Tyr Asp Ser Val Ala Arg Leu Glu Val Leu Thr Lys His His Ile Pro
 50                  55                  60

Phe Tyr Glu Val Asp Leu Cys Asp Arg Lys Gly Leu Glu Lys Val Phe
 65                  70                  75                  80

Lys Glu Tyr Lys Ile Asp Ser Val Ile His Phe Ala Gly Leu Lys Ala
                 85                  90                  95
```

-continued

```
Val Gly Glu Ser Thr Gln Ile Pro Leu Arg Tyr Tyr His Asn Asn Ile
                100                 105                 110

Leu Gly Thr Val Val Leu Glu Leu Met Gln Gln Tyr Asn Val Ser
            115                 120                 125

Lys Phe Val Phe Ser Ser Ala Thr Val Tyr Gly Asp Ala Thr Arg
        130                 135                 140

Phe Pro Asn Met Ile Pro Ile Pro Glu Glu Cys Pro Leu Gly Pro Thr
145                 150                 155                 160

Asn Pro Tyr Gly His Thr Lys Tyr Ala Ile Glu Asn Ile Leu Asn Asp
                165                 170                 175

Leu Tyr Asn Ser Asp Lys Lys Ser Trp Lys Phe Ala Ile Leu Arg Tyr
            180                 185                 190

Phe Asn Pro Ile Gly Ala His Pro Ser Gly Leu Ile Gly Glu Asp Pro
        195                 200                 205

Leu Gly Ile Pro Asn Asn Leu Leu Pro Tyr Met Ala Gln Val Ala Val
    210                 215                 220

Gly Arg Arg Glu Lys Leu Tyr Ile Phe Gly Asp Asp Tyr Asp Ser Arg
225                 230                 235                 240

Asp Gly Thr Pro Ile Arg Asp Tyr Ile His Val Asp Leu Ala Lys
                245                 250                 255

Gly His Ile Ala Ala Leu Gln Tyr Leu Glu Ala Tyr Asn Glu Asn Glu
            260                 265                 270

Gly Leu Cys Arg Glu Trp Asn Leu Gly Ser Gly Lys Gly Ser Thr Val
        275                 280                 285

Phe Glu Val Tyr His Ala Phe Cys Lys Ala Ser Gly Ile Asp Leu Pro
    290                 295                 300

Tyr Lys Val Thr Gly Arg Arg Ala Gly Asp Val Leu Asn Leu Thr Ala
305                 310                 315                 320

Lys Pro Asp Arg Ala Lys Arg Glu Leu Lys Trp Gln Thr Glu Leu Gln
                325                 330                 335

Val Glu Asp Ser Cys Lys Asp Leu Trp Lys Trp Thr Thr Glu Asn Pro
            340                 345                 350

Phe Gly Tyr Gln Leu Arg Gly Val Glu Ala Arg Phe Ser Ala Glu Asp
        355                 360                 365

Met Arg Tyr Asp Ala Arg Phe Val Thr Ile Gly Ala Gly Thr Arg Phe
    370                 375                 380

Gln Ala Thr Phe Ala Asn Leu Gly Ala Ser Ile Val Asp Leu Lys Val
385                 390                 395                 400

Asn Gly Gln Ser Val Val Leu Gly Tyr Glu Asn Glu Glu Gly Tyr Leu
                405                 410                 415

Asn Pro Asp Ser Ala Tyr Ile Gly Ala Thr Ile Gly Arg Tyr Ala Asn
            420                 425                 430

Arg Ile Ser Lys Gly Lys Phe Ser Leu Cys Asn Lys Asp Tyr Gln Leu
        435                 440                 445

Thr Val Asn Asn Gly Val Asn Ala Asn His Ser Ser Ile Gly Ser Phe
    450                 455                 460

His Arg Lys Arg Phe Leu Gly Pro Ile Ile Gln Asn Pro Ser Lys Asp
465                 470                 475                 480

Val Phe Thr Ala Glu Tyr Met Leu Ile Asp Asn Glu Lys Asp Thr Glu
                485                 490                 495

Phe Pro Gly Asp Leu Leu Val Thr Ile Gln Tyr Thr Val Asn Val Ala
            500                 505                 510
```

```
Gln Lys Ser Leu Glu Met Val Tyr Lys Gly Lys Leu Thr Ala Gly Glu
            515                 520                 525

Ala Thr Pro Ile Asn Leu Thr Asn His Ser Tyr Phe Asn Leu Asn Lys
        530                 535                 540

Pro Tyr Gly Asp Thr Ile Glu Gly Thr Glu Ile Met Val Arg Ser Lys
545                 550                 555                 560

Lys Ser Val Asp Val Asp Lys Asn Met Ile Pro Thr Gly Asn Ile Val
                565                 570                 575

Asp Arg Glu Ile Ala Thr Phe Asn Ser Thr Lys Pro Thr Val Leu Gly
            580                 585                 590

Pro Lys Asn Pro Gln Phe Asp Cys Cys Phe Val Val Asp Glu Asn Ala
        595                 600                 605

Lys Pro Ser Gln Ile Asn Thr Leu Asn Asn Glu Leu Thr Leu Ile Val
    610                 615                 620

Lys Ala Phe His Pro Asp Ser Asn Ile Thr Leu Glu Val Leu Ser Thr
625                 630                 635                 640

Glu Pro Thr Tyr Gln Phe Tyr Thr Gly Asp Phe Leu Ser Ala Gly Tyr
                645                 650                 655

Glu Ala Arg Gln Gly Phe Ala Ile Glu Pro Gly Arg Tyr Ile Asp Ala
            660                 665                 670

Ile Asn Gln Glu Asn Trp Lys Asp Cys Val Thr Leu Lys Asn Gly Glu
        675                 680                 685

Thr Tyr Gly Ser Lys Ile Val Tyr Arg Phe Ser
    690                 695

<210> SEQ ID NO 60
<211> LENGTH: 394
<212> TYPE: PRT
<213> ORGANISM: Homo sapiens

<400> SEQUENCE: 60

Met Ala Ala Val Gly Ala Gly Gly Ser Thr Ala Ala Pro Gly Pro Gly
  1               5                  10                  15

Ala Val Ser Ala Gly Ala Leu Glu Pro Gly Thr Ala Ser Ala Ala His
             20                  25                  30

Arg Arg Leu Lys Tyr Ile Ser Leu Ala Val Leu Val Val Gln Asn Ala
         35                  40                  45

Ser Leu Ile Leu Ser Ile Arg Tyr Ala Arg Thr Leu Pro Gly Asp Arg
     50                  55                  60

Phe Phe Ala Thr Thr Ala Val Val Met Ala Glu Val Leu Lys Gly Leu
 65                  70                  75                  80

Thr Cys Leu Leu Leu Leu Phe Ala Gln Lys Arg Gly Asn Val Lys His
                 85                  90                  95

Leu Val Leu Phe Leu His Glu Ala Val Leu Val Gln Tyr Val Asp Thr
            100                 105                 110

Leu Lys Leu Ala Val Pro Ser Leu Ile Tyr Thr Leu Gln Asn Asn Leu
        115                 120                 125

Gln Tyr Val Ala Ile Ser Asn Leu Pro Ala Ala Thr Phe Gln Val Thr
    130                 135                 140

Tyr Gln Leu Lys Ile Leu Thr Thr Ala Leu Phe Ser Val Leu Met Leu
145                 150                 155                 160

Asn Arg Ser Leu Ser Arg Leu Gln Trp Ala Ser Leu Leu Leu Leu Phe
                165                 170                 175

Thr Gly Val Ala Ile Val Gln Ala Gln Gln Ala Gly Gly Gly Gly Pro
            180                 185                 190
```

```
Arg Pro Leu Asp Gln Asn Pro Gly Ala Gly Leu Ala Ala Val Val Ala
        195                 200                 205

Ser Cys Leu Ser Ser Gly Phe Ala Gly Val Tyr Phe Glu Lys Ile Leu
    210                 215                 220

Lys Gly Ser Ser Gly Ser Val Trp Leu Arg Asn Leu Gln Leu Gly Leu
225                 230                 235                 240

Phe Gly Thr Ala Leu Gly Leu Val Gly Leu Trp Trp Ala Glu Gly Thr
                245                 250                 255

Ala Val Ala Thr Arg Gly Phe Phe Gly Tyr Thr Pro Ala Val Trp
            260                 265                 270

Gly Val Val Leu Asn Gln Ala Phe Gly Gly Leu Leu Ala Val Val
        275                 280                 285

Val Lys Tyr Ala Asp Asn Ile Leu Lys Gly Phe Ala Thr Ser Leu Ser
    290                 295                 300

Ile Val Leu Ser Thr Val Ala Ser Ile Arg Leu Phe Gly Phe His Val
305                 310                 315                 320

Asp Pro Leu Phe Ala Leu Gly Ala Gly Leu Val Ile Gly Ala Val Tyr
                325                 330                 335

Leu Tyr Ser Leu Pro Arg Gly Ala Ala Lys Ala Ile Ala Ser Ala Ser
                340                 345                 350

Ala Ser Ala Ser Gly Pro Cys Val His Gln Pro Pro Gly Gln Pro
            355                 360                 365

Pro Pro Pro Gln Leu Ser Ser His Arg Gly Asp Leu Ile Thr Glu Pro
    370                 375                 380

Phe Leu Pro Lys Ser Val Leu Val Lys Glx
385                 390

<210> SEQ ID NO 61
<211> LENGTH: 397
<212> TYPE: PRT
<213> ORGANISM: Homo sapiens

<400> SEQUENCE: 61

Met Ala Ala Val Gly Ala Gly Gly Ser Thr Ala Pro Gly Pro Gly
  1               5                  10                  15

Ala Val Ser Ala Gly Ala Leu Glu Pro Gly Thr Ala Ser Ala Ala His
            20                  25                  30

Arg Arg Leu Lys Tyr Ile Ser Leu Ala Val Leu Val Val Gln Asn Ala
        35                  40                  45

Ser Leu Ile Leu Ser Ile Arg Tyr Ala Arg Thr Leu Pro Gly Asp Arg
    50                  55                  60

Phe Phe Ala Thr Thr Ala Val Val Met Ala Glu Val Leu Lys Gly Leu
65                  70                  75                  80

Thr Cys Leu Leu Leu Leu Phe Ala Gln Lys Arg Gly Asn Val Lys His
                85                  90                  95

Leu Val Leu Phe Leu His Glu Ala Val Leu Val Gln Tyr Val Asp Thr
                100                 105                 110

Leu Lys Leu Ala Val Pro Ser Leu Ile Tyr Thr Leu Gln Asn Asn Leu
            115                 120                 125

Gln Tyr Val Ala Ile Ser Asn Leu Pro Ala Ala Thr Phe Gln Val Thr
        130                 135                 140

Tyr Gln Leu Lys Ile Leu Thr Thr Ala Leu Phe Ser Val Leu Met Leu
145                 150                 155                 160

Asn Arg Ser Leu Ser Arg Leu Gln Trp Ala Ser Leu Leu Leu Leu Phe
```

```
                    165                 170                 175
Thr Gly Val Ala Ile Val Gln Ala Gln Gln Ala Gly Gly Gly Pro
                180                 185                 190

Arg Pro Leu Asp Gln Asn Pro Gly Ala Gly Leu Ala Ala Val Val Ala
            195                 200                 205

Ser Cys Leu Ser Ser Gly Phe Ala Gly Val Tyr Phe Glu Lys Ile Leu
    210                 215                 220

Lys Gly Ser Ser Gly Ser Val Trp Leu Arg Asn Leu Gln Leu Gly Leu
225                 230                 235                 240

Phe Gly Thr Ala Leu Gly Leu Val Gly Leu Trp Trp Ala Glu Gly Thr
                245                 250                 255

Ala Val Ala Thr Arg Gly Phe Phe Gly Tyr Thr Pro Ala Val Trp
            260                 265                 270

Gly Val Val Leu Asn Gln Ala Phe Gly Gly Leu Leu Ala Val Val
                275                 280                 285

Val Lys Tyr Ala Asp Asn Ile Leu Lys Gly Phe Ala Thr Ser Leu Ser
290                 295                 300

Ile Val Leu Ser Thr Val Ala Ser Ile Arg Leu Phe Gly Phe His Val
305                 310                 315                 320

Asp Pro Leu Phe Ala Leu Gly Ala Gly Leu Val Ile Gly Ala Val Tyr
                325                 330                 335

Leu Tyr Ser Leu Pro Arg Gly Ala Ala Lys Ala Ile Ala Ser Ala Ser
                340                 345                 350

Ala Ser Ala Ser Gly Pro Cys Val His Gln Pro Pro Gly Gln Pro
            355                 360                 365

Pro Pro Pro Gln Leu Ser Ser His Arg Gly Asp Leu Ile Thr Glu Pro
370                 375                 380

Phe Leu Pro Lys Leu Leu Thr Lys Val Lys Gly Ser Glx
385                 390                 395

<210> SEQ ID NO 62
<211> LENGTH: 357
<212> TYPE: PRT
<213> ORGANISM: Drosophila melanogaster

<400> SEQUENCE: 62

Met Asn Ser Ile His Met Asn Ala Asn Thr Leu Lys Tyr Ile Ser Leu
  1               5                  10                  15

Leu Thr Leu Thr Leu Gln Asn Ala Ile Leu Gly Leu Ser Met Arg Tyr
                 20                  25                  30

Ala Arg Thr Arg Pro Gly Asp Ile Phe Leu Ser Ser Thr Ala Val Leu
             35                  40                  45

Met Ala Glu Phe Ala Lys Leu Ile Thr Cys Leu Phe Leu Val Phe Asn
         50                  55                  60

Glu Glu Gly Lys Asp Ala Gln Lys Phe Val Arg Ser Leu His Lys Thr
 65                  70                  75                  80

Ile Ile Ala Asn Pro Met Asp Thr Leu Lys Val Cys Val Pro Ser Leu
                 85                  90                  95

Val Tyr Ile Val Gln Asn Asn Leu Leu Tyr Val Ser Ala Ser His Leu
                100                 105                 110

Asp Ala Ala Thr Tyr Gln Val Thr Tyr Gln Leu Lys Ile Leu Thr Thr
            115                 120                 125

Ala Met Phe Ala Val Val Ile Leu Arg Arg Lys Leu Leu Asn Thr Gln
        130                 135                 140
```

```
Trp Gly Ala Leu Leu Leu Leu Val Met Gly Ile Val Leu Val Gln Leu
145                 150                 155                 160

Ala Gln Thr Glu Gly Pro Thr Ser Gly Ser Ala Gly Gly Ala Ala Ala
            165                 170                 175

Ala Ala Thr Ala Ala Ser Ser Gly Gly Ala Pro Glu Gln Asn Arg Met
        180                 185                 190

Leu Gly Leu Trp Ala Ala Leu Gly Ala Cys Phe Leu Ser Gly Phe Ala
    195                 200                 205

Gly Ile Tyr Phe Glu Lys Ile Leu Lys Gly Ala Glu Ile Ser Val Trp
210                 215                 220

Met Arg Asn Val Gln Leu Ser Leu Leu Ser Ile Pro Phe Gly Leu Leu
225                 230                 235                 240

Thr Cys Phe Val Asn Asp Gly Ser Arg Ile Phe Asp Gln Gly Phe Phe
                245                 250                 255

Lys Gly Tyr Asp Leu Phe Val Trp Tyr Leu Val Leu Gln Ala Gly
            260                 265                 270

Gly Gly Leu Ile Val Ala Val Val Lys Tyr Ala Asp Asn Ile Leu
        275                 280                 285

Lys Gly Phe Ala Thr Ser Leu Ala Ile Ile Ile Ser Cys Val Ala Ser
290                 295                 300

Ile Tyr Ile Phe Asp Phe Asn Leu Thr Leu Gln Phe Ser Phe Gly Ala
305                 310                 315                 320

Gly Leu Val Ile Ala Ser Ile Phe Leu Tyr Gly Tyr Asp Pro Ala Arg
                325                 330                 335

Ser Ala Pro Lys Pro Thr Met His Gly Pro Gly Asp Glu Glu Lys
            340                 345                 350

Leu Leu Pro Arg Val
        355

<210> SEQ ID NO 63
<211> LENGTH: 353
<212> TYPE: PRT
<213> ORGANISM: Schizosaccharomyces pombe

<400> SEQUENCE: 63

Met Ala Val Lys Gly Asp Asp Val Lys Trp Lys Gly Ile Pro Met Lys
1               5                   10                  15

Tyr Ile Ala Leu Val Leu Leu Thr Val Gln Asn Ser Ala Leu Ile Leu
            20                  25                  30

Thr Leu Asn Tyr Ser Arg Ile Met Pro Gly Tyr Asp Asp Lys Arg Tyr
        35                  40                  45

Phe Thr Ser Thr Ala Val Leu Leu Asn Glu Leu Ile Lys Leu Val Val
    50                  55                  60

Cys Phe Ser Val Gly Tyr His Gln Phe Arg Lys Asn Val Gly Lys Glu
65                  70                  75                  80

Ala Lys Leu Arg Ala Phe Leu Pro Gln Ile Phe Gly Gly Asp Ser Trp
                85                  90                  95

Lys Leu Ala Ile Pro Ala Phe Leu Tyr Thr Cys Gln Asn Asn Leu Gln
            100                 105                 110

Tyr Val Ala Ala Gly Asn Leu Thr Ala Ala Ser Phe Gln Val Thr Tyr
        115                 120                 125

Gln Leu Lys Ile Leu Thr Thr Ala Ile Phe Ser Ile Leu Leu Leu His
    130                 135                 140

Arg Arg Leu Gly Pro Met Lys Trp Phe Ser Leu Phe Leu Leu Thr Gly
145                 150                 155                 160
```

```
Gly Ile Ala Ile Val Gln Leu Gln Asn Leu Asn Ser Asp Asp Gln Met
            165                 170                 175

Ser Ala Gly Pro Met Asn Pro Val Thr Gly Phe Ser Ala Val Leu Val
        180                 185                 190

Ala Cys Leu Ile Ser Gly Leu Ala Gly Val Tyr Phe Glu Lys Val Leu
    195                 200                 205

Lys Asp Thr Asn Pro Ser Leu Trp Val Arg Asn Val Gln Leu Ser Phe
210                 215                 220

Phe Ser Leu Phe Pro Cys Leu Phe Thr Ile Leu Met Lys Asp Tyr His
225                 230                 235                 240

Asn Ile Ala Glu Asn Gly Phe Phe Gly Tyr Asn Ser Ile Val Trp
            245                 250                 255

Leu Ala Ile Leu Leu Gln Ala Gly Gly Ile Ile Val Ala Leu Cys
        260                 265                 270

Val Ala Phe Ala Asp Asn Ile Met Lys Asn Phe Ser Thr Ser Ile Ser
    275                 280                 285

Ile Ile Ile Ser Ser Leu Ala Ser Val Tyr Leu Met Asp Phe Lys Ile
290                 295                 300

Ser Leu Thr Phe Leu Ile Gly Val Met Leu Val Ile Ala Ala Thr Phe
305                 310                 315                 320

Leu Tyr Thr Lys Pro Glu Ser Lys Pro Ser Pro Ser Arg Gly Thr Tyr
            325                 330                 335

Ile Pro Met Thr Thr Gln Asp Ala Ala Ala Lys Asp Val Asp His Lys
        340                 345                 350

His

<210> SEQ ID NO 64
<211> LENGTH: 353
<212> TYPE: PRT
<213> ORGANISM: Schizosaccharomyces pombe

<400> SEQUENCE: 64

Met Thr Gly Val His Glu Gly Thr Val Leu Val Thr Gly Gly Ala Gly
 1               5                  10                  15

Tyr Ile Gly Ser His Thr Cys Val Val Leu Glu Lys Gly Tyr Asp
            20                  25                  30

Val Val Ile Val Asp Asn Leu Cys Asn Ser Arg Val Glu Ala Val His
        35                  40                  45

Arg Ile Glu Lys Leu Thr Gly Lys Lys Val Ile Phe His Gln Val Asp
    50                  55                  60

Leu Leu Asp Glu Pro Ala Leu Asp Lys Val Phe Ala Asn Gln Asn Ile
65                  70                  75                  80

Ser Ala Val Ile His Phe Ala Gly Leu Lys Ala Val Gly Glu Ser Val
            85                  90                  95

Gln Val Pro Leu Ser Tyr Tyr Lys Asn Asn Ile Ser Gly Thr Ile Asn
        100                 105                 110

Leu Ile Glu Cys Met Lys Lys Tyr Asn Val Arg Asp Phe Val Phe Ser
    115                 120                 125

Ser Ser Ala Thr Val Tyr Gly Asp Pro Thr Arg Pro Gly Gly Thr Ile
130                 135                 140

Pro Ile Pro Glu Ser Cys Pro Arg Glu Gly Thr Ser Pro Tyr Gly Arg
145                 150                 155                 160

Thr Lys Leu Phe Ile Glu Asn Ile Ile Glu Asp Glu Thr Lys Val Asn
            165                 170                 175
```

Lys Ser Leu Asn Ala Ala Leu Leu Arg Tyr Phe Asn Pro Gly Gly Ala
            180                 185                 190

His Pro Ser Gly Glu Leu Gly Glu Asp Pro Leu Gly Ile Pro Asn Asn
        195                 200                 205

Leu Leu Pro Tyr Ile Ala Gln Val Ala Val Gly Arg Leu Asp His Leu
    210                 215                 220

Asn Val Phe Gly Asp Asp Tyr Pro Thr Ser Asp Gly Thr Pro Ile Arg
225                 230                 235                 240

Asp Tyr Ile His Val Cys Asp Leu Ala Glu Ala His Val Ala Ala Leu
                245                 250                 255

Asp Tyr Leu Arg Gln His Phe Val Ser Cys Arg Pro Trp Asn Leu Gly
            260                 265                 270

Ser Gly Thr Gly Ser Thr Val Phe Gln Val Leu Asn Ala Phe Ser Lys
        275                 280                 285

Ala Val Gly Arg Asp Leu Pro Tyr Lys Val Thr Pro Arg Arg Ala Gly
    290                 295                 300

Asp Val Val Asn Leu Thr Ala Asn Pro Thr Arg Ala Asn Glu Glu Leu
305                 310                 315                 320

Lys Trp Lys Thr Ser Arg Ser Ile Tyr Glu Ile Cys Val Asp Thr Trp
                325                 330                 335

Arg Trp Gln Gln Lys Tyr Pro Tyr Gly Phe Asp Leu Thr His Thr Lys
            340                 345                 350

Thr

<210> SEQ ID NO 65
<211> LENGTH: 348
<212> TYPE: PRT
<213> ORGANISM: Homo sapiens

<400> SEQUENCE: 65

Met Ala Glu Lys Val Leu Val Thr Gly Gly Ala Gly Tyr Ile Gly Ser
1               5                   10                  15

His Thr Val Leu Glu Leu Leu Glu Ala Gly Tyr Leu Pro Val Val Ile
            20                  25                  30

Asp Asn Phe His Asn Ala Phe Arg Gly Gly Gly Ser Leu Pro Glu Ser
        35                  40                  45

Leu Arg Arg Val Gln Glu Leu Thr Gly Arg Ser Val Glu Phe Glu Glu
    50                  55                  60

Met Asp Ile Leu Asp Gln Gly Ala Leu Gln Arg Leu Phe Lys Lys Tyr
65                  70                  75                  80

Ser Phe Met Ala Val Ile His Phe Ala Gly Leu Lys Ala Val Gly Glu
                85                  90                  95

Ser Val Gln Lys Pro Leu Asp Tyr Tyr Arg Val Asn Leu Thr Gly Thr
            100                 105                 110

Ile Gln Leu Leu Glu Ile Met Lys Ala His Gly Val Lys Asn Leu Val
        115                 120                 125

Phe Ser Ser Ser Ala Thr Val Tyr Gly Asn Pro Gln Tyr Leu Pro Leu
    130                 135                 140

Asp Glu Ala His Pro Thr Gly Gly Cys Thr Asn Pro Tyr Gly Lys Ser
145                 150                 155                 160

Lys Phe Phe Ile Glu Glu Met Ile Arg Asp Leu Cys Gln Ala Asp Lys
                165                 170                 175

Thr Trp Asn Val Val Leu Leu Arg Tyr Phe Asn Pro Thr Gly Ala His
            180                 185                 190

```
Ala Ser Gly Cys Ile Gly Glu Asp Pro Gln Gly Ile Pro Asn Asn Leu
            195                 200                 205

Met Pro Tyr Val Ser Gln Val Ala Ile Gly Arg Arg Glu Ala Leu Asn
        210                 215                 220

Val Phe Gly Asn Asp Tyr Asp Thr Glu Asp Gly Thr Gly Val Arg Asp
225                 230                 235                 240

Tyr Ile His Val Val Asp Leu Ala Lys Gly His Ile Ala Ala Leu Arg
                245                 250                 255

Lys Leu Lys Glu Gln Cys Gly Cys Arg Ile Tyr Asn Leu Gly Thr Gly
            260                 265                 270

Thr Gly Tyr Ser Val Leu Gln Met Val Gln Ala Met Glu Lys Ala Ser
        275                 280                 285

Gly Lys Lys Ile Pro Tyr Lys Val Val Ala Arg Arg Glu Gly Asp Val
    290                 295                 300

Ala Ala Cys Tyr Ala Asn Pro Ser Leu Ala Gln Glu Glu Leu Gly Trp
305                 310                 315                 320

Thr Ala Ala Leu Gly Leu Asp Arg Met Cys Glu Asp Leu Trp Arg Trp
                325                 330                 335

Gln Lys Gln Asn Pro Ser Gly Phe Gly Thr Gln Ala
            340                 345

<210> SEQ ID NO 66
<211> LENGTH: 338
<212> TYPE: PRT
<213> ORGANISM: Escherichia coli

<400> SEQUENCE: 66

Met Arg Val Leu Val Thr Gly Gly Ser Gly Tyr Ile Gly Ser His Thr
1               5                   10                  15

Cys Val Gln Leu Leu Gln Asn Gly His Asp Val Ile Ile Leu Asp Asn
            20                  25                  30

Leu Cys Asn Ser Lys Arg Ser Val Leu Pro Val Ile Glu Arg Leu Gly
        35                  40                  45

Gly Lys His Pro Thr Phe Val Glu Gly Asp Ile Arg Asn Glu Ala Leu
    50                  55                  60

Met Thr Glu Ile Leu His Asp His Ala Ile Asp Thr Val Ile His Phe
65                  70                  75                  80

Ala Gly Leu Lys Ala Val Gly Glu Ser Val Gln Lys Pro Leu Glu Tyr
                85                  90                  95

Tyr Asp Asn Asn Val Asn Gly Thr Leu Arg Leu Ile Ser Ala Met Arg
            100                 105                 110

Ala Ala Asn Val Lys Asn Phe Ile Phe Ser Ser Ser Ala Thr Val Tyr
        115                 120                 125

Gly Asp Asn Pro Lys Ile Pro Tyr Val Glu Ser Phe Pro Thr Gly Thr
    130                 135                 140

Pro Gln Ser Pro Tyr Gly Lys Ser Lys Leu Met Val Glu Gln Ile Leu
145                 150                 155                 160

Thr Asp Leu Gln Lys Ala Gln Pro Asp Trp Ser Ile Ala Leu Leu Arg
                165                 170                 175

Tyr Phe Asn Pro Val Gly Ala His Pro Ser Gly Asp Met Gly Glu Asp
            180                 185                 190

Pro Gln Gly Ile Pro Asn Asn Leu Met Pro Tyr Ile Ala Gln Val Ala
        195                 200                 205

Val Gly Arg Arg Asp Ser Leu Ala Ile Phe Gly Asn Asp Tyr Pro Thr
```

-continued

```
                210                 215                 220
Glu Asp Gly Thr Gly Val Arg Asp Tyr Ile His Val Met Asp Leu Ala
225                 230                 235                 240

Asp Gly His Val Val Ala Met Glu Lys Leu Ala Asn Lys Pro Gly Val
                245                 250                 255

His Ile Tyr Asn Leu Gly Ala Gly Val Gly Asn Ser Val Leu Asp Val
            260                 265                 270

Val Asn Ala Phe Ser Lys Ala Cys Gly Lys Pro Val Asn Tyr His Phe
        275                 280                 285

Ala Pro Arg Arg Glu Gly Asp Leu Pro Ala Tyr Trp Ala Asp Ala Ser
290                 295                 300

Lys Ala Asp Arg Glu Leu Asn Trp Arg Val Thr Arg Thr Leu Asp Glu
305                 310                 315                 320

Met Ala Gln Asp Thr Trp His Trp Gln Ser Arg His Pro Gln Gly Tyr
                325                 330                 335

Pro Asp

<210> SEQ ID NO 67
<211> LENGTH: 362
<212> TYPE: PRT
<213> ORGANISM: Saccharomyces cerevisiae

<400> SEQUENCE: 67

Met Thr Ala Gln Leu Gln Ser Glu Ser Thr Ser Lys Ile Val Leu Val
1               5                   10                  15

Thr Gly Gly Ala Gly Tyr Ile Gly Ser His Thr Val Val Glu Leu Ile
            20                  25                  30

Glu Asn Gly Tyr Asp Cys Val Val Ala Asp Asn Leu Ser Asn Ser Thr
        35                  40                  45

Tyr Asp Ser Val Ala Arg Leu Glu Val Leu Thr Lys His His Ile Pro
    50                  55                  60

Phe Tyr Glu Val Asp Leu Cys Asp Arg Lys Gly Leu Glu Lys Val Phe
65                  70                  75                  80

Lys Glu Tyr Lys Ile Asp Ser Val Ile His Phe Ala Gly Leu Lys Ala
                85                  90                  95

Val Gly Glu Ser Thr Gln Ile Pro Leu Arg Tyr Tyr His Asn Asn Ile
            100                 105                 110

Leu Gly Thr Val Val Leu Leu Glu Leu Met Gln Gln Tyr Asn Val Ser
        115                 120                 125

Lys Phe Val Phe Ser Ser Ser Ala Thr Val Tyr Gly Asp Ala Thr Arg
    130                 135                 140

Phe Pro Asn Met Ile Pro Ile Pro Glu Glu Cys Pro Leu Gly Pro Thr
145                 150                 155                 160

Asn Pro Tyr Gly His Thr Lys Tyr Ala Ile Glu Asn Ile Leu Asn Asp
                165                 170                 175

Leu Tyr Asn Ser Asp Lys Lys Ser Trp Lys Phe Ala Ile Leu Arg Tyr
            180                 185                 190

Phe Asn Pro Ile Gly Ala His Pro Ser Gly Leu Ile Gly Glu Asp Pro
        195                 200                 205

Leu Gly Ile Pro Asn Asn Leu Leu Pro Tyr Met Ala Gln Val Ala Val
    210                 215                 220

Gly Arg Arg Glu Lys Leu Tyr Ile Phe Gly Asp Asp Tyr Asp Ser Arg
225                 230                 235                 240

Asp Gly Thr Pro Ile Arg Asp Tyr Ile His Val Val Asp Leu Ala Lys
```

```
                    245                 250                 255
Gly His Ile Ala Ala Leu Gln Tyr Leu Glu Ala Tyr Asn Glu Asn Glu
            260                 265                 270

Gly Leu Cys Arg Glu Trp Asn Leu Gly Ser Gly Lys Gly Ser Thr Val
        275                 280                 285

Phe Glu Val Tyr His Ala Phe Cys Lys Ala Ser Gly Ile Asp Leu Pro
    290                 295                 300

Tyr Lys Val Thr Gly Arg Arg Ala Gly Asp Val Leu Asn Leu Thr Ala
305                 310                 315                 320

Lys Pro Asp Arg Ala Lys Arg Glu Leu Lys Trp Gln Thr Glu Leu Gln
            325                 330                 335

Val Glu Asp Ser Cys Lys Asp Leu Trp Lys Trp Thr Thr Glu Asn Pro
        340                 345                 350

Phe Gly Tyr Gln Leu Arg Gly Val Glu Ala
    355                 360

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Ser Gly Gly
  1

<210> SEQ ID NO 69
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

His Asp Glu Leu
  1

<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Lys Asp Glu Leu
  1

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 71

His His His His His His
  1               5
```

PRODUCTION OF GALACTOSYLATED GLYCOPROTEINS IN LOWER EUKARYOTES

CROSS-REFERENCE TO RELATED APPLICATIONS

This application is a continuation-in-part of U.S. application Ser. No. 10/371,877, filed on Feb. 20, 2003, which is a continuation-in-part of U.S. application Ser. No. 09/892,591, filed Jun. 27, 2001, (now U.S. Pat. No. 7,029,872) which claims the benefit under 35 U.S.C. §119(e) of U.S. Provisional Application No. 60/214,358, filed Jun. 28, 2000, U.S. Provisional Application No. 60/215,638, filed Jun. 30, 2000, and U.S. Provisional Application No. 60/279,997, filed Mar. 30, 2001, each of which is incorporated herein by reference in its entirety. This application is also a continuation-in-part of PCT/US02/41510, filed on Dec. 24, 2002, which claims the benefit of U.S. Provisional Application No. 60/344,169, filed Dec. 27, 2001, each of which is incorporated herein by reference in its entirety. This application also claims priority to U.S. Provisional Application No. 60/562,424, filed Apr. 15, 2004, which is incorporated herein by reference in its entirety.

FIELD OF THE INVENTION

The present invention relates to the field of protein glycosylation engineering in lower eukaryotes, specifically the production of glycoproteins having terminal galactose residues. The present invention further relates to novel host cells comprising genes encoding enzymes involved in galactosyl transfer on glycans and production of glycoproteins that are particularly useful as therapeutic agents.

BACKGROUND OF THE INVENTION

Yeast and filamentous fungi have both been successfully used for the production of recombinant proteins, both intracellular and secreted (Cereghino, J. L. and J. M. Cregg 2000 *FEMS Microbiology Reviews* 24(1): 45-66; Harkki, A., et al. 1989 *Bio-Technology* 7(6): 596; Berka, R. M., et al. 1992 *Abstr. Papers Amer. Chem. Soc.* 203: 121-BIOT; Svetina, M., et al. 2000 *J. Biotechnol.* 76(2-3): 245-251). Various yeasts, such as *K. lactis, Pichia pastoris, Pichia methanolica,* and *Hansenula polymorpha*, have played particularly important roles as eukaryotic expression systems because they are able to grow to high cell densities and secrete large quantities of recombinant protein. Likewise, filamentous fungi, such as *Aspergillus niger, Fusarium* sp, *Neurospora crassa* and others, have been used to efficiently produce glycoproteins in industrial scale. However, glycoproteins expressed in any of these eukaryotic microorganisms differ substantially in N-glycan structure from those in animals. This has prevented the use of yeast or filamentous fungi as hosts for the production of glycosylated therapeutic proteins.

Currently, expression systems such as yeast, filamentous fungi, plants, algae and insect cell lines (lower eukaryotes) are being investigated for the production of therapeutic proteins, which are safer, faster and yield higher product titers than mammalian systems. These systems share a common secretory pathway in N-linked oligosaccharide synthesis. Recently, it was shown that the secretory pathway of *P. pastoris* can be genetically re-engineered to perform sequential glycosylation reactions that mimic early processing of N-glycans in humans and other higher mammals (Choi et al., *Proc Natl Acad Sci USA.* 2003 Apr. 29; 100(9):5022-7). In addition, production of human glycoproteins with complex N-glycans lacking galactose through re-engineering the secretory pathway in yeast *P. pastoris* has been shown (Hamilton et al., *Science*. 2003 Aug. 29; 301(5637):1244-6). In mammalian cells, further maturation involves galactose transfer. Consequently, the maturation of complex glycosylation pathways from yeast and lower eukaryotes requires the functional expression of β1,4-galactosyltransferase.

Recombinant expression of UDP-Gal: βGlcNAc β1,4-galactosyltransferase (β1,4GalT) has been demonstrated in mammalian cells, insect cells (e.g., Sf-9) and yeast cells. A cDNA encoding a soluble form of the human β1,4-galactosyltransferase I (EC 2.4.1.22) (lacking the endogenous Type II membrane domain) has also been expressed in the methylotrophic yeast *P. pastoris*. Malissard et al. *Biochem Biophys Res Commun*. 2000 Jan. 7; 267(1):169-73. Additionally, gene fusions encoding ScMnt1p fused to the catalytic domain of a human β1,4-galactosyltransferase (Gal-Tf) have been expressed showing some activity of the enzyme in the yeast Golgi albeit at very low conversion efficiency. Schwientek et al., *J Biol. Chem.* 1996 Feb. 16; 271(7):3398-405. Thus, targeting a β1,4-galactosyltranferase (β1,4GalT) to the secretory pathway of a host that produces glycans containing terminal GlcNAc is expected to result in some galactose transfer. However the formation of complex glycans in higher eukaryotes involves the action of mannosidase II which in mammalian cells has been found to act in competition with GalTI (Fukuta et al., *Arch Biochem Biophys*. 2001 Aug. 1; 392(1): 79-86). The premature action of GalT is thus expected to prevent the formation of complex galactosylated glycoproteins in the secretory pathway and yield mostly hybrid glycans.

The N-glycans of mammalian glycoproteins typically include galactose, fucose, and terminal sialic acid. These sugars are not usually found on glycoproteins produced in yeast and filamentous fungi. In humans, nucleotide sugar precursors (e.g. UDP-N-acetylglucosamine, UDP-N-acetylgalactosamine, CMP-N-acetylneuraminic acid, UDP-galactose, GDP-fucose, etc.) are synthesized in the cytosol and transported into the Golgi, where they are incorporated into N-glycans by glycosyltransferases (Sommers and Hirschberg, 1981 *J. Cell Biol.* 91(2): A406-A406; Sommers and Hirschberg 1982 *J. Biol. Chem.* 257(18): 811-817; Perez and Hirschberg 1987 *Methods in Enzymology* 138: 709-715).

Glycosylation engineering in heterologous protein expression systems may involve expression of various enzymes that are involved in the synthesis of nucleotide sugar precursors. The enzyme UDP-galactose 4-epimerase converts the sugar nucleotide UDP-glucose to UDP-galactose via an epimerization of C4. The enzyme has been found in organisms that are able to use galactose as its sole carbon source. Recently, the bifunctional enzyme, Gal10p, has been purified in *Saccharomyces cerevisiae* having both a UDP-glucose 4-epimerase and aldose 1-epimerase activity. Majumdar et al., *Eur J. Biochem.* 2004 February; 271(4):753-759.

The UDP-galactose transporters (UGT) transport UDP-galactose from the cytosol to the lumen of the Golgi. Two heterologous genes, gma12(+) encoding alpha 1,2-galactosyltransferase (alpha 1,2 GalT) from *Schizosaccharomyces pombe* and (hUGT2) encoding human UDP-galactose transporter, have been functionally expressed in *S. cerevisiae* to examine the intracellular conditions required for galactosylation. Correlation between protein galactosylation and UDP-galactose transport activity indicated that an exogenous supply of UDP-Gal transporter, played a key role for efficient galactosylation in *S. cerevisiae* (Kainuma, 1999 *Glycobiology* 9(2): 133-141). Likewise, a UDP-galactose transporter from *S. pombe* was cloned (Aoki, 1999 *J. Biochem.* 126(5): 940-950; Segawa, 1999 *Febs Letters* 451(3): 295-298).

Glycosyltransfer reactions typically yield a side product which is a nucleoside diphosphate or monophosphate. While monophosphates can be directly exported in exchange for nucleoside diphosphate sugars by an antiport mechanism, diphosphonucleosides (e.g. GDP) have to be cleaved by phosphatases (e.g. GDPase) to yield nucleoside monophosphates and inorganic phosphate prior to being exported. This reaction is important for efficient glycosylation; for example, GDPase from *S. cerevisiae* has been found to be necessary for mannosylation. However that GDPase has 90% reduced activity toward UDP (Berninsone et al., 1994 *J. Biol. Chem.* 269(1):207-211). Lower eukaryotes typically lack UDP-specific diphosphatase activity in the Golgi since they do not utilize UDP-sugar precursors for Golgi-based glycoprotein synthesis. *S. pombe*, a yeast found to add galactose residues to cell wall polysaccharides (from UDP-galactose) has been found to have specific UDPase activity, indicating the potential requirement for such an enzyme (Berninsone et al., 1994).

UDP is known to be a potent inhibitor of glycosyltransferases and the removal of this glycosylation side product may be important to prevent glycosyltransferase inhibition in the lumen of the Golgi (Khatara et al., 1974). See Berninsone, P., et al. 1995. *J. Biol. Chem.* 270(24): 14564-14567; Beaudet, L., et al. 1998 *Abc Transporters: Biochemical, Cellular, and Molecular Aspects.* 292: 397-413.

What is needed, therefore, is a method to catalyze the transfer of galactose residues from a sufficient pool of UDP-galactose onto preferred acceptor substrates for use as therapeutic glycoproteins.

SUMMARY OF THE INVENTION

The present invention provides a novel lower eukaryotic host cell producing human-like glycoproteins characterized as having a terminal galactose residue and essentially lacking fucose and sialic acid residues on the glycoprotein. In one embodiment, the present invention provides a recombinant lower eukaryotic host cell producing human-like glycoproteins, the host comprising an isolated nucleic acid molecule encoding β-galactosyltransferase activity and at least an isolated nucleic acid molecule encoding UDP-galactose transport activity, UDP-galactose C4 epimerase activity, galactokinase activity or galactose-1-phosphate uridyl transferase. The present invention also provides a recombinant lower eukaryotic host cell producing human-like glycoproteins, the host cell capable of transferring β-galactose residue onto an N-linked oligosaccharide branch of a glycoprotein comprising a terminal GlcNAc residue, the N-linked oligosaccharide branch selected from the group consisting of GlcNAcβ1,2-Manα1,3; GlcNAcβ1,4-Manα1,3; GlcNAcβ1,2-Manα1,6; GlcNAcβ1,4-Manα1,6; and GlcNAcβ1,6-Manα1,6 on a tri-mannose core. In another embodiment, the present invention provides a recombinant lower eukaryotic host cell that produces glycoproteins that are acceptor substrates for sialic acid transfer.

In another aspect of the invention, herein is provided a composition comprising a human-like glycoprotein characterized as having a terminal β-galactose residue and essentially lacking fucose and sialic acid residues on the glycoprotein. In one embodiment, the glycoprotein comprises N-linked oligosaccharides selected from the group consisting of: GalGlcNAcMan$_3$GlcNAc$_2$, GalGlcNAc$_2$Man$_3$GlcNAc$_2$, Gal$_2$GlcNAc$_2$Man$_3$GlcNAc$_2$, GalGlcNAc$_3$Man$_3$GlcNAc$_2$, Gal$_2$GlcNAc$_3$Man$_3$GlcNAc$_2$, Gal$_3$GlcNAc$_3$Man$_3$GlcNAc$_2$, GalGlcNAc$_4$Man$_3$GlcNAc$_2$, Gal$_2$GlcNAc$_4$Man$_3$GlcNAc$_2$, Gal$_3$GlcNAc$_4$Man$_3$GlcNAc$_2$, Gal$_4$GlcNAc$_4$Man$_3$GlcNAc$_2$ GalGlcNAcMan$_5$GlcNAc$_2$, GalGlcNAc$_2$Man$_5$GlcNAc$_2$, Gal$_2$GlcNAc$_2$Man$_5$GlcNAc$_2$, GalGlcNAc$_3$Man$_5$GlcNAc$_2$, Gal$_2$GlcNAc$_3$Man$_5$GlcNAc$_2$ and Gal$_3$GlcNAc$_3$Man$_5$GlcNAc$_2$.

In another embodiment, a method is provided for producing human-like glycoproteins in a lower eukaryotic host cell the method comprising the step of producing UDP-galactose above endogenous levels.

In yet another embodiment, a method is provided for producing human-like glycoprotein composition in lower eukaryotic host cell comprising the step of transferring a galactose residue on a hybrid or complex glycoprotein in the absence of fucose and sialic acid residues.

In accordance with the methods of the present invention, at least 10%, preferably 33%, more preferably 60% or greater galactosylated glycoprotein composition is produced.

The present invention further provides a recombinant lower eukaryotic host cell expressing GalNAc Transferase activity.

The present invention also provides a recombinant lower eukaryotic host cell expressing a gene encoding heterologous UDPase activity.

Additionally, the present invention provides an isolated polynucleotide comprising or consisting of a nucleic acid sequence selected from the group consisting of:

(a) SEQ ID NO: 14;
(b) at least about 90% similar to the amino acid residues of the donor nucleotide binding site of SEQ ID NO: 13;
(c) a nucleic acid sequence at least 92%, at least 95%, at least 98%, at least 99% or at least 99.9% identical to SEQ ID NO: 14;
(d) a nucleic acid sequence that encodes a conserved polypeptide having the amino acid sequence of SEQ ID NO: 13;
(e) a nucleic acid sequence that encodes a polypeptide at least 78%, at least 80%, at least 85%, at least 90%, at least 95%, at least 98%, at least 99% or at least 99.9% identical to SEQ ID NO:13;
(f) a nucleic acid sequence that hybridizes under stringent conditions to SEQ ID NO:14; and
(g) a nucleic acid sequence comprising a fragment of any one of (a)-(f) that is at least 60 contiguous nucleotides in length.

Herein is also provided a modified polynucleotide comprising or consisting of a nucleic acid sequence selected from the group consisting of the conserved regions of SEQ ID NO: 49-SEQ ID NO: 53 wherein the encoded polypeptide is involved in catalyzing the interconversion of UDP-glucose and UDP-galactose for production of galactosylated glycoproteins.

BRIEF DESCRIPTION OF THE DRAWINGS

FIG. 6A depicts the amino acid sequence of SpGalE (SEQ ID NO: 13). FIG. 6B depicts the coding sequence of SpGALE (SEQ ID NO: 14).

FIG. 7 shows a sequence alignment of *S. pombe*, human, *E. coli* and *S. cerevisiae* epimerases (SEQ ID NOS 64-67).

DETAILED DESCRIPTION OF THE INVENTION

Figure 1A:
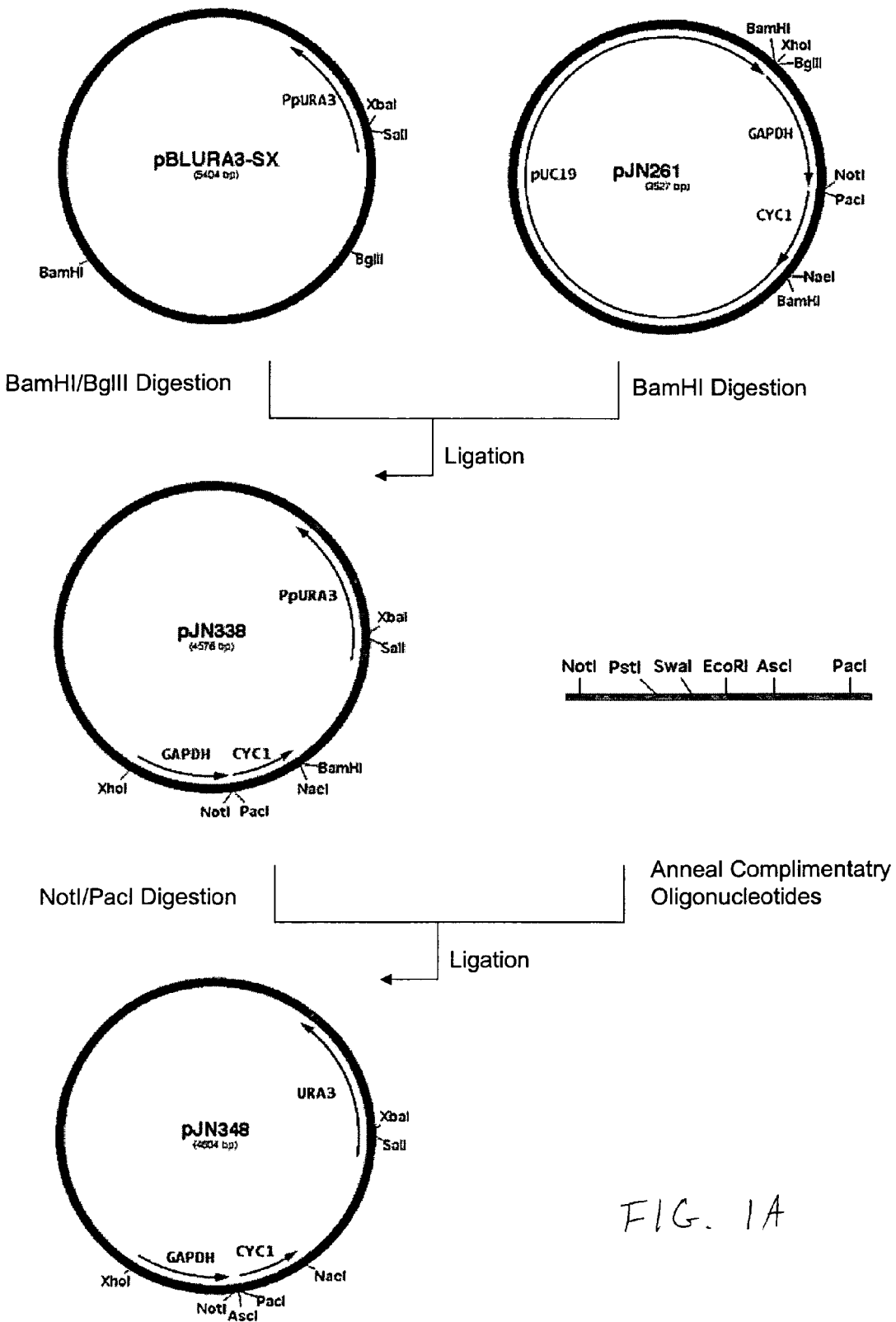
FIGS. 1A-1B depicts the construction of a plasmid map of the integration vector pXB53 encoding hGalTI.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The methods and techniques of the present invention are generally performed according to conventional methods well known in the art. Generally, nomenclatures used in connection with, and techniques of biochemistry, enzymology, molecular and cellular biology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lane Antibodies: A Laboratory Manual Cold Spring Harbor Laboratory Press, Cold Spring Harbor, N.Y. (1990); Introduction to Glycobiology, Maureen E. Taylor, Kurt Drickamer, Oxford Univ. Press (2003); Worthington Enzyme Manual, Worthington Biochemical Corp. Freehold, N.J.; Handbook of Biochemistry: Section A Proteins Vol I 1976 CRC Press; Handbook of Biochemistry: Section A Proteins Vol II 1976 CRC Press; Essentials of Glycobiology, Cold Spring Harbor Laboratory Press (1999). The nomenclatures used in connection with, and the laboratory procedures and techniques of, biochemistry and molecular biology described herein are those well known and commonly used in the art.

All publications, patents and other references mentioned herein are incorporated by reference.

The following terms, unless otherwise indicated, shall be understood to have the following meanings:

As used herein, the term "K3" refers to the kringle 3 domain of human plasminogen.

As used herein, the term "N-glycan" refers to an N-linked oligosaccharide, e.g., one that is attached by an asparagine-N-acetylglucosamine linkage to an asparagine residue of a polypeptide. N-glycans have a common pentasaccharide core of $Man_3GlcNAc_2$ ("Man" refers to mannose; "Glc" refers to glucose; and "NAc" refers to N-acetyl; GlcNAc refers to N-acetylglucosamine). N-glycans differ with respect to the number of branches (antennae) comprising peripheral sugars (e.g., GlcNAc, galactose, fucose and sialic acid) that are added to the $Man_3GlcNAc_2$ ("Man3") core structure. N-glycans are classified according to their branched constituents (e.g., high mannose, complex or hybrid). A "high mannose" type N-glycan has five or more mannose residues. A "complex" type N-glycan typically has at least one GlcNAc attached to the 1,3 mannose arm and at least one GlcNAc attached to the 1,6 mannose arm of a "trimannose" core. The "trimannose core" is the pentasaccharide core having a Man3 structure. It is often referred to as "paucimannose" structure. Complex N-glycans may also have galactose ("Gal") residues that are optionally modified with sialic acid or derivatives ("NeuAc", where "Neu" refers to neuraminic acid and "Ac" refers to acetyl). Complex N-glycans may also have intrachain substitutions comprising "bisecting" GlcNAc and core fucose ("Fuc"). Complex N-glycans may also have multiple antennae on the "trimannose core," often referred to as "multiple antennary glycans." A "hybrid" N-glycan has at least one GlcNAc on the terminal of the 1,3 mannose arm of the trimannose core and zero or more mannoses on the 1,6 mannose arm of the trimannose core.

Abbreviations used herein are of common usage in the art, see, e.g., abbreviations of sugars, above. Other common abbreviations include "PNGase", which refers to peptide N-glycosidase F (EC 3.2.2.18); "GalT", which refers to Galactosyl transferase, "β1,4GalT", which refers to UDP-galactose: β-N-acetylglucosamine β1,4-galactosyltransferase. β-Galactosyltransferases from various species are abbreviated as follows: "hGalT" refers to human β1,4-galactosyltransferase, "bGalT" refers to bovine β1,4-galactosyltransferase, "XlGalT" refers to Xenopus leavis β1,4-galactosyltransferase and "CeGalT" refers to C. elegans β1,4-galactosyltransferase. "GalNAcT" refers to UDP-GalNAc-GlcNAc β-1,4-N-acetylgalactosaminyltransferase.

As used herein, the term "UGT" refers to UDP-galactose transporter. The term "SpGalE" refers to S. pombe UDP-galactose 4-epimerase, "hGalE" refers to human UDP-galactose 4-epimerase, "ScGal10" refer to S. cerevisiae UDP-galactose 4-epimerase and "EcGalE" refers to E. coli UDP-galactose 4-epimerase.

As used herein, the term "UDP-Gal" refers to UDP-galactose and the term "UDP-GalNAc" refers to UDP-N-acetylgalactosamine.

N-linked glycoproteins contain an N-acetylglucosamine residue linked to the amide nitrogen of an asparagine residue in the protein. The predominant sugars found on glycoproteins are glucose, galactose, mannose, fucose, N-acetylgalactosamine (GalNAc), N-acetylglucosamine (GlcNAc) and sialic acid (e.g., N-acetyl-neuraminic acid (NANA)). The processing of the sugar groups occurs cotranslationally in the lumen of the ER and continues in the Golgi apparatus for N-linked glycoproteins.

As used herein, the term "human-like" glycoprotein refers to modified N-glycans covalently attached to a protein that are similar to the glycoproteins found in the human N-linked oligosaccharide synthesis. Complex and hybrid N-glycans are intermediates found in human glycosylation. Common to these intermediates is the $Man_3GlcNAc_2$ core structure also referred to as the paucimannose core, pentasaccharide core or simply Man3 or $Man_3$. Human-like glycoproteins, therefore, have at least the Man3 core structure.

As used herein, the term "initiating 1,6 mannosyltransferase activity" refers to a yeast specific glycan residues typically added to the Manα1,3 arm of the trimannose core in outer chain formation initiated by Och1p with an α1,6 linkage.

The mole % transfer of galactose residue onto N-glycans as measured by MALDI-TOF-MS in positive mode refers to mole % galactose transfer with respect to mole % total neutral N-glycans. Certain cation adducts such as $K^+$ and $Na^+$ are normally associated with the peaks eluted increasing the mass of the N-glycans by the molecular mass of the respective adducts.

As used herein, the term "secretion pathway" refers to the assembly line of various glycosylation enzymes to which a lipid-linked oligosaccharide precursor and an N-glycan substrate are sequentially exposed, following the molecular flow of a nascent polypeptide chain from the cytoplasm to the endoplasmic reticulum (ER) and the compartments of the Golgi apparatus. Enzymes are said to be localized along this pathway. An enzyme X that acts on a lipid-linked glycan or an N-glycan before enzyme Y is said to be or to act "upstream" to enzyme Y; similarly, enzyme Y is or acts "downstream" from enzyme X.

As used herein, the term "mutation" refers to any change in the nucleic acid or amino acid sequence of a gene product, e.g., of a glycosylation-related enzyme.

The term "polynucleotide" or "nucleic acid molecule" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation. The term includes single and double stranded forms of DNA.

Unless otherwise indicated, a "nucleic acid comprising SEQ ID NO:X" refers to a nucleic acid, at least a portion of which has either (i) the sequence of SEQ ID NO:X, or (ii) a sequence complementary to SEQ ID NO:X. The choice between the two is dictated by the context. For instance, if the nucleic acid is used as a probe, the choice between the two is dictated by the requirement that the probe be complementary to the desired target.

An "isolated" or "substantially pure" nucleic acid or polynucleotide (e.g., an RNA, DNA or a mixed polymer) is one which is substantially separated from other cellular components that naturally accompany the native polynucleotide in its natural host cell, e.g., ribosomes, polymerases, and genomic sequences with which it is naturally associated. The term embraces a nucleic acid or polynucleotide that (1) has been removed from its naturally occurring environment, (2) is not associated with all or a portion of a polynucleotide in which the "isolated polynucleotide" is found in nature, (3) is operatively linked to a polynucleotide which it is not linked to in nature, or (4) does not occur in nature. The term "isolated" or "substantially pure" also can be used in reference to recombinant or cloned DNA isolates, chemically synthesized polynucleotide analogs, or polynucleotide analogs that are biologically synthesized by heterologous systems.

However, "isolated" does not necessarily require that the nucleic acid or polynucleotide so described has itself been physically removed from its native environment. For instance, an endogenous nucleic acid sequence in the genome of an organism is deemed "isolated" herein if a heterologous sequence (i.e., a sequence that is not naturally adjacent to this endogenous nucleic acid sequence) is placed adjacent to the endogenous nucleic acid sequence, such that the expression of this endogenous nucleic acid sequence is altered. By way of example, a non-native promoter sequence can be substituted (e.g., by homologous recombination) for the native promoter of a gene in the genome of a human cell, such that this gene has an altered expression pattern. This gene would now become "isolated" because it is separated from at least some of the sequences that naturally flank it.

A nucleic acid is also considered "isolated" if it contains any modifications that do not naturally occur to the corresponding nucleic acid in a genome. For instance, an endogenous coding sequence is considered "isolated" if it contains an insertion, deletion or a point mutation introduced artificially, e.g., by human intervention. An "isolated nucleic acid" also includes a nucleic acid integrated into a host cell chromosome at a heterologous site, a nucleic acid construct present as an episome. Moreover, an "isolated nucleic acid" can be substantially free of other cellular material, or substantially free of culture medium when produced by recombinant techniques, or substantially free of chemical precursors or other chemicals when chemically synthesized.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences (Pearson, 1990, (herein incorporated by reference). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 50%, more preferably 60% of the nucleotide bases, usually at least about 70%, more usually at least about 80%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook et al., supra, page 9.51, hereby incorporated by reference. For purposes herein, "high stringency conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

The nucleic acids (also referred to as polynucleotides) of this invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The term "mutated" when applied to nucleic acid sequences means that nucleotides in a nucleic acid sequence may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product. See, e.g., Leung, D. W., et al., *Technique*, 1, pp. 11-15 (1989) and Caldwell, R. C. & Joyce G. F., *PCR Methods Applic.*, 2, pp. 28-33 (1992)); and "oligonucleotide-directed mutagenesis" (a process which enables the generation of site-specific mutations in any cloned DNA segment of interest. See, e.g., Reidhaar-Olson, J. F. & Sauer, R. T., et al., *Science*, 241, pp. 53-57 (1988)).

The term "vector" as used herein is intended to refer to a nucleic acid molecule capable of transporting another nucleic acid to which it has been linked. One type of vector is a "plasmid", which refers to a circular double stranded DNA loop into which additional DNA segments may be ligated. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply, "expression vectors").

"Operatively linked" expression control sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "recombinant lower eukaryotic host cell" (or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism. A recombinant host cell includes yeast, fungi, collar-flagellates, microsporidia, alveolates (e.g., dinoflagellates), stramenopiles (e.g, brown algae, protozoa), rhodophyta (e.g., red algae), plants (e.g., green algae, plant cells, moss) and other protists.

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "polypeptide" encompasses both naturally-occurring and non-naturally-occurring proteins, and fragments, mutants, derivatives and analogs thereof. A polypeptide may be monomeric or polymeric. Further, a polypeptide may comprise a number of different domains each of which has one or more distinct activities.

The term "isolated protein" or "isolated polypeptide" is a protein or polypeptide that by virtue of its origin or source of derivation (1) is not associated with naturally associated components that accompany it in its native state, (2) when it exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from its native environment.

The term "polypeptide fragment" as used herein refers to a polypeptide that has an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A "modified derivative" refers to polypeptides or fragments thereof that are substantially homologous in primary structural sequence but which include, e.g., in vivo or in vitro chemical and biochemical modifications or which incorporate amino acids that are not found in the native polypeptide. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{125}$I, $^{32}$P, $^{35}$S, and $^3$H, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well known in the art. See Ausubel et al., 1992, hereby incorporated by reference.

The term "fusion protein" refers to a polypeptide comprising a polypeptide or fragment coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

The term "non-peptide analog" refers to a compound with properties that are analogous to those of a reference polypeptide. A non-peptide compound may also be termed a "peptide mimetic" or a "peptidomimetic". See, e.g., Jones, (1992) Amino Acid and Peptide Synthesis, Oxford University Press; Jung, (1997) Combinatorial Peptide and Nonpeptide Libraries: A Handbook John Wiley; Bodanszky et al., (1993) Peptide Chemistry—A Practical Textbook, Springer Verlag; "Synthetic Peptides: A Users Guide", G. A. Grant, Ed, W. H. Freeman and Co., 1992; Evans et al. *J. Med. Chem.* 30:1229 (1987); Fauchere, *J. Adv. Drug Res.* 15:29 (1986); Veber and Freidinger *TINS* p. 392 (1985); and references sited in each of the above, which are incorporated herein by reference. Such compounds are often developed with the aid of computerized molecular modeling. Peptide mimetics that are structurally similar to useful peptides of the invention may be used to produce an equivalent effect and are therefore envisioned to be part of the invention.

A "polypeptide mutant" or "mutein" refers to a polypeptide whose sequence contains an insertion, duplication, deletion, rearrangement or substitution of one or more amino acids compared to the amino acid sequence of a native or wild type protein. A mutein may have one or more amino acid point substitutions, in which a single amino acid at a position has been changed to another amino acid, one or more insertions and/or deletions, in which one or more amino acids are inserted or deleted, respectively, in the sequence of the naturally-occurring protein, and/or truncations of the amino acid sequence at either or both the amino or carboxy termini. A mutein may have the same but preferably has a different biological activity compared to the naturally-occurring protein.

A mutein has at least 70% overall sequence homology to its wild-type counterpart. Even more preferred are muteins having 80%, 85% or 90% overall sequence homology to the wild-type protein. In an even more preferred embodiment, a mutein exhibits 95% sequence identity, even more preferably 97%, even more preferably 98% and even more preferably 99%, 99.5% or 99.9% overall sequence identity. Sequence homology may be measured by any common sequence analysis algorithm, such as Gap or Bestfit.

Preferred amino acid substitutions are those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs.

As used herein, the twenty conventional amino acids and their abbreviations follow conventional usage. See *Immunology—A Synthesis* (2$^{nd}$ Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, s-N-methylarginine, and other similar amino acids and imino acids (e.g., 4-hydroxyproline). In the polypeptide notation used herein, the left-hand direction is the amino terminal direction and the right hand direction is the carboxy-terminal direction, in accordance with standard usage and convention.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences). In a preferred embodiment, a homologous protein is one that exhibits 60% sequence homology to the wild type protein, more preferred is 70% sequence homology. Even more preferred are homologous proteins that exhibit 80%, 85% or 90% sequence homology to the wild type protein. In a yet more preferred embodiment, a homologous protein exhibits 95%, 97%, 98% or 99% sequence identity. As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson et al., 1994, herein incorporated by reference).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1.

A preferred algorithm when comparing a inhibitory molecule sequence to a database containing a large number of sequences from different organisms is the computer program BLAST (Altschul, S. F. et al. (1990) *J. Mol. Biol.* 215:403-410; Gish and States (1993) *Nature Genet.* 3:266-272; Madden, T. L. et al. (1996) *Meth. Enzymol.* 266:131-141; Altschul, S. F. et al. (1997) *Nucleic Acids Res.* 25:3389-3402; Zhang, J. and Madden, T. L. (1997) *Genome Res.* 7:649-656), especially blastp or tblastn (Altschul et al., 1997). Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences (Pearson, 1990, herein incorporated by reference). For example, percent sequence identity between amino acid sequences can be determined using FASTA with its default parameters (a word size of 2 and the PAM250 scoring matrix), as provided in GCG Version 6.1, herein incorporated by reference.

The term "domain" as used herein refers to a structure of a biomolecule that contributes to a known or suspected function of the biomolecule. Domains may be co-extensive with regions or portions thereof; domains may also include distinct, non-contiguous regions of a biomolecule. Examples of protein domains include, but are not limited to, an Ig domain, an extracellular domain, a transmembrane domain, and a cytoplasmic domain.

As used herein, the term "molecule" means any compound, including, but not limited to, a small molecule, peptide, protein, sugar, nucleotide, nucleic acid, lipid, etc., and such a compound can be natural or synthetic.

Throughout this specification and its embodiments, the word "comprise" or variations such as "comprises" or "comprising", will be understood to refer to the inclusion of a stated integer or group of integers but not the exclusion of any other integer or group of integers.

Unless otherwise defined, all technical and scientific terms used herein have the same meaning as commonly understood by one of ordinary skill in the art to which this invention pertains. Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting.

Engineering Hosts to Produce Human-Like Galactosylated Glycoproteins

The present invention provides a recombinant lower eukaryotic host cell producing human-like glycoproteins wherein the glycoproteins are characterized as having a terminal β-galactose residue and essentially lacking fucose and sialic acid. In one embodiment, the present invention provides a lower eukaryotic host cell comprising an isolated nucleic acid molecule encoding UDP-galactose: β-N-acetylglucosamine β1,4-galactosyltransferase (β1,4GalT) in combination with at least a second isolated nucleic acid molecule encoding a UDP-galactose transporter, an isolated nucleic acid encoding a UDP-galactose 4-epimerase, an isolated nucleic acid encoding galactokinase or a galactose-1-phosphate uridyl transferase. In another embodiment, β1,4GalT is expressed in combination with an isolated nucleic acid molecule encoding a UDP-galactose transporter and an isolated nucleic acid molecule encoding a UDP-galactose 4-epimerase. Variants and fragments of the nucleic acid sequences encoding the above enzymes, recombinant DNA molecules and expression vectors comprising the enzymes for transformation are also provided.

In one aspect of the present invention, a method is provided to produce a human-like glycoprotein in a lower eukaryotic host cell comprising the step of catalyzing the transfer of a galactose residue from UDP-galactose onto an acceptor substrate in a β-linkage by expression of a β1,4GalT activity and introducing into the host a UDP-galactose 4-epimerase activity, galactokinase activity, a galactose-1-phosphate uridyl transferase activity or a UDP-galactose transport activity. The acceptor substrate is preferably an oligosaccharide composition comprising a terminal GlcNAc residue, for example, GlcNAcβ1,2-Manα1,3; GlcNAcβ1,4-Manα1,3; GlcNAcβ1,2-Manα1,6; GlcNAcβ1,4-Manα1,6; or GlcNAcβ1,6-Manα1,6 branch on a trimannose core.

The acceptor substrate is more preferably a complex glycan (e.g., GlcNAc$_2$Man$_3$GlcNAc$_2$), a hybrid glycan (e.g., GlcNAcMan$_5$GlcNAc$_2$) or a multiple antennary glycan (e.g., GlcNAc$_4$Man$_3$GlcNAc$_2$) that is covalently linked (N-linked) to a protein of interest. The β-galactose residue is transferred onto the acceptor substrate comprising a hydroxy group at carbon 4 of 2-acetamido-2-deoxy-D-glucose (GlcNAc) forming a β-glycosidic linkage. The N-linked acceptor substrates comprising a terminal GlcNAc residue capable of accepting a galactose residue include, without limitation, GlcNAcMan₃GlcNAc₂, GlcNAc₂Man₃GlcNAc₂, GlcNAc₃Man₃GlcNAc₂, GlcNAc₄Man₃GlcNAc₂, GlcNAc₅Man₃GlcNAc₂ GlcNAc₆Man₃GlcNAc₂, GlcNAcMan₄GlcNAc₂, GlcNAcMan₅GlcNAc₂, GlcNAc₂Man₅GlcNAc₂ and GlcNAc₃Man₅GlcNAc₂.

Cloning of β1,4-Galactosyltransferase Genes

Figure 1B:
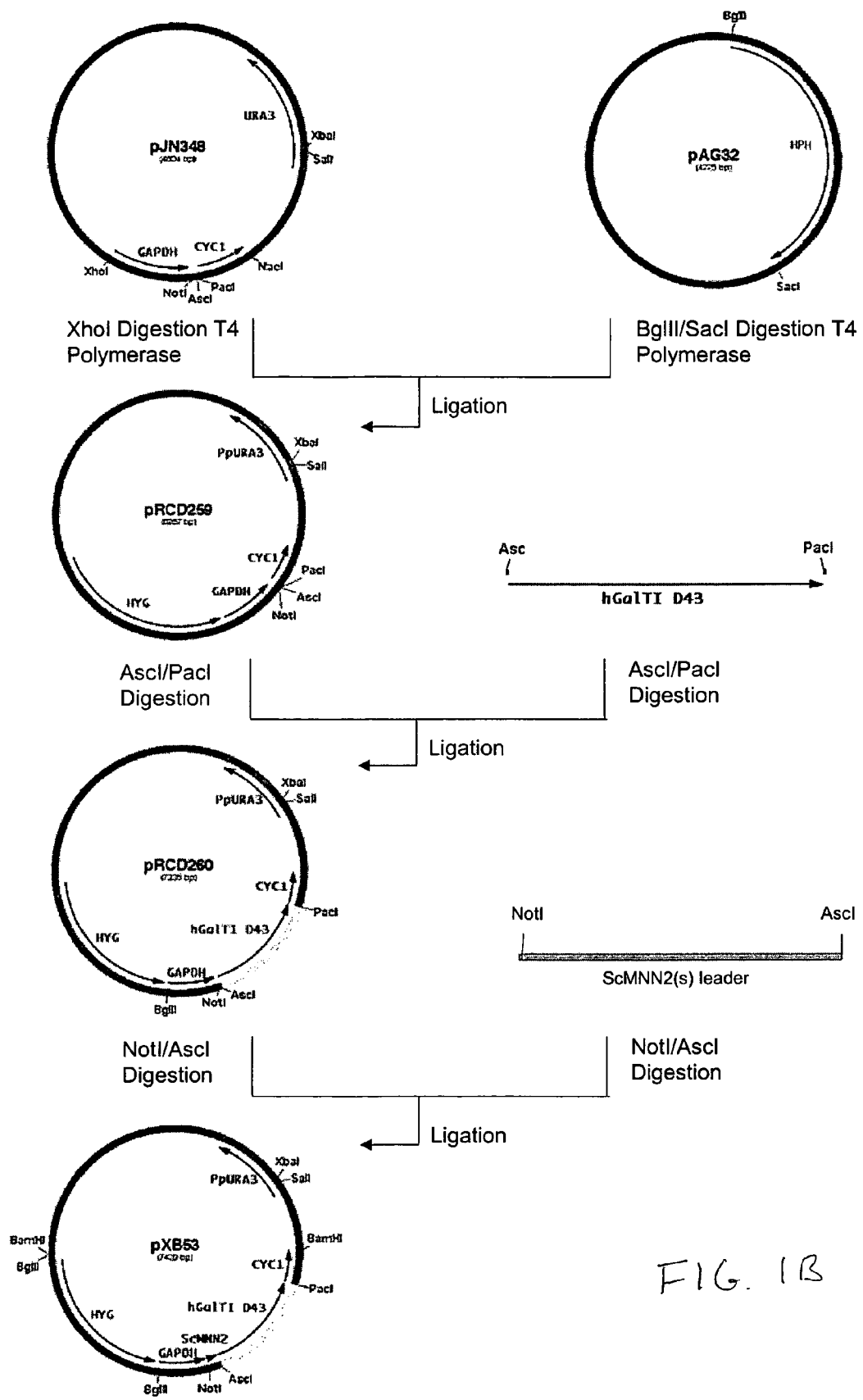
Figure 2:
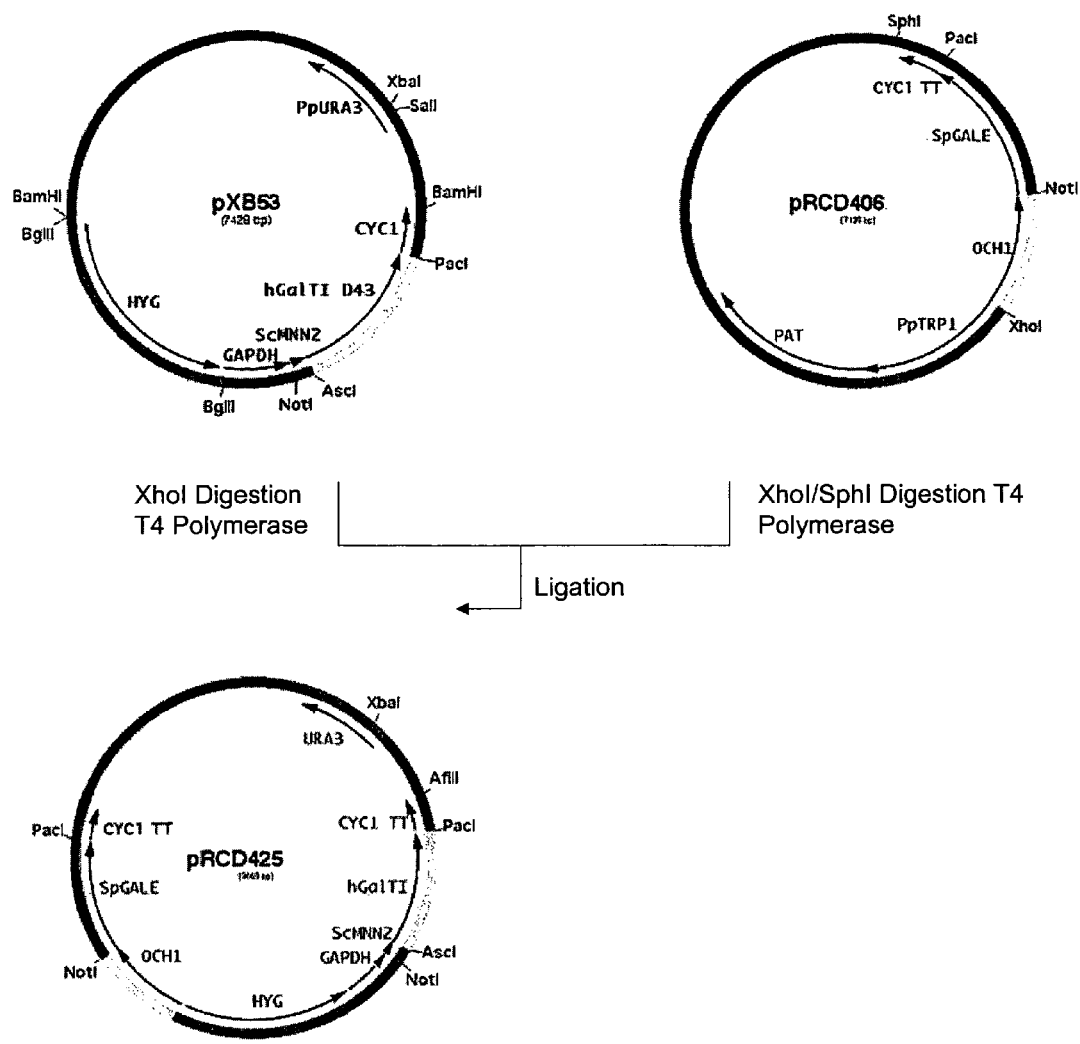
FIG. 2 depicts the construction of a plasmid map of the integration vector pRCD425 encoding the *S. pombe* Gal epimerase (SpGalE) and hGalTI.

The human β-1,4-galactosyltransferase I gene (hGalTI, Genbank AH003575) was PCR amplified from human kidney cDNA (marathon ready cDNA, Clontech) using primers RCD192 (SEQ ID NO:1) and RCD186 (SEQ ID NO:2). This PCR product was cloned in pCR2.1 (Invitrogen) cloned and sequenced. From this clone, a PCR overlap mutagenesis was performed. The 5' end of the gene up to the NotI site was amplified using primers RCD198 (SEQ ID NO:3) and RCD201 (SEQ ID NO:4) and the 3' end was amplified with primers RCD200 (SEQ ID NO:5) and RCD199 (SEQ ID NO:6). The products were overlapped together with primers RCD198 (SEQ ID NO:3) and RCD199 (SEQ ID NO:6) to resynthesize the ORF with the wild-type amino acid (except for an N-terminal deletion of 43 amino acids) sequence while eliminating the NotI site. The new truncated hGalTI PCR product was cloned in pCR2.1 and sequenced. The introduced AscI/PacI sites were then used to subclone the fragment into plasmid pRCD259 (FIG. 1), a PpURA3/HYG$^R$ roll-in vector creating pRCD260 (FIG. 1) (Example 4).

The same strategy was applied in cloning the human β1,4GalTII and the human β1,4GalTIII. Example 4 describes using gene-specific primers to amplify the human β1,4-galactosyltransferase II and III genes by PCR and cloning it then into a vector.

Expression of β1,4-Galactosyltransferase Activity in a Lower Eukaryote

A gene encoding β1,4GalT activity or a recombinant nucleic acid molecule encoding β1,4-galactosyltransferase activity, a gene fusion encoding β1,4GalT activity (e.g., pXB53) (FIG. 1) or expression from a nucleic acid molecule encoding β1,4-galactosyltransferase (Genbank AH003575) is introduced and expressed in a lower eukaryotic host cell (e.g. P. pastoris) to produce galactosylated glycoproteins. Alternatively, by activation of a β-galactosyltransferase activity, a lower eukaryotic host cell is engineered to produce galactosylated glycoforms. A catalytically active β1,4-galactosyltransferase domain or a part thereof catalyzes the transfer of a galactose residue from UDP-galactose onto the terminal GlcNAc residue of an oligosaccharide acceptor substrate (e.g. GlcNAc₂Man₃GlcNAc₂) forming a β1,4Gal glycosidic linkage. Complex galactosylated N-glycans that are produced according to the present invention essentially lack fucose and sialic acid (e.g., Gal₂GlcNAc₂Man₃GlcNAc₂). Such a glycoprotein composition comprising complex galactosylated, afucosylated and asialylated N-glycans are useful as therapeutic agents.

The newly formed substrates are also preferable precursors in the formation of sialylated glycoproteins produced in a lower eukaryotic host. The present invention, thus provides a method for producing human-like glycoproteins wherein the glycoproteins are characterized as having a terminal galactose residues that are acceptor substrates for the transfer of sialic acid in a lower eukaryote.

Combinatorial DNA Library of β1,4-Galactosyltransferase

In a related aspect of the invention, a combinatorial DNA library of β1,4-galactosyltransferase and yeast targeting sequence transmembrane domains is created and expressed in a lower eukaryotic host cell as described in WO 02/00879.

Accordingly, a sub-library of hGalTI (e.g. Genbank Accession No. X55415) fused to a sub-library of targeting peptides of lengths: short, medium and long as described in WO 02/00879 is generated. The targeting peptide sub-library includes nucleic acid sequences encoding targeting signal peptides that result in localization of a protein to a particular location within the ER, Golgi, or trans Golgi network. These targeting peptides may be selected from the host organism to be engineered as well as from other related or unrelated organisms. Generally such sequences fall into three categories: (1) N-terminal sequences encoding a cytosolic tail (ct), a transmembrane domain (tmd) and part or all of a stem region (sr), which together or individually anchor proteins to the inner (lumenal) membrane of the Golgi; (2) retrieval signals which are generally found at the C-terminus such as the HDEL (SEQ ID NO: 69) or KDEL (SEQ ID NO: 70) tetrapeptide; and (3) membrane spanning regions from various proteins, e.g., nucleotide sugar transporters, which are known to localize in the Golgi.

The targeting peptides are indicated herein as short (s), medium (m) and long (l) relative to the parts of a type II membrane protein. The targeting peptide sequence indicated as short (s) corresponds to the transmembrane domain (tmd) of the membrane-bound protein. The targeting peptide sequence indicated as long (l) corresponds to the length of the transmembrane domain (tmd) and the stem region (sr). The targeting peptide sequence indicated as medium (m) corresponds to the transmembrane domain (tmd) and approximately half the length of the stem region (sr). The catalytic domain regions are indicated herein by the number of nucleotide deletion with respect to its wild-type glycosylation enzyme.

In one embodiment, the library was transformed into P. pastoris and the transformants were selected on minimal medium containing hygromycin. The activity of β1,4-galactosyltransferase I fused to various leader sequences (as described below) was analyzed via production of galactosylated N-glycans as a readout using MALDI-TOF MS in positive mode.

β-Galactosyltransferase Fusion Constructs

A library of the isolated yeast targeting sequence transmembrane domains (consisting of 48 leader sequences (WO 02/00879)) was ligated into the NotI/AscI sites on pRCD260 located upstream of the hGalTI gene to create plasmids pXB20-pXB67 (each plasmid carrying one leader sequence).

Figure 9A:
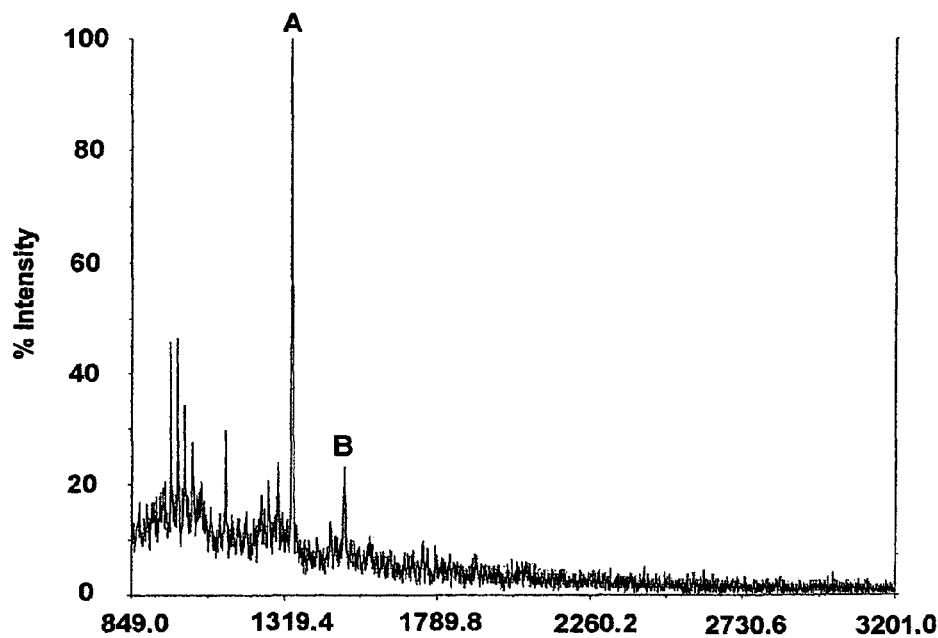
FIG. 9A is a MALDI-TOF-MS analysis of N-glycans released from K3 produced in YSH-44 transformed with pXB53 displaying a peak at 1501 m/z [B], which corresponds to the mass of the N-glycan $GalGlcNAc_2Man_3GlcNAc_2$ and a peak at 1339 m/z [A], which corresponds to the mass of $GlcNAc_2Man_3GlcNAc_2$.

A representative example of a GalT fusion construct derived from a combinatorial DNA library of the invention is pXB53 (FIG. 1), which is a truncated S. cerevisiae Mnn2(s) targeting peptide (1-108 nucleotides of MNN2 from Genbank NP_009571) ligated in-frame to a 43 N-terminal amino acid deletion of a human β1,4-galactosyltransferase I (Genbank AH003575). The nomenclature used herein, thus, refers to the targeting peptide/catalytic domain region of a glycosylation enzyme as S. cerevisiae Mnn2(s)/hGalTI Δ43. The encoded fusion protein alone, however, is insufficient to produce N-glycans having predominantly galactosylated glycans as shown in FIG. 9A. Although a peak consistent with the mass of the N-glycan GalGlcNAc₂Man₃GlcNAc₂ [B] is shown with the introduction of hGalTI in P. pastoris YSH-44, subsequent digest of the sample shows that this peak is recalcitrant to β-1,4-galactosidase (Example 7).

In addition, β-1,4-galactosyltransferase activity may be specific to a particular protein of interest. Thus, it is to be further understood that not all targeting peptide/galactosyltransferase catalytic domain fusion constructs function equally as well to produce the proper glycosylation on a glycoprotein of interest. Accordingly, a protein of interest may be introduced into a host cell transformed with a combinatorial DNA library to identify one or more fusion constructs which express a galactosyltransferase activity optimal for the protein of interest. One skilled in the art will be able to produce and select optimal fusion construct(s) using the combinatorial DNA library approach described herein.

It is apparent, moreover, that other such fusion constructs exhibiting localized active galactosyltransferase catalytic domains (or more generally, domains of any enzyme) may be made using techniques described herein. It will be a matter of routine experimentation for one skilled in the art to make and use the combinatorial DNA library of the present invention to optimize, for example, $Gal_2GlcNAc_2Man_3GlcNAc_2$ production from a library of fusion constructs in a particular expression vector introduced into a particular host cell.

Production of Galactosylated N-Glycans in Genetically Altered *P. pastoris*

The human-like galactosylated glycoproteins produced according to the method of present invention include $GalGlcNAcMan_3GlcNAc_2$, $GalGlcNAc_2Man_3GlcNAc_2$, $Gal_2GlcNAc_2Man_3GlcNAc_2$, $GalGlcNAc_3Man_3GlcNAc_2$, $Gal_2GlcNAc_3Man_3GlcNAc_2$, $Gal_3GlcNAc_3Man_3GlcNAc_2$, $GalGlcNAc_4Man_3GlcNAc_2$, $Gal_2GlcNAc_4Man_3GlcNAc_2$, $Gal_3GlcNAc_4Man_3GlcNAc_2$, $Gal_4GlcNAc_4Man_3GlcNAc_2$, $GalGlcNAcMan_5GlcNAc_2$, $GalGlcNAc_2Man_5GlcNAc_2$, $Gal_2GlcNAc_2Man_5GlcNAc_2$, $GalGlcNAcMan_5GlcNAc_2$, $GalGlcNAc_2Man_5GlcNAc_2$, $Gal_2GlcNAc_2Man_5GlcNAc_2$, $GalGlcNAc_3Man_5GlcNAc_2$, $Gal_2GlcNAc_3Man_5GlcNAc_2$ and $Gal_3GlcNAc_3Man_5GlcNAc_2$.

Figure 8A:
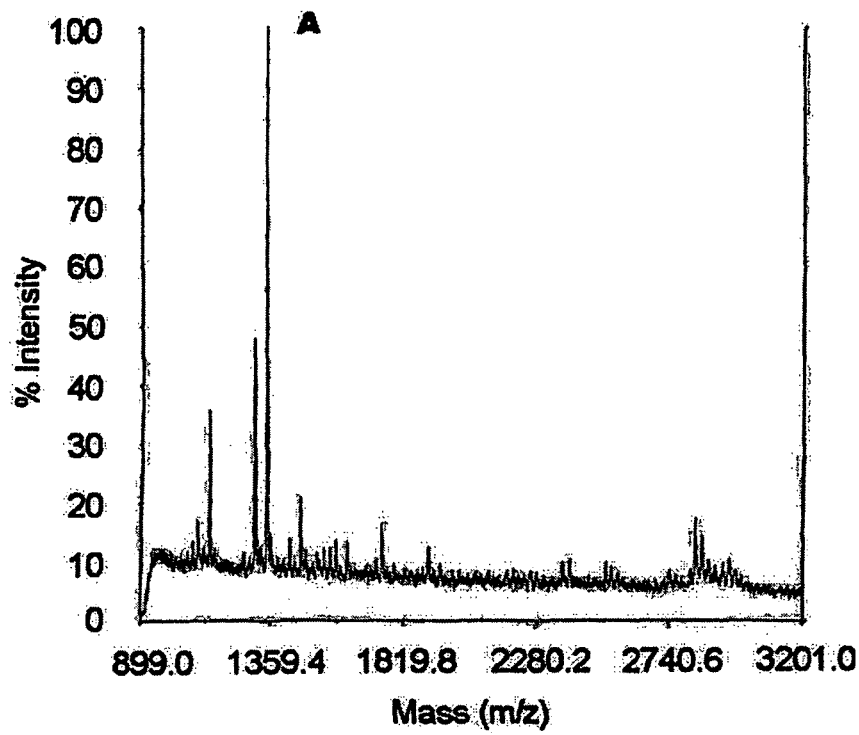
FIG. 8A is a Matrix-Assisted. Laser Desorption/Ionization-Time Of Flight-Mass Spectroscopy (MALDI-TOF-MS) analysis of N-glycans released from K3 produced in RDP30-10 (RDP27 transformed with pRCD257) displaying a peak at 1342 m/z [A] corresponding to the mass of the N-glycan $GlcNAc_2Man_3GlcNAc_2$.
Figure 8B:
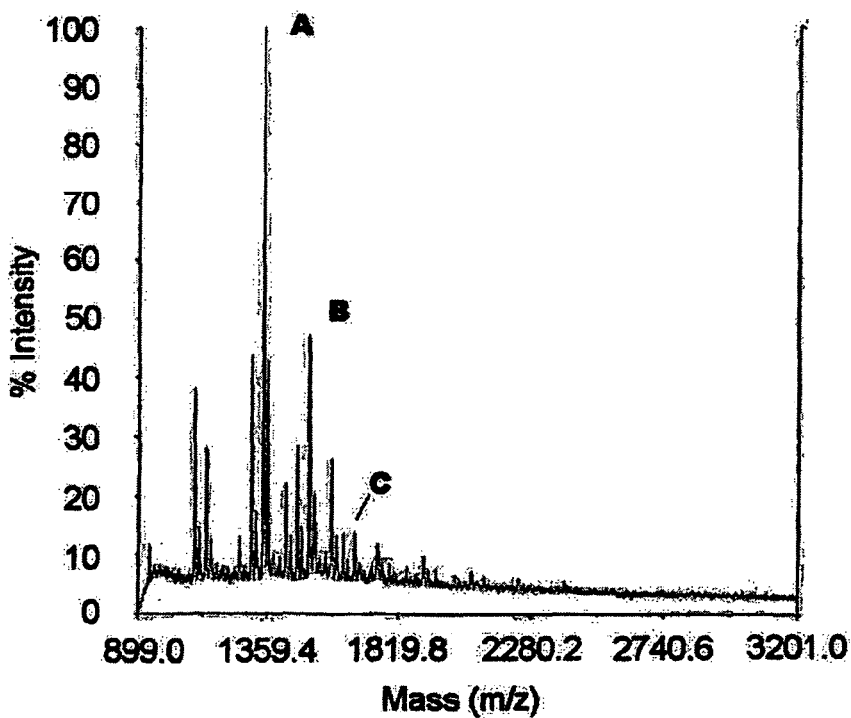
FIG. 8B is a MALDI-TOF-MS analysis of N-glycans released from K3 produced in RDP37 (RDP30-10 transformed with pXB53) displaying a peak at 1505 m/z [B], which corresponds to the mass of the N-glycan $GalGlcNAc_2Man_3GlcNAc_2$ and a peak at 1662 m/z [C], which corresponds to the mass of $Gal_2GlcNAc_2Man_3GlcNAc_2$.

In one embodiment of the invention, the plasmid pXB53 comprising MNN2(s)/hGalTI was transformed in *P. pastoris* RDP30-10, host producing $GlcNAc_2Man_3GlcNAc_2$ (Example 5). The catalytically active β-galactosyltransferase domain catalyzes the transfer of a galactose residue onto an acceptor substrate having a terminal GlcNAc residue (e.g. $GlcNAc_2Man_3GlcNAc_2$) to produce a galactosylated glycoform. Using MALDI-TOF MS, the N-glycans released from the reporter protein from *P. pastoris* RDP37 showed a peak at 1505 m/z, which corresponds to the mass of $GalGlcNAc_2Man_3GlcNAc_2$ [B] (FIG. 8B). Transfer of a galactose residue by the fusion construct comprising human *S. cerevisiae* Mnn2(s)/β1,4-galactosyltransferase onto the acceptor substrate $GlcNAc_2Man_3GlcNAc_2$ producing $GalGlcNAc_2Man_3GlcNAc_2$ was shown to be about 10-20%. FIG. 8B shows the corresponding mass of $Gal_2GlcNAc_2Man_3GlcNAc_2$ at 1662 m/z [C]. Transfer of two galactose residues onto the $GlcNAc_2Man_3GlcNAc_2$ substrate producing $Gal_2GlcNAc_2Man_3GlcNAc_2$ was, therefore, evident. Accordingly, the host of the present invention exhibits at least 10 mole % of galactosyl moiety on a human-like N-glycan.

Figure 12:
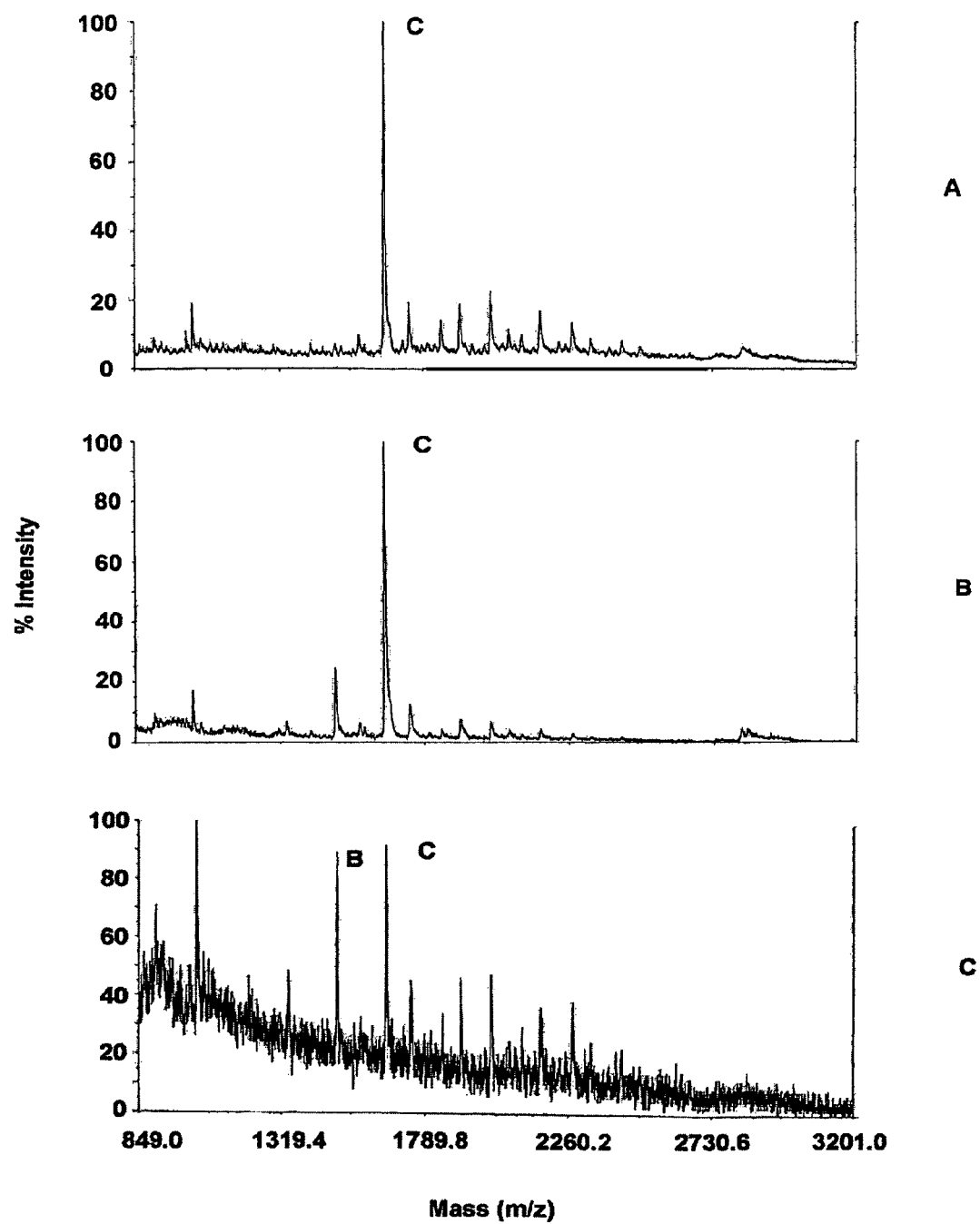
FIG. 12 is a MALDI-TOF-MS analysis of N-glycans released from K3 produced in various *P. pastoris* strains comparing the β-1,4-galactosyltransferase activities. Panel A shows the N-glycan profile of *P. pastoris* YSH-44 transformed with vectors pRCD425 and pSH263 encoding DmUGT, which was designated as RDP57. Panel B shows the N-glycan profile of *P. pastoris* YSH-44 transformed with vectors pRCD440 encoding Mnn2(s)/hGalTII and SpGalE and pSH263 encoding DmUGT, which was designated as RDP72. Panel C shows the N-glycan profile of *P. pastoris* YSH-44 transformed with vectors pRCD443 encoding Mnn2(s)/hGalTIII and SpGalE and pSH263 encoding DmUGT, which was designated as RDP73.

It is recognized that GalTI is capable of transferring a second galactose residue onto an acceptor substrate having a second terminal GlcNAc residue in a host producing complex (e.g., biantennary) glycans. For example, a Mnn2(s)/hGalTI fusion, which is capable of capping the terminal GlcNAc with a galactose residue on the GlcNAcβ1,2 Manα1,3 arm of the glycan $GlcNAc_2Man_3GlcNAc_2$, can form at least one additional β-glycosidic linkage on the other arm exposed with a terminal GlcNAc residue (e.g., GlcNAcβ1,2 Manα1,6), thereby, producing a galactosylated glycoform without the expression of subsequent galactosyltransferases. FIG. 12 displays the MALDI-TOF MS exhibiting a peak at 1663 m/z [C], which corresponds to $Gal_2GlcNAc_2Man_3GlcNAc_2$. The results show that substrate specificity for a particular β1,4-GalT is not limited to catalyzing the transfer of galactose residues on only the designated arm of the glycan, hence, a second galactosyltransferase may be obviated. Accordingly, in one embodiment of the present invention, expression of only one β1,4-GalT activity is capable of producing mono-, bi-, tri- or tetra-antennary galactosylated glycoforms. In such an embodiment, all glycosidic linkages between the galactose residue and the GlcNAc residue on the glycan would be the same. For instance, expression of hGalT1 in a host producing biantennary glycans would exhibit two terminal Galβ1,4-GlcNAcβ1,2 linkages.

Alternatively, a different β-galactosyltransferase activity (e.g. hGalT II) or a catalytically active part thereof is expressed in a lower eukaryotic host cell. In one embodiment, a vector pRCD440 comprising the MNN2(s)/hGalTII and SpGALE and the vector pSH263 (FIG. 3B) comprising DmUGT was transformed into a host *P. pastoris* YSH-44 (FIG. 12B). The N-glycan analysis of the transformants showed the production of the $Gal_2GlcNAc_2Man_3GlcNAc_2$ glycoform indicating that hGalTII transferred both galactose residues onto the acceptor substrate (FIG. 12B). Bi-galactosylated structures ($Gal_2GlcNAc_2Man_3GlcNAc_2$) are predominant. Transfer of galactosyl moiety with respect to % neutral glycans was approximately 75%.

In yet another embodiment, a sequence encoding the hGalTIII is expressed in a lower eukaryotic host cell. FIG. 12C shows galactose transfer of the combined mono- and bi-galactosylated glycans to be about 50 to 60 mole %. Comparison of hGalTI, hGalTII and hGalTIII show various level of galactose transfer (FIG. 12A-C). The N-glycan profile from *P. pastoris* RDP71 (FIG. 12A) shows that the transfer of galactose residue by the expression of hGalTI is optimal (about 80 mole %) for the K3 reporter protein.

Expression of Additional β1,4-Galactosyltransferases

In another embodiment, hGalTI and hGalTII are sequentially localized and expressed using medial and late Golgi targeting sequences, respectively. For example, the hGalT1 is localized in the medial Golgi whereas the hGalTII is localized in the late Golgi. Alternatively, to avoid substrate competition with Mannosidase II, in another embodiment, late Golgi leaders are used for β-galactosyltransferases.

Expression of galactosyltransferase activities usually generates both mono- and bi-galactosylated glycans. Multiple antennary galactosylated glycoforms in addition to mono-galactosylated glycoforms are generally produced in host cells expressing galactosyltransferase activity.

It will be a matter of routine experimentation for a skilled artisan to optimize galactosyltransferase activity or expression of the gene encoding the protein by using various promoters and various expression vectors in a recombinant host cell.

Tailored Galactosylated Glycosidic Linkages in the Production of N-Glycans

In another feature of the invention, production of multiple antennary galactosylated glycoproteins using different GalTs result in different β-glycosidic linkages. In one embodiment, desired β-glycosidic linkages of preference are generated in a lower eukaryotic host cell. For example, any one of the β1,4GalT family (e.g., hGalTI, hGalT2, hGalT3, hGalT4, hGalT5, hGalT6, hGalT7, bGalTI, XlGalT, CeGalTII) is expressed for the production of galactosylated glycoproteins characterized as having a β1,4Gal glycosidic linkage.

Alternatively, by expressing other galactosyltransferases, such as, β1,3GalT or β1,6GalT activities (enzyme, homologs, variants, derivatives and catalytically active fragment thereof) in a lower eukaryotic host cell (e.g. *P. pastoris*), a galactose residue is transferred onto an intermediate oligosaccharide acceptor substrate forming a specifically desired βGal-glycosidic linkage. Various terminal galactose linkages (e.g., β1,3, β1,4; or β1,6) are formed as a result of the expression of a desire β-galactosyltransferase activity.

GalNAcT Expression in Lower Eukaryotes

GalNAc capped glycans have been observed on specific proteins in human. In another aspect of the present invention, a gene encoding GalNAc Transferase (GalNAcT) is expressed in a lower eukaryotic host cell, which transfers GalNAc residues onto a substrate having a terminal GlcNAc residue. In one embodiment, a gene encoding C. elegans GalNAcT (Genbank AN NP_490872) catalyzes the transfer of a GalNAc residue onto a substrate having a terminal GlcNAc residue extending the oligosaccharide branch of the glycans produced in a host cell.

Enhanced Galactosyl Transfer

The hGalTI expression comparison as shown in FIG. 12 indicates that β-galactosyltransferase expression alone may not be sufficient in the formation of βGal-glycosidic linkages on acceptor substrates in a lower eukaryote. The transfer of a galactose residue is enhanced by the addition of a heterologous gene encoding an epimerase or galactokinase, a galactose-1-phosphate uridyl transferase and/or a gene encoding a UGT. Sufficient quantity of galactosylated glycoforms (e.g., $Gal_2GlcNAc_2Man_3GlcNAc_2$) is desirable as therapeutic glycoprotein. Accordingly, it is a feature of the present invention to enhance galactosyl transfer onto glycans by additional expression of a transport activity and/or to elevate endogenous UDP-galactose levels. In one embodiment, an epimerase activity is introduced in a host cell to increase UDP-galactose levels. In another embodiment, increased UDP-galactose level is mediated by galactokinase or a galactose-1-phosphate uridyl transferase activity. The present invention, therefore, provides a method to enhance galactosyltransfer by introducing and expressing a β-galactosyltransferase activity in combination with either a UDP-Gal transport activity and/or by elevating endogenous UDP-galactose levels via an epimerase or galactokinase or a galactose-1-phosphate uridyl transferase.

Cloning and Expression of UDP-Galactose Transporter (UGT) in Lower Eukaryotic Hosts in the Production of Human-Like Glycoproteins Herein the specification, is also disclosed a method to introduce and express a gene encoding a UDP-galactose transporter in a lower eukaryotic cell (e.g. P. pastoris) for the production of human-like galactosylated glycoproteins.

Cloning and Expression of S. pombe UDP-Galactose Transporter

Gene-specific primers were designed to complement the homologous regions of the S. pombe UDP-galactose transporter gene (Genbank AL022598) and PCR amplified from S. pombe genomic DNA (ATCC24843) eliminating a single intron. Primers RCD164 (SEQ ID NO:7) and RCD177 (SEQ ID NO:8) were used to amplify the 5' 96 bp of the gene. Primers RCD176 (SEQ ID NO:9) and RCD165 (SEQ ID NO:10) were used to amplify the 3' 966 bp. Primers RCD164 (SEQ ID NO:7) and RCD165 (SEQ ID NO:10) were used to overlap the two amplified products into a single PCR fragment containing one contiguous ORF with NotI and PacI sites introduced at the ends. The PCR product was cloned into pCR2.1 TA (Invitrogen) and sequenced. The gene product was subcloned into plasmid pJN335 containing the P. pastoris GAPDH promoter (Example 2).

Accordingly, in one embodiment, a plasmid pRCD257 encoding the S. pombe UDP-galactose transporter (Genbank AB023425) is constructed and expressed in a host producing terminal GlcNAc residues (P. pastoris RDP-27 (e.g. $GlcNAcMan_3GlcNAc_2$)).

Cloning and Expression of Various UDP-Galactose Transporters

Figure 3A:
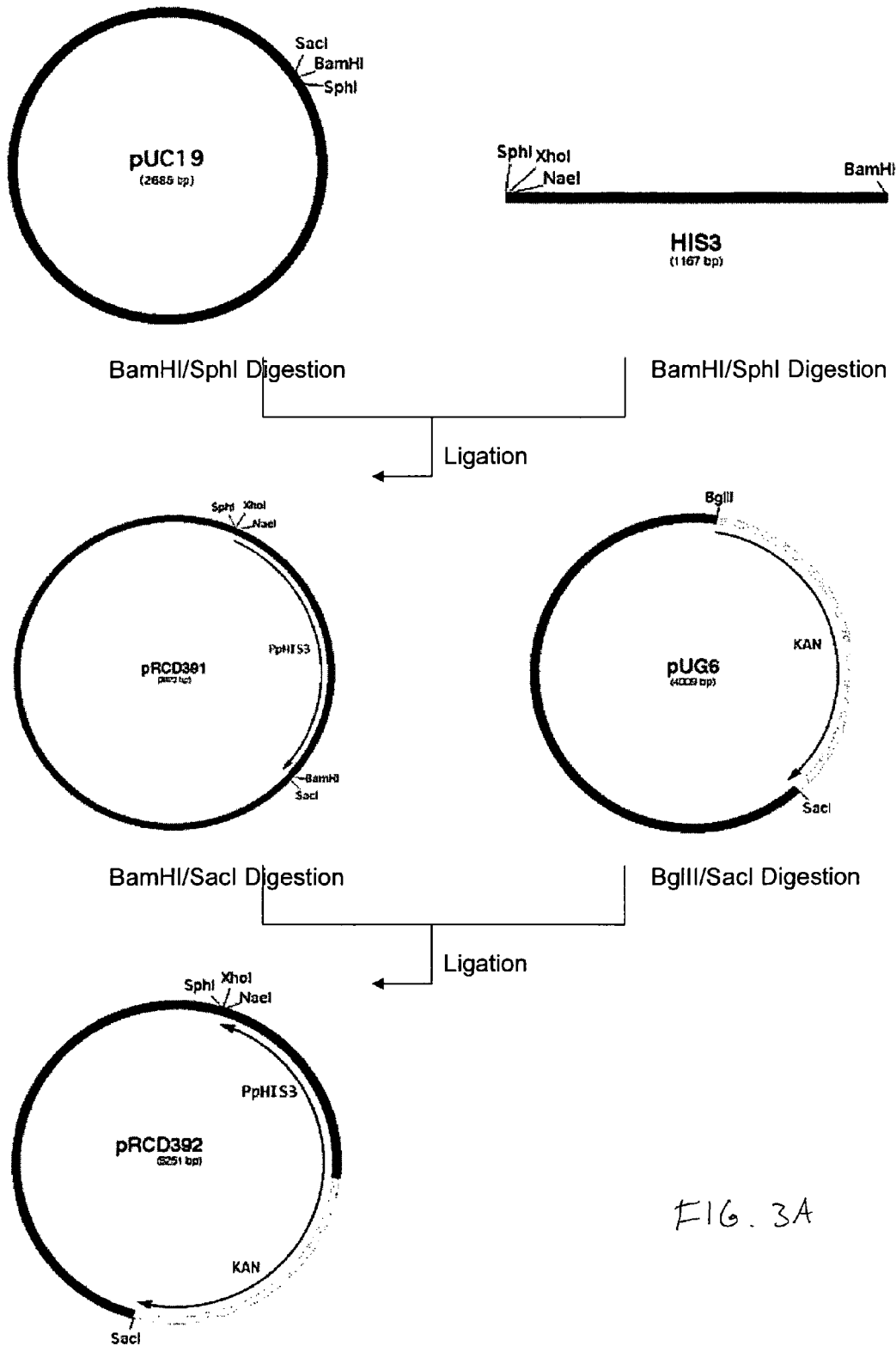
FIGS. 3A-3B depicts the construction of a plasmid map of the integration vector pSH263 encoding the *D. melanogaster* UDP-galactose Transporter (DmUGT).
Figure 3B:
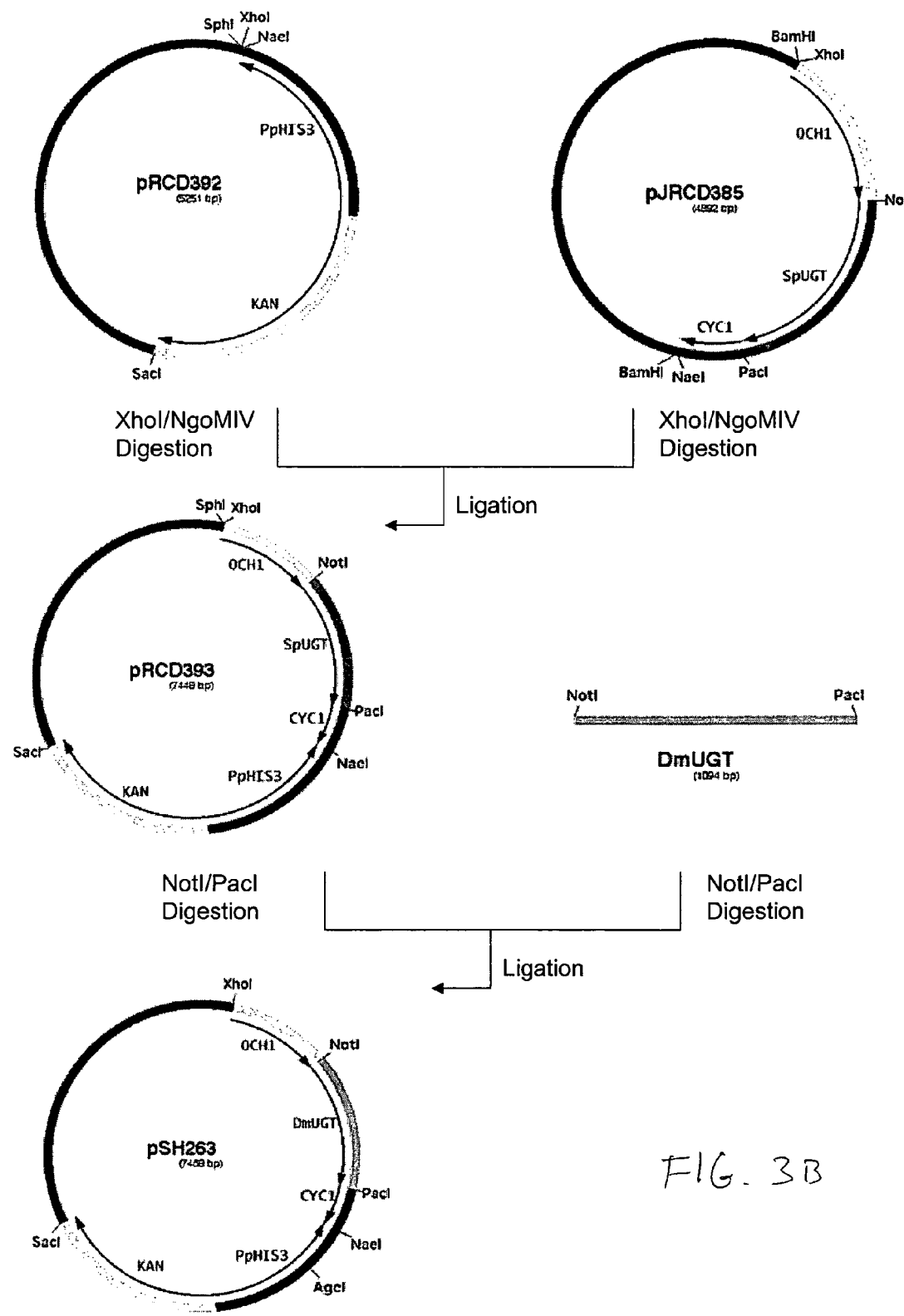

In a preferred embodiment, the gene encoding the D. melanogaster UDP-galactose transporter is introduced and expressed in a lower eukaryotic host cell. The D. melanogaster UGT was PCR amplified from a D. melanogaster cDNA library (UC Berkeley Drosophila Genome Project, ovary λ-ZAP library GM) and cloned into the pCR2.1 PCR cloning vector and sequenced. Primers DmUGT-5' (SEQ ID NO:11) and DmUGT-3' (SEQ ID NO:12) were used to amplify the gene introducing NotI and PacI sites. The NotI and PacI sites were used to subclone this gene fused downstream of the PpOCH1 promoter at the NotI/PacI sites in pRCD393 creating pSH263 (FIG. 3B). Example 2 describes cloning of various other UDP galactose transporters.

Figure 11:
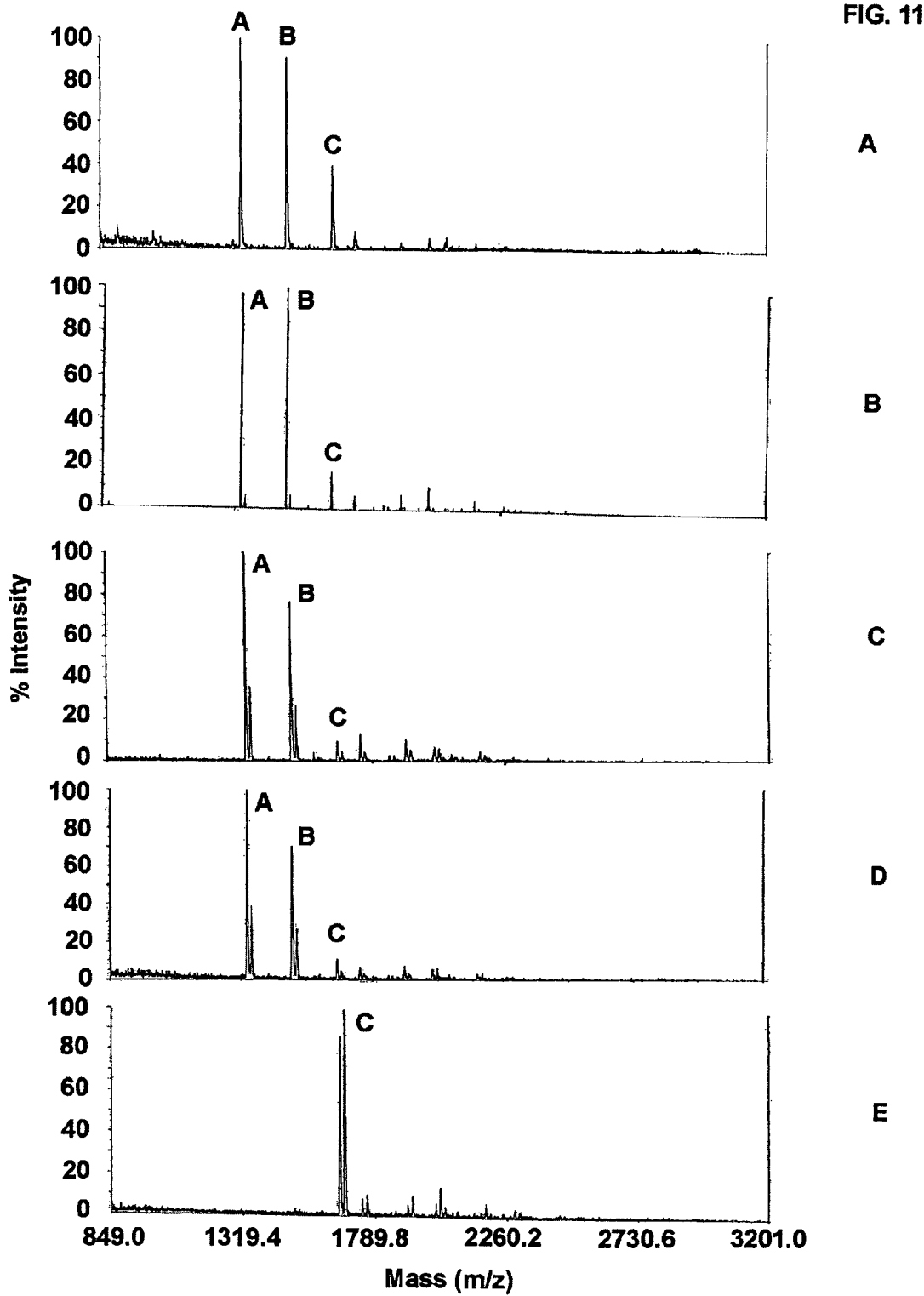
FIG. 11 is a MALDI-TOF-MS analysis of N-glycans isolated from K3 produced in various *P. pastoris* strains comparing the UDP-galactose transport activities. Panel A shows the N-glycan profile of *P. pastoris* YSH-44 transformed with vectors pRCD425 encoding Mnn2(s)/hGalTI and SpGalE, which was designated RDP52. Panel B shows the N-glycan profile of *P. pastoris* YSH-44 transformed with vectors pRCD425 and pRCD393 encoding SpUGT, which was designated as RDP69. Panel C shows the N-glycan profile of *P. pastoris* YSH-44 transformed with vectors pRCD425 and pSH262 encoding hUGT2, which was designated as RDP70. Panel D shows the N-glycan profile of *P. pastoris* YSH-44 transformed with vectors pRCD425 and pSH264 encoding hUGTI, which was designated as RDP71. Panel E shows the N-glycan profile of *P. pastoris* YSH-44 transformed with vectors pRCD425 and pSH263 encoding DmUGT, which was designated RDP57.

FIG. 11 shows UDP-transporter activity in comparison for enhanced galactose transfer. As the best mode of the present invention, the UDP-galactose transporter isolated from D. melanogaster is expressed in P. pastoris. The activity of the human GalTI gene fusion co-expressed with the D. melanogaster UDP-galactose transporter (DmUGT) is shown in FIG. 11E. Surprisingly, host cells expressing the D. melanogaster UGT produce predominantly galactosylated glycoforms, whereas, UGTs from S. pombe (FIG. 11B), human I (FIG. 11C) and human II (FIG. 11D) showed less than optimal transfer. A significant increase in the production of a bi-galactosylated, afucosylated and asialylated glycoform $Gal_2GlcNAc_2Man_3GlcNAc_2$ is produced. The uniform peak at 1664 m/z [C] corresponds to the mass of the glycan $Gal_2GlcNAc_2Man_3GlcNAc_2$. A host cell (e.g., P. pastoris) expressing the DmUGT exhibits at least 90 mole % galactose transfer in comparison to other UDP-galactose transporters.

UDP-Galactose Transporter Polypeptides

The invention additionally provides various combination of transporter-transferase fusions expressed in a lower eukaryotic host cell (e.g., P. pastoris). Accordingly, in one embodiment, the present invention provides a lower eukaryotic host comprising a UDP-galactose transporter fused in-frame to a catalytically active β-galactosyltransferase domain. In another embodiment, the host cell producing human-like glycoproteins comprises a UDP-galactose transporter isolated from S. pombe and S. cerevisiae Mnn2(s) targeting peptide fused in-frame to hGalTI catalytic domain.

Expression of UDP-Galactose 4-Epimerase in Lower Eukaryotic Hosts in the Production of Human-Like Glycoproteins In another aspect of the invention, a method is provided for producing a human-like glycoprotein in a lower eukaryote (e.g. P. pastoris) by expressing a β1,4-galactosyltransferase activity and at least a UDP-galactose 4-epimerase activity (enzyme, homologs, variants, derivatives and catalytically active fragment thereof). The epimerase is an enzyme that catalyzes the interconversion of UDP-galactose and UDP-glucose. Using well known techniques in the art, gene-specific primers are designed to complement the homologous regions of an epimerase gene (e.g. ScGAL10, SpGALE, hGALE) and PCR amplified (Example 3). In one embodiment, a gene encoding the S. cerevisiae Gal10 activity or a recombinant nucleic acid molecule encoding an epimerase or expression from a nucleic acid molecule encoding an epimerase activity is introduced and expressed in a lower eukaryotic host cell (e.g. *P. pastoris*) to produce human-like glycoproteins characterized as having a terminal β-galactose residue. Alternatively, by activation of an epimerase activity, a host cell is engineered to produce increased levels of galactosylated glycoforms.

Expression of UDP-Galactose 4-Epimerase in the Production of Complex N-Glycans

Figure 9B:
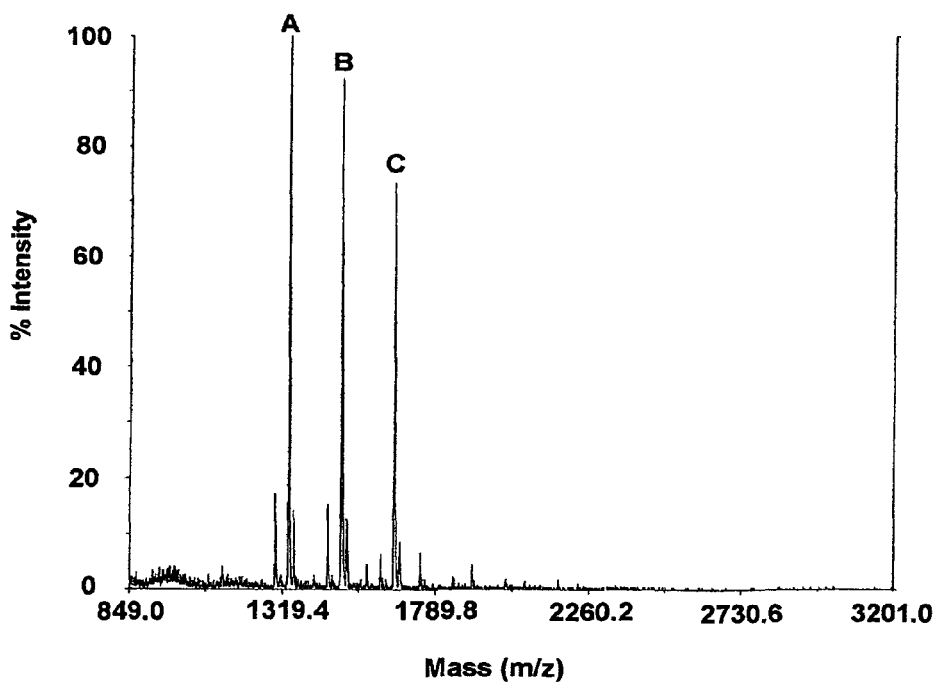
FIG. 9B is a MALDI-TOF-MS analysis of N-glycans released from K3 produced in YSH-44 transformed with pXB53 and pRCD395 displaying a peak at 1501 m/z [B], which corresponds to the mass of the N-glycan $GalGlcNAc_2Man_3GlcNAc_2$; a peak at 1663 m/z [C], which corresponds to the mass of $Gal_2GlcNAc_2Man_3GlcNAc_2$; and a peak at 1339 m/z [A], which corresponds to the mass of $GlcNAc_2Man_3GlcNAc_2$.

In one embodiment, a gene encoding an epimerase activity is expressed to convert UDP-glucose to UDP-galactose, generating an increased level of UDP-galactose for galactosyltransfer in host cells. The expression of an epimerase activity in addition to a β-1,4-galactosyltransferase activity increases production of galactosylated N-glycans. FIG. 9B shows a yeast strain producing complex glycans (e.g., *P. pastoris* YSH-44) transformed with a Mnn2(s)/hGalTI fusion in combination with pRCD395, a plasmid encoding ScGal10. The addition of the ScGal10 epimerase increases the available UDP-galactose for galactose transfer. A peak at 1501 m/z [B] corresponds to the transfer of one galactose residue on the glycan $GlcNAc_2Man_3GlcNAc_2$ and a peak at 1663 m/z [C] corresponds to the transfer of two galactose residues on the glycan $GlcNAc_2Man_3GlcNAc_2$. Preferably, at least 60 mole % of galactose is transferred with respect to % total neutral glycans. Accordingly, in one embodiment, a β-1,4-galactosyltransferase activity in combination with an epimerase activity is expressed in a host cell to produce galactosylated glycoproteins (Example 7).

Expression of UDP-Galactose 4-Epimerase in the Production of Hybrid N-Glycans

Figure 10A:
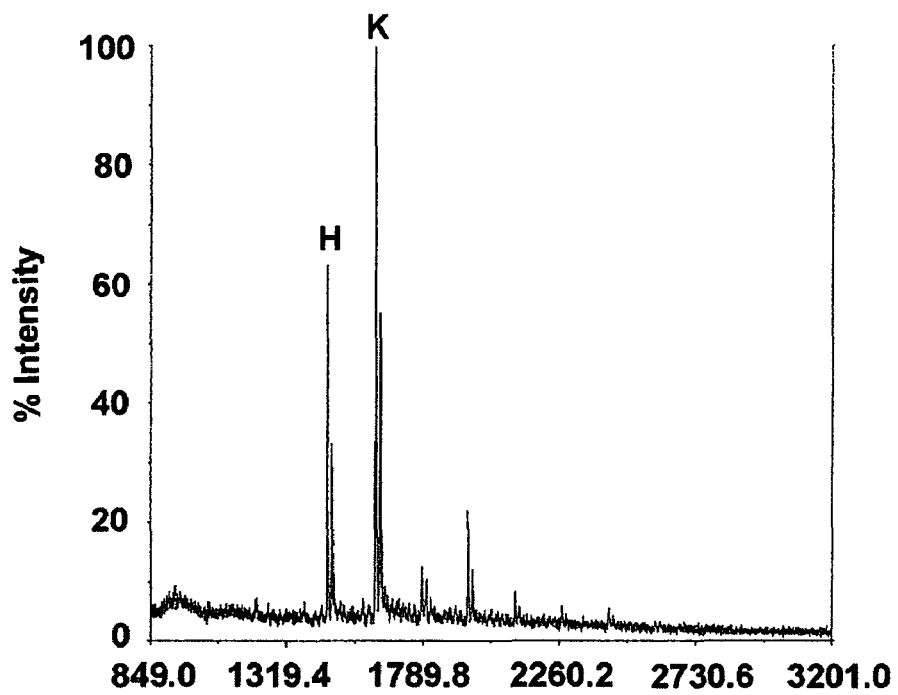
FIG. 10A is a MALDI-TOF-MS analysis of N-glycans released from K3 produced in RDP 39-6 (*P. pastoris* PBP-3 (U.S. Pat. Appl. No. 20040018590)) transformed with pRCD352 and pXB53 displaying a predominant peak at 1622 m/z [K], which corresponds to the mass of the N-glycan $GalGlcNAcMan_5GlcNAc_2$ and a peak at 1460 m/z [H], which corresponds to the mass of $GlcNAcMan_5GlcNAc_2$.
Figure 10B:
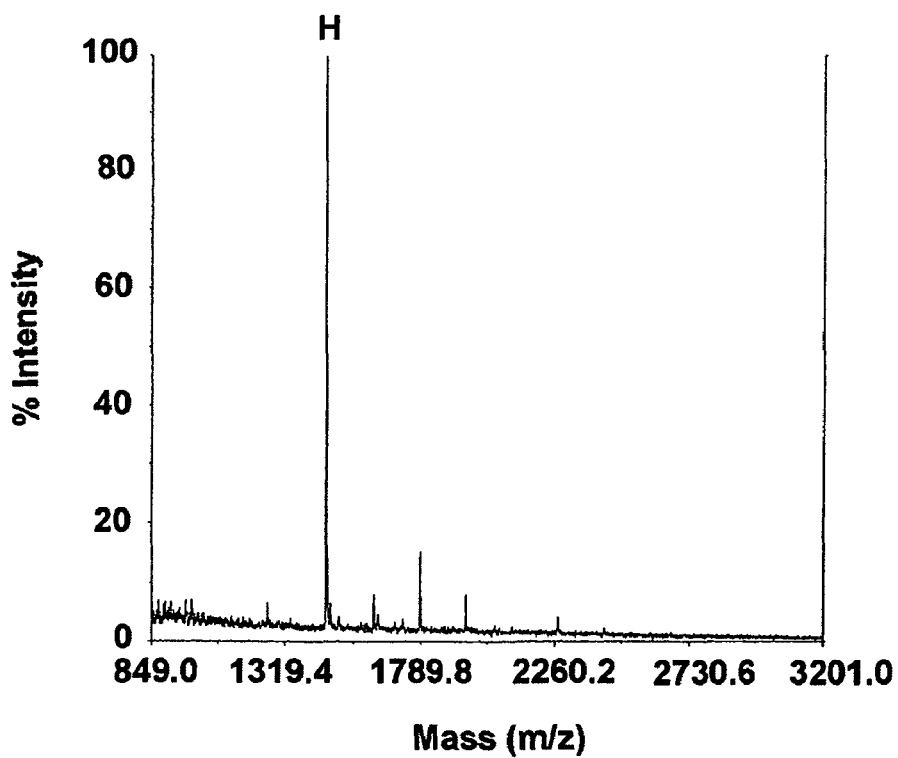
FIG. 10B is a MALDI-TOF-MS analysis of N-glycans released from K3 produced in RDP 39-6 after α1,2 and β1,4-galactosidase digest displaying a predominant peak at 1461 m/z [H], which corresponds to the mass of the N-glycan $GlcNAcMan_5GlcNAc_2$.

In another embodiment, the introduction and expression of ScGAL10 increases galactose transfer on a hybrid glycoprotein in a lower eukaryote (Example 6). FIG. 10A shows the *P. pastoris* strain RDP39-6 expressing an Mnn2(m)/hGalTI fusion in combination with the ScGal10 epimerase producing hybrid galactosylated N-glycans. The N-glycan analysis shows peak at 1622 m/z [K], which corresponds to the mass of the glycan $GalGlcNAcMan_5GlcNAc_2$ confirming transfer of one galactose residue, and a peak at 1460 m/z [H], which corresponds to the mass of the hybrid glycan $GlcNAcMan_5GlcNAc_2$. Subsequent β1,4-galactosidase digest confirms presence of a single galactose residue (FIG. 10B). Preferably, at least 70 mole % of galactose transfer is detected with respect to % total neutral glycans.

Figure 13:
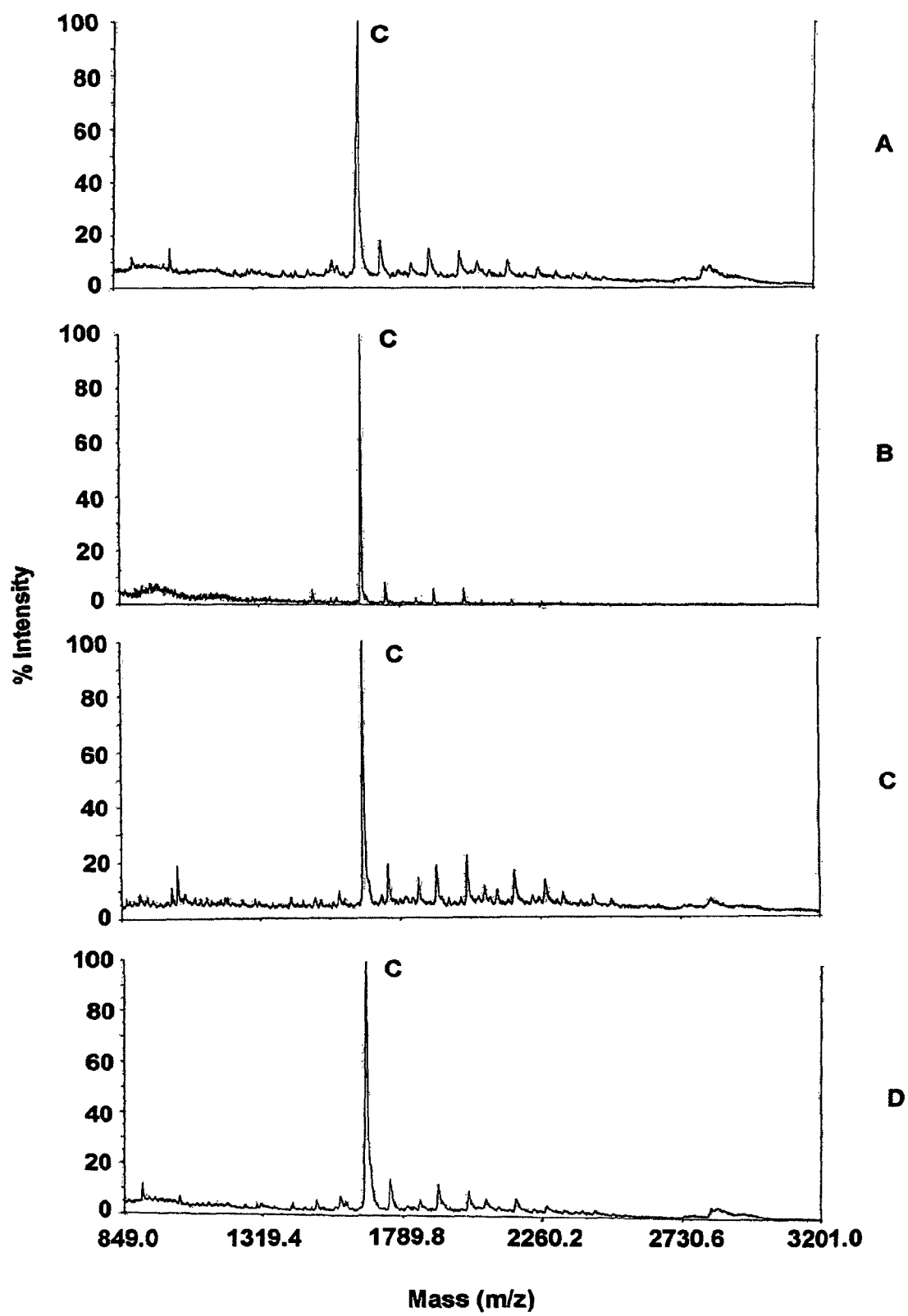
FIG. 13 is a MALDI-TOF-MS analysis of N-glycans released from K3 produced in various *P. pastoris* strains comparing epimerase activities. Panel A shows the N-glycan profile of *P. pastoris* YSH-44 transformed with vectors pRCD424 encoding Mnn2(s)/hGalTI and ScGal10 and pSH263 encoding DmUGT, which was designated as RDP65. Panel B shows the N-glycan profile of *P. pastoris* YSH-44 sequentially transformed with vectors pSH263 encoding DmUGT and pRCD425, which was designated as RDP74. Panel C shows the N-glycan profile of *P. pastoris* YSH-44 sequentially transformed with vectors pRCD425 and then pSH263 encoding DmUGT, which was designated as RDP63. Panel D shows the N-glycan profile of *P. pastoris* YSH-44 transformed with vectors pXB53 and pRCD438 encoding Mnn2(s)/hGalTI and hGalE and pSH263 encoding DmUGT, which was designated as RDP67.

Still other epimerases are expressed in a host cell to increase galactose transfer. Example 3 describes construction of epimerase constructs and FIG. 13 shows the activity of various epimerases in the production of human-like N-glycans. The expression of ScGal10 along with Mnn2(s)/hGalTI and DmUGT in FIG. 13A shows a predominant bi-galactosylated glycoform $Gal_2GlcNAc_2Man_3GlcNAc_2$. Similarly, the transformation of SpGalE, Mnn2(s)/hGalTI and the DmUGT in either order results in the production of the bi-galactosylated glycoform (FIGS. 13B and C). The addition of hGalE has the same effect (FIG. 13D). Preferably, the epimerase is selected from the group consisting of *S. cerevisiae* UDP-galactose 4-epimerase, *S. pombe* UDP-galactose 4-epimerase, *E. coli* UDP-galactose 4-epimerase and *H. sapiens* UDP-galactose 4-epimerase. It is contemplated that other epimerases, without limitation, can be selected and expressed in the host cell as well.

Nucleic Acid Sequences Encoding SpGALE

The present invention additionally provides isolated nucleic acid molecules that include the GALE gene from *S. pombe* and variants thereof. The full-length nucleic acid sequence for this gene, which encodes the enzyme UDP-galactose 4-epimerase, has already been sequenced and identified as set forth in Genbank NC_003423. Primers used to amplify SpGALE from *S. pombe* genomic DNA revealed a 175 bp intron, which was eliminated (Example 3). Included within the cloned genomic sequence is a coding sequence for *S. pombe* UDP-galactose 4-epimerase. The encoded amino acid sequence is also set forth as SEQ ID NO:13. The SpGALE gene is particularly useful in generating a sufficient pool of UDP-galactose for galactose transfer onto N-glycans in a host cell. Expression of the SpGALE gene in a lower eukaryote provides increased and efficient galactose transfer in N-linked oligosaccharide synthesis.

In one embodiment, the invention provides an isolated nucleic acid molecule having a nucleic acid sequence comprising or consisting of a SpGALE coding sequence as set forth in SEQ ID NO:14, and homologs, variants and derivatives thereof. In a further embodiment, the invention provides a nucleic acid molecule comprising or consisting of a sequence which is a variant of the SpGALE gene having at least 53% identity to the wild-type gene. The nucleic acid sequence can preferably have at least 70%, 75% or 80% identity to the wild-type gene. Even more preferably, the nucleic acid sequence can have 85%, 90%, 95%, 98%, 99%, 99.9% or even higher identity to the wild-type gene.

In another embodiment, the nucleic acid molecule of the invention encodes a polypeptide having the amino acid sequence of SEQ ID NO: 13. Also provided is a nucleic acid molecule encoding a polypeptide sequence that is at least 60% identical to SEQ ID NO:13. Typically the nucleic acid molecule of the invention encodes a polypeptide sequence of at least 70%, 75% or 80% identity to SEQ ID NO:13. Preferably, the encoded polypeptide is 85%, 90% or 95% identical to SEQ ID NO:13, and the identity can even more preferably be 98%, 99%, 99.9% or even higher.

Epimerase Conserved Regions Involved in the Interconversion of UDP-Glucose and UDP-Galactose for the Production of Galactosylated Glycoproteins Sequence alignment of epimerases from *S. pombe*, human, *E. coli* and the first 362 amino acid residues of *S. cerevisiae* shows highly conserved regions indicating the presence of several motifs and a potential active site (FIG. 7) (Example 11). In one embodiment, the invention encompasses a polypeptide comprising the amino acid sequence of SEQ ID NO:13, which has a potential UDP-galactose or UDP-glucose binding motif at

9-VLVTGGXGYIGSHT-22 (SEQ ID NO:53),

83-VIHFAGLKAVGESXQXPLXYY-103 (SEQ ID NO:49),

127-FSSSATVYGX-136 (SEQ ID NO:50),

184-LRYFNPXGAHXSGXXGEDPXGIPNNLX-PYXXQVAXGRX-221 (SEQ ID NO:51), or

224-LXXFGXDYXXXDGTXXRDYIHVXDLAXX-HXXAX-256 (SEQ ID NO:52).

In another preferred embodiment, the amino acid residue at position 15 of the first sequence is selected from the group consisting of S and A.

In another preferred embodiment, the amino acid residue at position 96 of the second sequence is selected from the group consisting of T and V.

In another preferred embodiment, the amino acid residue at position 98 of the second sequence is selected from the group consisting of V, K and I.

In another preferred embodiment, the amino acid residue at position 101 of the second sequence is selected from the group consisting of S, D, E and R.

In another preferred embodiment, the amino acid residue at position 136 of the third sequence is selected from the group consisting of D and N.

In another preferred embodiment, the amino acid residue at position 190 of the fourth sequence is selected from the group consisting of G, T, V and I.

In another preferred embodiment, the amino acid residue at position 194 of the fourth sequence is selected from the group consisting of P and A.

In another preferred embodiment, the amino acid residue at position 197 of the fourth sequence is selected from the group consisting of E, C, D and L.

In another preferred embodiment, the amino acid residue at position 198 of the fourth sequence is selected from the group consisting of L, I and M.

In another preferred embodiment, the amino acid residue at position 203 of the fourth sequence is selected from the group consisting of L and Q.

In another preferred embodiment, the amino acid residue at position 210 of the fourth sequence is selected from the group consisting of L and M.

In another preferred embodiment, the amino acid residue at position 213 of the fourth sequence is selected from the group consisting of I, V and M.

In another preferred embodiment, the amino acid residue at position 214 of the fourth sequence is selected from the group consisting of A and S.

In another preferred embodiment, the amino acid residue at position 218 of the fourth sequence is selected from the group consisting of V and I.

In another preferred embodiment, the amino acid residue at position 221 of the fourth sequence is selected from the group consisting of L and R.

In another preferred embodiment, the amino acid residue at position 225 of the fifth sequence is selected from the group consisting of N, A and Y.

In another preferred embodiment, the amino acid residue at position 226 of the fifth sequence is selected from the group consisting of V and I.

In another preferred embodiment, the amino acid residue at position 229 of the fifth sequence is selected from the group consisting of D and N.

In another preferred embodiment, the amino acid residue at position 232 of the fifth sequence is selected from the group consisting of P and D.

In another preferred embodiment, the amino acid residue at position 233 of the fifth sequence is selected from the group consisting of T and S.

In another preferred embodiment, the amino acid residue at position 234 of the fifth sequence is selected from the group consisting of S, E and R.

In another preferred embodiment, the amino acid residue at position 238 of the fifth sequence is selected from the group consisting of P and G.

In another preferred embodiment, the amino acid residue at position 239 of the fifth sequence is selected from the group consisting of I and V.

In another preferred embodiment, the amino acid residue at position 246 of the fifth sequence is selected from the group consisting of C, V and M.

In another preferred embodiment, the amino acid residue at position 250 of the fifth sequence is selected from the group consisting of E, K and D.

In another preferred embodiment, the amino acid residue at position 251 of the fifth sequence is selected from the group consisting of A and G.

In another preferred embodiment, the amino acid residue at position 253 of the fifth sequence is selected from the group consisting of V and I.

In another preferred embodiment, the amino acid residue at position 254 of the fifth sequence is selected from the group consisting of A and V.

In another preferred embodiment, the amino acid residue at position 256 of the fifth sequence is selected from the group consisting of L and M.

Isolated Polypeptides

According to another aspect of the invention, isolated polypeptides (including muteins, allelic variants, fragments, derivatives, and analogs) encoded by the nucleic acid molecules of the invention are provided. In one embodiment, the isolated polypeptide comprises the polypeptide sequence corresponding to SEQ ID NO:13. In an alternative embodiment of the invention, the isolated polypeptide comprises a polypeptide sequence at least 60% identical to SEQ ID NO:13. Preferably the isolated polypeptide of the invention has at least 70%, 75% or 80% identity to SEQ ID NO:13. More preferably, the identity is 85%, 90% or 95%, but the identity to SEQ ID NO:13 can be 98%, 99%, 99.9% or even higher.

According to other embodiments of the invention, isolated polypeptides comprising a fragment of the above-described polypeptide sequences are provided. These fragments preferably include at least 20 contiguous amino acids, more preferably at least 25, 30, 35, 40, 45, 50, 60, 70, 80, 90, 100 or even more contiguous amino acids.

The polypeptides of the present invention also include fusions between the above-described polypeptide sequences and heterologous polypeptides. The heterologous sequences can, for example, include heterologous sequences designed to facilitate purification and/or visualization of recombinantly-expressed proteins. Other non-limiting examples of protein fusions include those that permit display of the encoded protein on the surface of a phage or a cell, fusions to intrinsically fluorescent proteins, such as green fluorescent protein (GFP), and fusions to the IgG Fc region.

UDP-Galactose 4-Epimerase/β1,4-Galactosyltransferase Fusion Polypeptides

Figure 4:
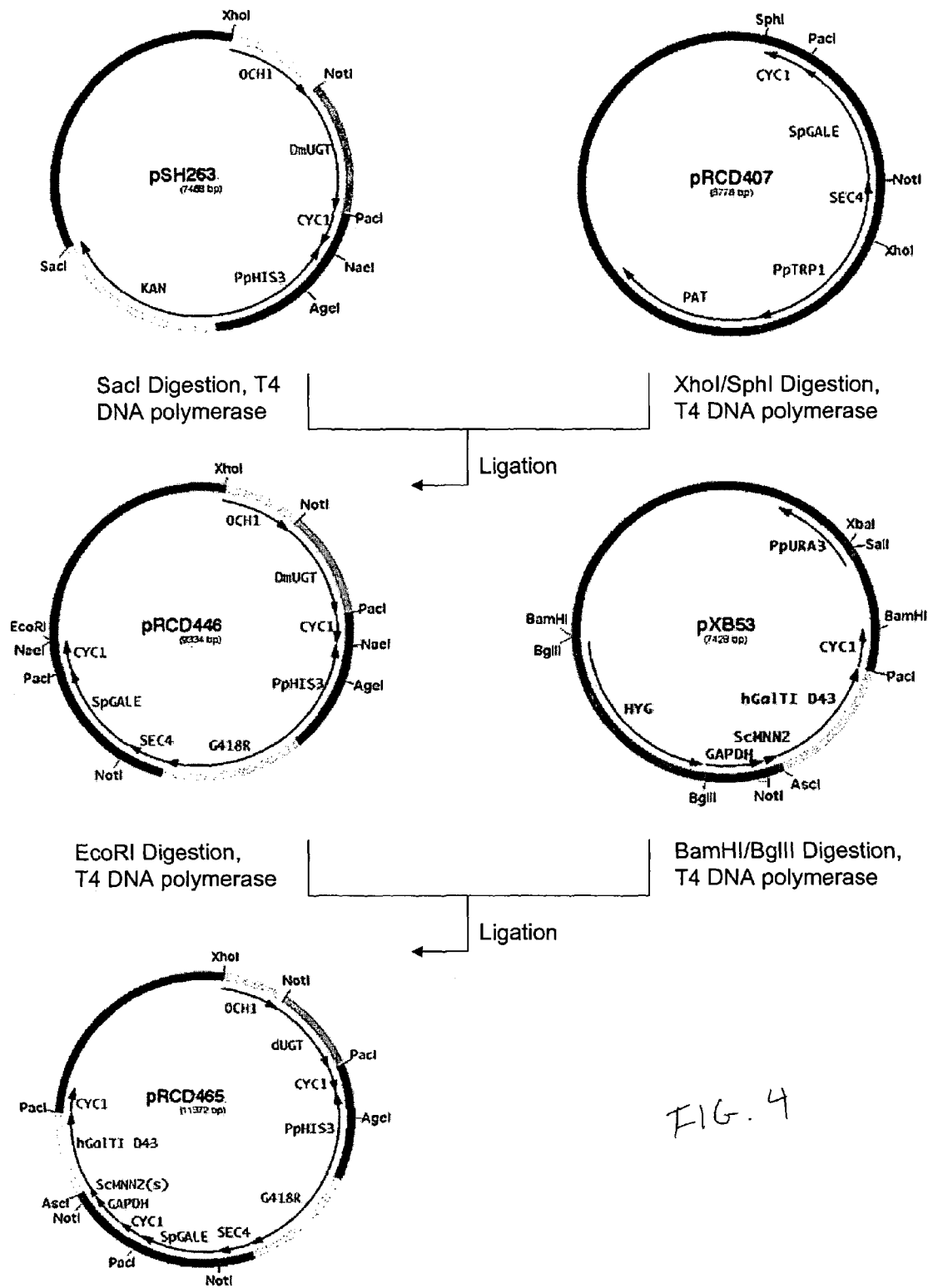
FIG. 4 depicts the construction of a plasmid map of the integration vector pRCD465 encoding hGalTI, SpGalE and DmUGT.
Figure 5:
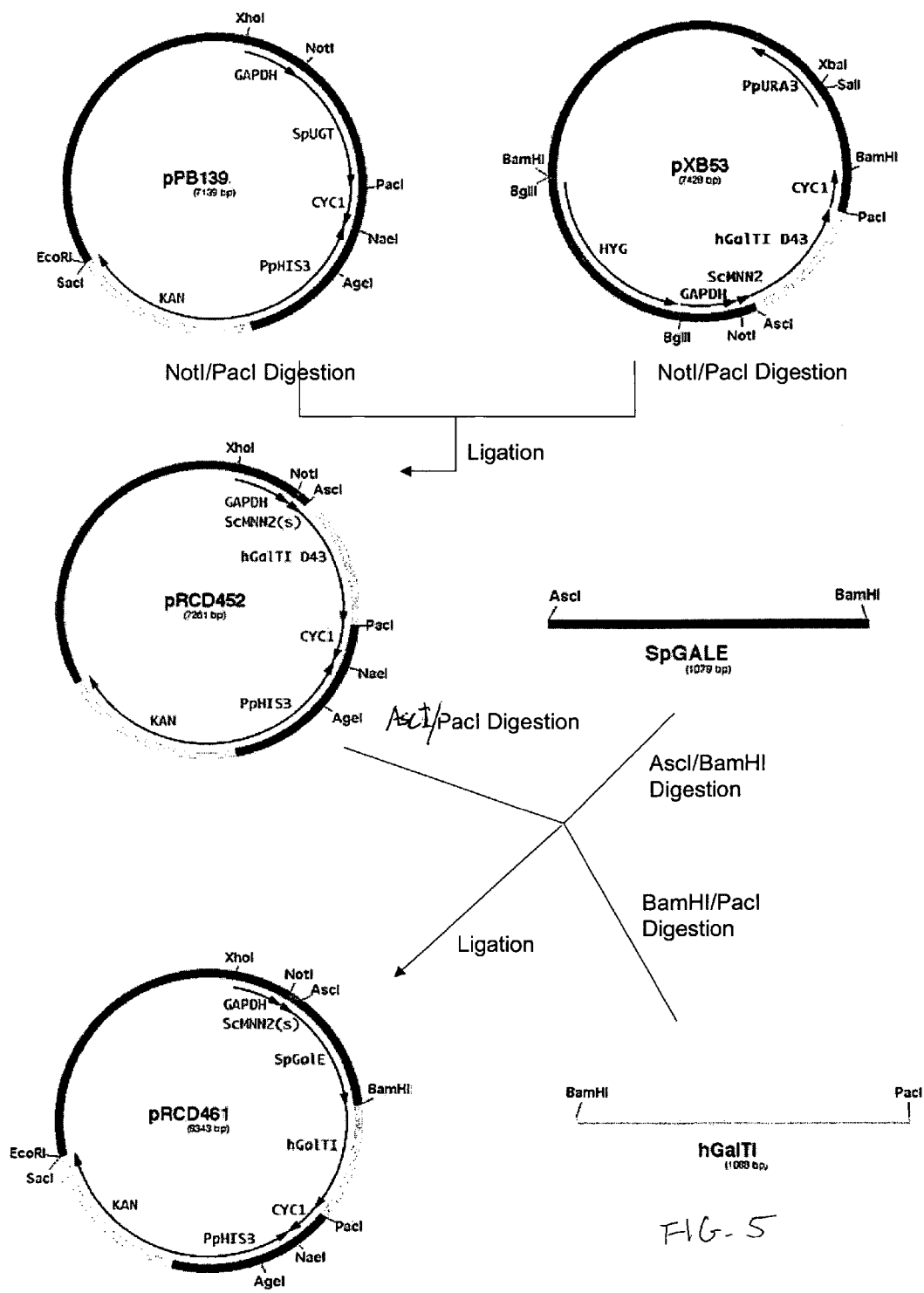
FIG. 5 depicts the construction of a plasmid map of the integration vector pRCD461 encoding the ScMnn2/SpGalE/hGalTI fusion protein.
Figures 15A, 15B:
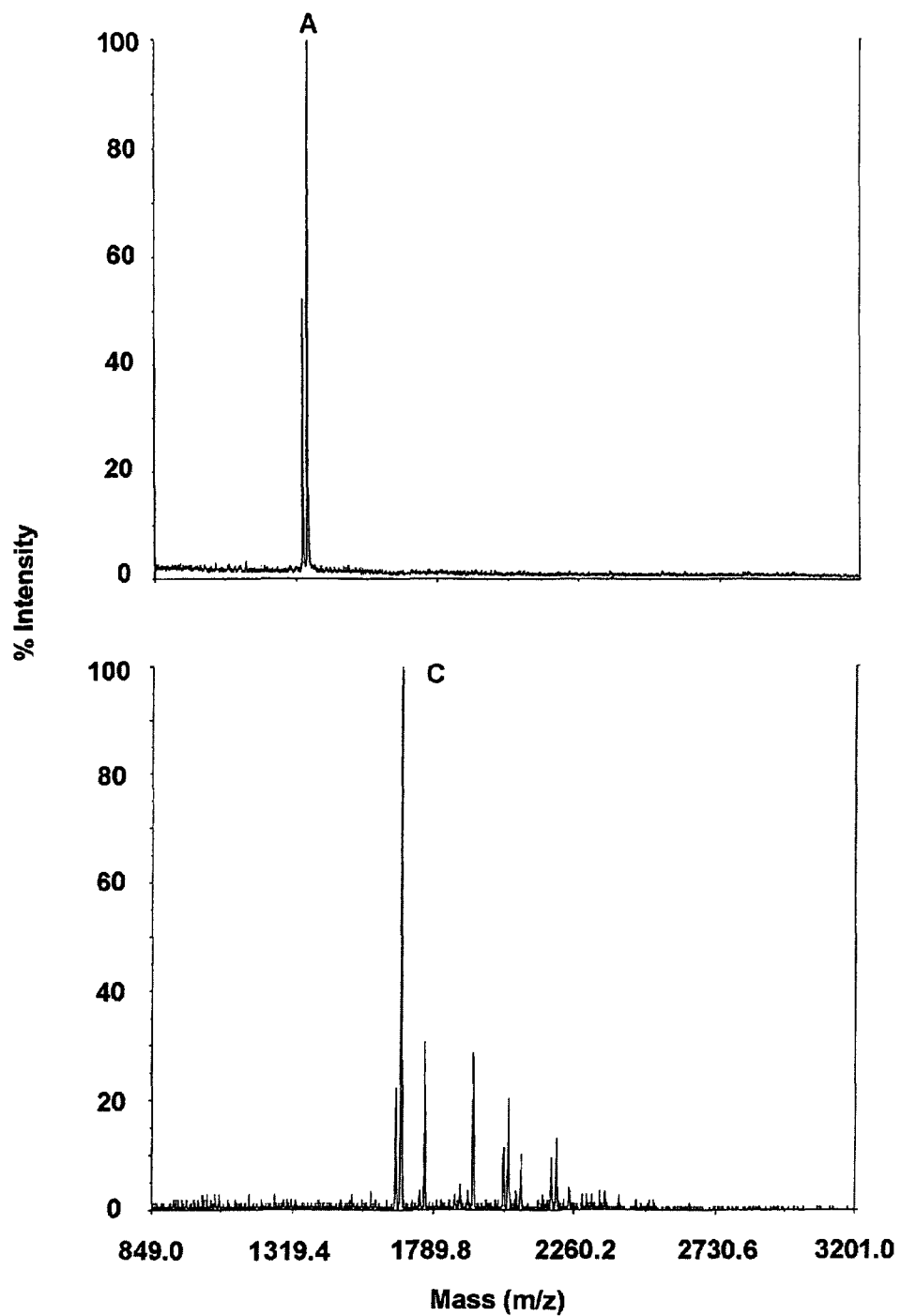
FIG. 15A is a MALDI-TOF-MS analysis depicting the N-glycan $GlcNAc_2Man_3GlcNAc_2$ [A] released from K3 produced in *P. pastoris* YSH-44 (control).
FIG. 15B is a MALDI-TOF-MS analysis of N-glycans released from K3 produced in RDP86 (*P. pastoris* YSH-44 transformed with pRCD461 (Mnn2(s)/SpGalE/hGalTI fusion) displaying a predominant peak at 1679 m/z [C], which corresponds to the mass of the N-glycan $Gal_2GlcNAc_2Man_3GlcNAc_2$.

In a further aspect of the invention, a gene fusion encoding a polypeptide comprising epimerase and galactosyltransferase activities is generated. In one embodiment, a fusion polypeptide comprising a UDP-galactose 4-epimerase and β1,4-GalTI is generated and introduced in a host cell. In a more preferred embodiment, the fusion polypeptide further comprises a leader sequence. For example, a library of leader sequences encoding targeting peptides is ligated in-frame to SpGalE/hGalTI fusion. In an even more preferred embodiment, the fusion polypeptide comprises ScMnn2(s) leader, SpGalE epimerase, and hGalTI. The fusion polypeptide is inserted into a yeast integration plasmid comprising a HYG marker. An example of an epimerase-galactosyltransferase integration plasmid designated pRCD461 is shown in FIG. 5 (Example 8). The epimerase-galactosyltransferase fusion transformant produces approximately 70% galactosylated human-like glycoprotein $Gal_2GlcNAc_2Man_3GlcNAc_2$ (FIG. 15B).

β1,4-Galactosyltransferase; UDP-Galactose 4-Epimerase; UDP-Galactose Transporter Polypeptides In another aspect of the present invention, a single construct encoding polypeptides comprising a β-galactosyltransferase, epimerase and UDP-galactose transporter activities is generated. In one embodiment, a plasmid comprising human β1,4GalT, SpGalE and DmUGT ("triple") is constructed (Example 9). In a preferred embodiment, the transferase polypeptide further comprises a leader sequence, for example, ScMnn2(s) ligated in-frame to hGalTI. All three polypeptides are inserted into a yeast integration plasmid containing a $KAN^R$ marker, preferably with their own promoters and terminators. An example of this "triple" integration plasmid, designated pRCD465, is shown in FIG. 4. In one embodiment, the "triple" integration plasmid comprising the fusion polypeptide is introduced and expressed in a host cell producing terminal GlcNAc residues. *P. pastoris* YSH-44 was transformed with the "triple" integration plasmid and was denoted RDP80.

Figure 14:
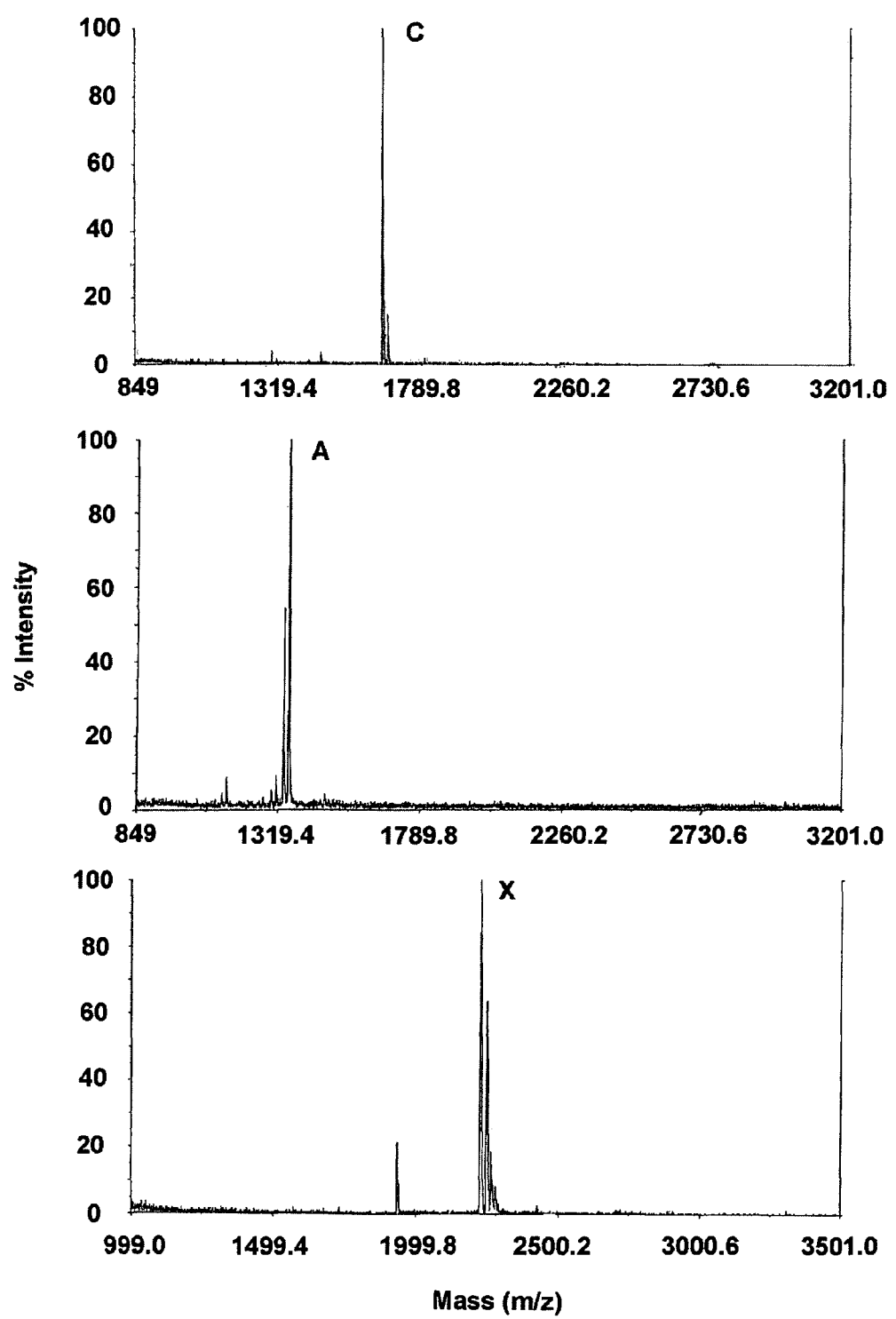
FIG. 14A is a MALDI-TOF-MS analysis of N-glycans released from K3 produced in RDP80 (*P. pastoris* YSH-44 transformed with pRCD465) displaying a predominant peak at 1663 m/z [C], which corresponds to the mass of the N-glycan $Gal_2GlcNAc_2Man_3GlcNAc_2$.
FIG. 14B is a MALDI-TOF-MS analysis of N-glycans released from K3 produced in RDP80 (*P. pastoris* YSH-44 transformed with pRCD465) after β1,4-galactosidase digest displaying a predominant peak at 1340 m/z [A], which corresponds to the mass of the N-glycan $GlcNAc_2Man_3GlcNAc_2$.
FIG. 14C is a MALDI-TOF-MS analysis of N-glycans released from K3 produced in RDP80 and incubated with sialyltransferase in vitro in the presence of CMP-NANA, displaying a predominant peak at 2227 m/z [X], which corresponds to the mass of the N-glycan $NANA_2Gal_2GlcNAc_2Man_3GlcNAc_2$.

To evaluate whether the N-glycans produced in strain RDP80 are the predicted $Gal_2GlcNAc_2Man_3GlcNAc_2$ species, purified K3 secreted from RDP80 was incubated with sialyltransferase in vitro in the presence of CMP-NANA and the resulting N-glycans were released. The MALDI-TOF MS analysis of the N-glycans displayed a predominant peak at 2227 m/z [X], which corresponds to the mass of the complex, terminally sialylated N-glycan $NANA_2Gal_2GlcNAc_2Man_3GlcNAc_2$ (FIG. 14C).

Alternative Production of UDP-Gal

As described previously, the transfer of galactose residues onto N-glycans requires a pool of activated galactose (UDP-Gal). One way to generate such a pool above endogenous levels in a lower eukaryote is the expression of a UDP-galactose 4 epimerase. An alternative route includes the expression of three separate genes: a plasma membrane galactose permease, a galactokinase, and a galactose-1-phosphate uridyl transferase in the absence of UDP-galactose 4 epimerase. Expression of the other three genes of the LeLoir pathway in the absence of the UDP-galactose 4 epimerase, with an exogenous source of galactose, would serve to elevate the endogenous levels of UDP-galactose (Ross et al, 2004). Furthermore, in this embodiment the absence of UDP-galactose 4 epimerase allows the levels of UDP-galactose to be modulated by controlling the exogenous concentration of galactose because the UDP-galactose generated cannot be metabolized apart from addition to substrates such as N-glycans.

A galactose permease is a plasma membrane hexose transporter, which imports galactose from an exogenous source. In one embodiment, the galactose permease gene from *S. cerevisiae*, GAL2 (Genbank: M81879), or any gene encoding a plasma membrane hexose transporter capable of importing galactose is used.

A galactokinase is an enzyme that catalyzes the first step of galactose metabolism, namely the phosphorylation of galactose to galactose-1-phosphate. In another embodiment, the GAL1 gene from *S. cerevisiae* (Genbank: X76078) is used.

Galactose-1-phosphate uridyl transferase catalyzes the second step of galactose metabolism, which is the conversion of UDP-glucose and galactose-1-phosphate to UDP-galactose and glucose-1-phosphate. In another embodiment, any gene encoding galactose-1-phosphate uridyl transferase activity can be used, including *S. cerevisiae* GAL7 (Genbank: M12348).

In a preferred embodiment, the UDP-galactose 4 epimerase encoding gene is deleted from a lower eukaryote capable of metabolizing galactose via the LeLoir pathway.

In a more preferred embodiment, galactose permease, galactokinase, and galactose-1-phosphate uridyl transferase encoding genes are expressed in a lower eukaryotic host cell that is gal (−) and does not express the genes of the LeLoir pathway endogenously (Hittinger et al, 2004).

The advantage of this alternative embodiment is that the absence of UDP-galactose 4-epimerase allows specific control of internal UDP-galactose concentration by the modulation of external galactose at levels below growth inhibitory concentrations.

Increased Galactosylated N-Glycans Production in Genetically Altered Yeast Cells Methods to produce human-like N-glycans in yeast and fungal hosts are provided in WO00200879A3 and WO 03056914A1 and are incorporated herein. The skilled artisan recognizes that routine modifications of the procedures disclosed herein in combination with the above methods may provide improved results in the production of the glycoprotein of interest.

In accordance with the methods of the present invention, *P. pastoris* transformed with at least a β-galactosyltransferase fusion construct pXB53 (Example 4) (FIG. 12) produces complex galactosylated glycans in a detectable moiety. At least 10% of galactose residue is transferred onto a glycoprotein in a host cell. In another embodiment, at least 40% of galactose residue is transferred onto a glycoprotein in a host cell. The expression of an epimerase also increases the level of galactose transfer (FIG. 13). Preferably, at least 60% of galactose residue is transferred onto a glycoprotein in a host cell. The expression of another heterologous glycosylation enzyme, such as UGT, further enhances the cellular production of the desired galactosylated glycoproteins. Surprisingly, expression of one such transporter, the DmUGT increases galactose transfer dramatically (FIG. 11). In the best mode of the embodiment, a host cell transformed with the DmUGT shows at least 90% or higher galactose transfer.

Preferably, the temperature of the yeast host cell is kept at 37° C. to match the temperature optimum of the enzyme.

Additionally, the method also includes isolating these glycoproteins.

Expression of UDPase Activity

As described in WO 02/00879, in humans, nucleotide sugar precursors (e.g. UDP-N-acetylglucosamine, UDP-N-acetylgalactosamine, CMP-N-acetylneuraminic acid, UDP-galactose, etc.) are generally synthesized in the cytosol and transported into the Golgi, where they are attached to the core oligosaccharide by glycosyltransferases. To replicate this process in lower eukaryotes, sugar nucleoside specific transporters have to be expressed in the Golgi to ensure adequate levels of nucleoside sugar precursors (Sommers, 1981; Sommers, 1982; Perez, 1987). A side product of the transfer of sugars onto N-glycans is either a nucleoside diphosphate or monophosphate. While monophosphates can be directly exported in exchange for nucleoside triphosphate sugars by an antiport mechanism, diphospho nucleosides (e.g. GDP) have to be cleaved by phosphatases (e.g. GDPase) to yield nucleoside monophosphates and inorganic phosphate prior to being exported. This reaction appears to be important for efficient glycosylation, as GDPase from *S. cerevisiae* has been found to be necessary for mannosylation. However, the enzyme only has 10% of the activity towards UDP (Berninsone, 1994). Lower eukaryotes often do not have UDP specific diphosphatase activity in the Golgi since they do not utilize UDP-sugar precursors for glycoprotein synthesis in the Golgi.

Engineered yeast strains contain multiple transferase enzymes that utilize UDP-GlcNAc or UDP-galactose as a substrate. This requires the engineering of suitable substrate pools in the yeast Golgi, which in most species does not contain these substrates. However, the endproducts of a transferase reaction utilizing UDP-GlcNAc or UDP-galactose include free UDP. This UDP acts as a potent inhibitor of most transferases that utilize these sugar nucleotides. *S. cerevisiae* expresses two Golgi proteins with nucleoside diphosphatase activity. One, ScGDA1, is highly specific for GDP (Abeijon et al, 1993). The second, ScYND1, is an apyrase and thus capable of hydrolyzing both nucleoside tri- as well as diphosphates and is equally specific for ADP/ATP, GDP/GTP and UDP/UTP (Gao et al, 1999). However, because of the lack of UDP conjugated sugars in the wild-type Golgi and the concomitant lack of transferase enzymes producing UDP as an end product, the possible elevated accumulation of UDP in engineered yeast strain is a significant concern.

Because transfer of galactose residues from the cytosol to the Golgi can be hampered by the lack of UDPase, genetic manipulation to express UDPase may be required for efficient galactose transfer in a lower eukaryotic host cell. Accordingly, in another aspect of the present invention, a method is provided to express, preferably overexpress, a gene encoding for the UDPase. It is contemplated that overexpression of a gene encoding for the UDPase activity increases the availability of the sugar nucleotide UDP-galactose required for galactose transfer onto the acceptor substrates in the Golgi. To raise the level of UDPase activity in the Golgi of a yeast, several possibilities exist. In one embodiment, a gene encoding UDPase activity, e.g., ScGDA1 (NP_010872) is overexpressed, which has some (about 10%) activity towards UDP. In another embodiment, a gene encoding nucleoside diphosphatase activity, e.g., ScYND1 (NP_010920) is overexpressed, which has a higher activity towards UDP compared to GDP, though is not specialized for nucleotide diphosphates. Furthermore, in another embodiment, to achieve the goal of higher UPDase activity in *P. pastoris*, the *S. cerevisiae* GDA1 or YND1 is expressed or the *P. pastoris* homologs of these genes are overexpressed, which are readily identifiable via BLAST homology searches.

Additionally, organisms that utilize these sugar nucleotides are able to convert them to UMP via the action of a nucleotide diphosphatase specific for UDP. An example is the human uridine diphosphatase (UDPase) identified by Wang and Guidotti (AF016032). However, this protein contains two putative transmembrane domains, one at the C-terminus and one at the N-terminus. Accordingly, localization of this protein in the yeast Golgi thus requires fusing the catalytic domain of this protein with a yeast targeting domain.

Other yeasts including *K. lactis* and *S. pombe* utilize UDP-sugars in their Golgi to add GlcNAc and galactose, respectively, to their N-glycans. Both *K. lactis* and *S. pombe* express homologs of ScGDA1, designated KlGDA1 (Lopez-Avalos et al, 2001; CAC21576) and Spgda1 (D'Alessio et al, 2003; NP_593447), respectively, which also have UDPase activity. In case UDP accumulates in engineered yeast strains and proves to be detrimental to the engineered transferases, expression of any or more of these proteins serves to boost UDPase activity to acceptable levels.

Binding Affinity to Asialoglycoprotein Receptors (ASGR)

Another feature of the invention provides less binding affinity to ASGR, which are known to clear asialylated glycoproteins and reduce half-life of a therapeutic protein in the circulatory system. Previous work has shown that glycans having biantennary structures are cleared out less rapidly than glycans having tri or tetra-antennary structures (Stockert, Physiol Rev. 1995 July; 75(3):591-609). In one aspect of the present invention provides glycans on the protein of interest having a single glycoform (e.g., bi-antennary structures) characterized as having terminal galactose residues. Such bi-antennary structures are not readily produced in mammalian cells because of other GnTs that catalyze tri- and tetra-antennary branching reactions. By capping the substrates having terminal GlcNAc residues with galactose residues, other GnTs (e.g. GnT IV, GnT V) are not present to catalyze the transfer of GlcNAcs onto the galactosylated substrates. Accordingly, the present invention provides methods for producing asialylated glycoproteins having less binding affinity to ASGR in comparison to those glycoproteins produced in mammalian hosts. In a more preferred embodiment, the asialylated glycoprotein is characterized by its increased circulatory half-life and bioactivity in vivo in comparison to heterogeneous glycoproteins produced in mammals.

Integration Sites

It is preferable to integrate the nucleic acids encoding the UGT, epimerase and β1,4GalT in a locus that is responsible for mannosyltransferases such as 1,3 mannosyltransferases (e.g. MNN1 in *S. cerevisiae*) (Graham, 1991), 1,2 mannosyltransferases (e.g. KTR/KRE family from *S. cerevisiae*), 1,6 mannosyltransferases (OCH1 from *S. cerevisiae* or *P. pastoris*), mannosylphosphate transferases and their regulators (MNN4, PNO1 and MNN6 from *S. cerevisiae*), vacuolar proteinase A (PEP4), vacuolar protease B (PRB1) GPI-anchored aspartic protease (YPS1) and additional enzymes that are involved in aberrant, immunogenic, i.e. non-human glycosylation reactions.

The mutants with the disrupted locus give rise to a viable phenotype with reduced enzyme activity or eliminated enzyme activity completely. Preferably, the gene locus encoding the initiating α-1,6 mannosyltransferase activity is a prime target for the initial integration of genes encoding glycosyltransferase activity. In a similar manner, one can choose a range of other chromosomal integration sites that, based on a gene disruption event in that locus, are expected to: (1) improve the cell's ability to glycosylate in a more human-like fashion, (2) improve the cell's ability to secrete proteins, (3) reduce proteolysis of foreign proteins and (4) improve other characteristics of the process that facilitate purification or the fermentation process itself.

In an especially preferred embodiment, library DNA is integrated into the site of an undesired gene in a host chromosome, effecting the disruption or deletion of the gene. For example, integration into the sites of the OCH1, MNN1, or MNN4 genes allows the expression of the desired library DNA while preventing the expression of enzymes involved in yeast hypermannosylation of glycoproteins. In other embodiments, library DNA may be introduced into the host via a nucleic acid molecule, plasmid, vector (e.g., viral or retroviral vector), chromosome, and may be introduced as an autonomous nucleic acid molecule or by homologous or random integration into the host genome. In any case, it is generally desirable to include with each library DNA construct at least one selectable marker gene to allow ready selection of host organisms that have been stably transformed. Recyclable marker genes such as URA5 (Yeast. 2003 November; 20(15): 1279-90), which can be selected for or against, are especially suitable.

Generating Additional Sequence Diversity

The method of this embodiment is most effective when a nucleic acid, e.g., a DNA library transformed into the host contains a large diversity of sequences, thereby increasing the probability that at least one transformant will exhibit the desired phenotype. Single amino acid mutations, for example, may drastically alter the activity of glycoprotein processing enzymes (Romero et al., 2000). Accordingly, prior to transformation, a DNA library or a constituent sub-library may be subjected to one or more techniques to generate additional sequence diversity. For example, one or more rounds of gene shuffling, error prone PCR, in vitro mutagenesis or other methods for generating sequence diversity, may be performed to obtain a larger diversity of sequences within the pool of fusion constructs.

Codon Optimization

It is also contemplated that the nucleic acids of the present invention may be codon optimized resulting in one or more changes in the primary amino acid sequence, such as a conservative amino acid substitution, addition, deletion or combination thereof.

Expression Control Sequences

In addition to the open reading frame sequences described above, it is generally preferable to provide each library construct with expression control sequences, such as promoters, transcription terminators, enhancers, ribosome binding sites, and other functional sequences as may be necessary to ensure effective transcription and translation of the fusion proteins upon transformation of fusion constructs into the host organism.

Suitable vector components, e.g., selectable markers, expression control sequences (e.g., promoter, enhancers, terminators and the like) and, optionally, sequences required for autonomous replication in a host cell, are selected as a function of which particular host cell is chosen. Selection criteria for suitable vector components for use in a particular mammalian or a lower eukaryotic host cell are routine. Preferred lower eukaryotic host cells of the invention include *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia sp., Saccharomyces cerevisiae, Saccharomyces sp., Hansenula polymorpha, Kluyveromyces sp., Kluyveromyces lactis, Candida albicans, Aspergillus nidulans, Aspergillus niger, Aspergillus oryzae, Trichoderma reesei, Chrysosporium lucknowense, Fusarium sp., Fusarium gramineum, Fusarium venenatum, Physcomitrella patens* and *Neurospora crassa*.

Where the host is *Pichia pastoris*, suitable promoters include, for example, the AOX1, AOX2, GAPDH, OCH1, SEC4, D2 and P40 promoters.

Selectable Markers

It is also preferable to provide each construct with at least one selectable marker, such as a gene to impart drug resistance or to complement a host metabolic lesion. The presence of the marker is useful in the subsequent selection of transformants; for example, in yeast the URA5, URA3, HIS4, SUC2, G418, BLA, or SH BLE genes may be used. A multitude of selectable markers are known and available for use in yeast, fungi, plant, insect, mammalian and other eukaryotic host cells.

Transformation

In yeast, any convenient method of DNA transfer may be used, such as electroporation, the lithium chloride method, or the spheroplast method. In filamentous fungi and plant cells, conventional methods include particle bombardment, electroporation and agrobacterium mediated transformation. To produce a stable strain suitable for high-density culture (e.g., fermentation in yeast), it is desirable to integrate the fusion constructs into the host chromosome. In a preferred embodiment, integration occurs via homologous recombination, using techniques well-known in the art. Preferably, stable genetic modification of *P. pastoris* occurs via a double crossover event. Nett et al., Yeast. 2003 November; 20(15):1279-90. For example, the heterologous enzyme activities are provided with flanking sequences homologous to sequences of the host organism and successively transformed reusing a single marker. In this manner, integration occurs at a defined site in the host genome using a recyclable marker.

Screening and Selection Processes

After transformation of the host strain with the heterologous enzymes, transformants displaying a desired glycosylation phenotype are selected. Selection may be performed in a single step or by a series of phenotypic enrichment and/or depletion steps using any of a variety of assays or detection methods. Phenotypic characterization may be carried out manually or using automated high-throughput screening equipment. Commonly, a host microorganism displays protein N-glycans on the cell surface, where various glycoproteins are localized.

One may screen for those cells that have the highest concentration of terminal GlcNAc on the cell surface, for example, or for those cells which secrete the protein with the highest terminal GlcNAc content. Such a screen may be based on a visual method, like a staining procedure, the ability to bind specific terminal GlcNAc binding antibodies or lectins conjugated to a marker (such lectins are available from E.Y. Laboratories Inc., San Mateo, Calif.), the reduced ability of specific lectins to bind to terminal mannose residues, the ability to incorporate a radioactively labeled sugar in vitro, altered binding to dyes or charged surfaces, or may be accomplished by using a Fluorescence Assisted Cell Sorting (FACS) device in conjunction with a fluorophore labeled lectin or antibody (Guillen, 1998).

Accordingly, intact cells may be screened for a desired glycosylation phenotype by exposing the cells to a lectin or antibody that binds specifically to the desired N-glycan. A wide variety of oligosaccharide-specific lectins are available commercially (e.g., from EY Laboratories, San Mateo, Calif.). Alternatively, antibodies to specific human or animal N-glycans are available commercially or may be produced using standard techniques. An appropriate lectin or antibody may be conjugated to a reporter molecule, such as a chromophore, fluorophore, radioisotope, or an enzyme having a chromogenic substrate (Guillen et al., 1998. *Proc. Natl. Acad. Sci. USA* 95(14): 7888-7892)).

Screening may then be performed using analytical methods such as spectrophotometry, fluorimetry, fluorescence activated cell sorting, or scintillation counting. In other cases, it may be necessary to analyze isolated glycoproteins or N-glycans from transformed cells. Protein isolation may be carried out by techniques known in the art. In a preferred embodiment, a reporter protein is secreted into the medium and purified by affinity chromatography (e.g. Ni-affinity or glutathione-S-transferase affinity chromatography). In cases where an isolated N-glycan is preferred, an enzyme such as endo-β-N-acetylglucosaminidase (Genzyme Co., Boston, Mass.; New England Biolabs, Beverly, Mass.) may be used to cleave the N-glycans from glycoproteins. Isolated proteins or N-glycans may then be analyzed by liquid chromatography (e.g. HPLC), mass spectroscopy, or other suitable means. U.S. Pat. No. 5,595,900 teaches several methods by which cells with desired extracellular carbohydrate structures may be identified. In a preferred embodiment, MALDI-TOF mass spectrometry is used to analyze the cleaved N-glycans.

Prior to selection of a desired transformant, it may be desirable to deplete the transformed population of cells having undesired phenotypes. For example, when the method is used to engineer a functional mannosidase activity into cells, the desired transformants will have lower levels of mannose in cellular glycoprotein. Exposing the transformed population to a lethal radioisotope of mannose in the medium depletes the population of transformants having the undesired phenotype, i.e. high levels of incorporated mannose (Huffaker T C and Robbins P W., *Proc Natl Acad Sci USA*. 1983 December; 80(24):7466-70). Alternatively, a cytotoxic lectin or antibody, directed against an undesirable N-glycan, may be used to deplete a transformed population of undesired phenotypes (e.g., Stanley P and Siminovitch L. *Somatic Cell Genet* 1977 July; 3(4):391-405). U.S. Pat. No. 5,595,900 teaches several methods by which cells with a desired extracellular carbohydrate structures may be identified. Repeatedly carrying out this strategy allows for the sequential engineering of more and more complex glycans in lower eukaryotes.

To detect host cells having on their surface a high degree of the human-like N-glycan intermediate $Gal_2GlcNAc_2Man_3GlcNAc_2$, for example, one may select for transformants that allow for the most efficient transfer of Galactose by GalT from UDP-Galactose in an in vitro cell assay. This screen may be carried out by growing cells harboring the transformed library under selective pressure on an agar plate and transferring individual colonies into a 96-well microtiter plate. After growing the cells, the cells are centrifuged, the cells resuspended in buffer, and after addition of UDP-Galactose and GalT, the release of UDP is determined either by HPLC or an enzyme linked assay for UDP. Alternatively, one may use radioactively labeled UDP-Galactose and GalT, wash the cells and then look for the release of radioactive Galactose by β-galactosidase. All this may be carried manually or automated through the use of high throughput screening equipment. Transformants that release more UDP, in the first assay, or more radioactively labeled Galactose in the second assay, are expected to have a higher degree of $Gal_2GlcNAc_2Man_3GlcNAc_2$ on their surface and thus constitute the desired phenotype. Similar assays may be adapted to look at the N-glycans on secreted proteins as well.

Alternatively, one may use any other suitable screen such as a lectin binding assay that is able to reveal altered glycosylation patterns on the surface of transformed cells. In this case the reduced binding of lectins specific to terminal mannoses may be a suitable selection tool. *Galantus nivalis* lectin binds specifically to terminal α-1,3 mannose, which is expected to be reduced if sufficient mannosidase II activity is present in the Golgi. One may also enrich for desired transformants by carrying out a chromatographic separation step that allows for the removal of cells containing a high terminal mannose content. This separation step would be carried out with a lectin column that specifically binds cells with a high terminal mannose content (e.g., *Galantus nivalis* lectin bound to agarose, Sigma, St. Louis, Mo.) over those that have a low terminal mannose content.

Host Cells

Although the present invention is exemplified using *P. pastoris* as a host organism, it is understood by those skilled in the art that other eukaryotic host cells, including other species of yeast and fungal hosts, may be altered as described herein to produce human-like glycoproteins. Such hosts include preferably *Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Physcomitrella patens* and *Neurospora crassa*.

The techniques described herein for identification and disruption of undesirable host cell glycosylation genes, e.g. OCH1, is understood to be applicable for these and/or other homologous or functionally related genes in other eukaryotic host cells such as other yeast and fungal strains (See WO 02/00879). Additionally, other preferred host cells are deficient in Alg3p encoding for Dol-P-Man:$Man_5GlcNAc_2$-PP-Dol mannosyltransferase activity (See WO 03/056914).

Preferred host cells are yeast and filamentous fungal hosts, which inherently lack β1,4-galactose linkages, fucose, and terminal sialic acid. Unlike the N-glycans of mammalian glycoproteins these sugars are not usually found on glycoproteins produced in yeast and filamentous fungi. The present invention provides methods for engineering host cells to produce galactose residues onto glycoproteins and essentially lack fucose and sialic acid residues on the glycoproteins. In another embodiment, those host cells that produce fucose or sialic acid can be modified to have reduced or eliminated fucosyltransferase activity or sialyltransferase activity. The glycoprotein compositions produced from the host of the present invention are, therefore, essentially free of fucose and sialic acid residues. A significant advantage of the present invention is that the host cells produce galactosylated, fucose-free and sialic acid-free glycoproteins without ex vivo modification with fucosidase and sialidase treatment.

Other preferred host cells include fungal hosts that lack mannosylphosphorylation with respect to glycans (U.S. Ser. No. 11/020,808). Still other preferred host cells include fungal hosts that lack β-mannosylation with respect to glycans (U.S. Ser. No. 60/566,736).

Another aspect of the present invention thus relates to a non-human eukaryotic host strain expressing glycoproteins comprising modified N-glycans that resemble those made by human-cells. Performing the methods of the invention in species other than yeast and fungal cells is thus contemplated and encompassed by this invention. It is contemplated that a combinatorial nucleic acid library of the present invention may be used to select constructs that modify the glycosylation pathway in any eukaryotic host cell system. For example, the combinatorial libraries of the invention may also be used in plants, algae and insects, and in other eukaryotic host cells, including mammalian and human cells, to localize proteins, including glycosylation enzymes or catalytic domains thereof, in a desired location along a host cell secretory pathway. Preferably, glycosylation enzymes or catalytic domains and the like are targeted to a subcellular location along the host cell secretory pathway where they are capable of functioning, and preferably, where they are designed or selected to function most efficiently.

Examples of modifications to glycosylation which can be affected using a method according to this embodiment of the invention are: (1) engineering a eukaryotic host cell to trim mannose residues from $Man_8GlcNAc_2$ to yield a $Man_5GlcNAc_2$ N-glycan; (2) engineering eukaryotic host cell to add an N-acetylglucosamine (GlcNAc) residue to $Man_5GlcNAc_2$ by action of GlcNAc transferase I; (3) engineering a eukaryotic host cell to functionally express an enzyme such as an N-acetylglucosaminyl Transferase (GnTI, GnTII, GnTIII, GnTIV, GnTV, GnTVI, GnTIX), mannosidase II, fucosyltransferase (FT), galactosyl transferase (GalT) or a sialyltransferase (ST).

By repeating the method, increasingly complex glycosylation pathways can be engineered into a target host, such as a lower eukaryotic microorganism. In one preferred embodiment, the host organism is transformed two or more times with DNA libraries including sequences encoding glycosylation activities. Selection of desired phenotypes may be performed after each round of transformation or alternatively after several transformations have occurred. Complex glycosylation pathways can be rapidly engineered in this manner.

Target Glycoproteins

The methods described herein are useful for producing glycoproteins, especially glycoproteins used therapeutically in humans. Glycoproteins having specific glycoforms may be especially useful, for example, in the targeting of therapeutic proteins. For example, mannose-6-phosphate has been shown to direct proteins to the lysosome, which may be essential for the proper function of several enzymes related to lysosomal storage disorders such as Gaucher's, Hunter's, Hurler's, Scheie's, Fabry's and Tay-Sachs disease, to mention just a few. Likewise, the addition of one or more sialic acid residues to a glycan side chain may increase the lifetime of a therapeutic glycoprotein in vivo after administration. Accordingly, host cells (e.g., lower eukaryotic or mammalian) may be genetically engineered to increase the extent of terminal sialic acid in glycoproteins expressed in the cells. Alternatively, sialic acid may be conjugated to the protein of interest in vitro prior to administration using a sialic acid transferase and an appropriate substrate. Changes in growth medium composition may be employed in addition to the expression of enzyme activities involved in human-like glycosylation to produce glycoproteins more closely resembling human forms (S. Weikert, et al., *Nature Biotechnology*, 1999, 17, 1116-1121; Werner, Noe, et al 1998 *Arzneimittelforschung* 48(8):870-880; Weikert, Papac et al., 1999; Andersen and Goochee 1994 *Cur. Opin. Biotechnol.* 5: 546-549; Yang and Butler 2000 *Biotechnol. Bioengin.* 68(4): 370-380). Specific glycan modifications to monoclonal antibodies (e.g. the addition of a bisecting GlcNAc) have been shown to improve antibody dependent cell cytotoxicity (Umana P., et al. 1999), which may be desirable for the production of antibodies or other therapeutic proteins.

Therapeutic proteins are typically administered by injection, orally, pulmonary, or other means. Examples of suitable target glycoproteins which may be produced according to the invention include, without limitation: erythropoietin, cytokines such as interferon-α, interferon-β, interferon-γ, interferon-ω, and granulocyte-CSF, GM-CSF, coagulation factors such as factor VIII, factor IX, and human protein C, antithrombin III, thrombin, soluble IgE receptor α-chain, IgG, IgG fragments, IgG fusions, IgM, interleukins, urokinase, chymase, and urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1-antitrypsin, α-feto proteins, DNase II, kringle 3 of human plasminogen, glucocerebrosidase, TNF binding protein 1, follicle stimulating hormone, cytotoxic T lymphocyte associated antigen 4-Ig, transmembrane activator and calcium modulator and cyclophilin ligand, soluble TNF receptor Fc fusion, glucagon like protein 1 and IL-2 receptor agonist.

Secretory Signal Sequence

It is also preferred to associate a nucleic acid sequence encoding a secretory signal with a sequence of interest encoding the glycoprotein. The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway. To direct a polypeptide into the secretory pathway of a host cell, a secretory signal sequence (also known as a leader sequence, prepro sequence or pre sequence) is provided in an expression vector. The secretory signal sequence may be that of, without limitation, a wild-type sequence related to a glycoprotein, sequence encoding *S. cerevisiae* Suc2 signal sequence, sequence encoding *Pichia* Pho2 signal sequence, sequence encoding *Pichia* Prc1 signal sequence, sequence encoding *S. cerevisiae* alpha-mating factor (αMF) signal sequence, sequence encoding bovine lysozyme C signal sequence. The secretory signal sequence is operably linked to a nucleic acid sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (See, e.g., Welch et al., U.S. Pat. No. 5,037,743; Holland et al., U.S. Pat. No. 5,143,830).

Alternatively, the secretory signal sequence contained in the polypeptides of the present invention is used to direct other polypeptides into the secretory pathway. The present invention provides for such fusion polypeptides. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein, such as a receptor. Such fusions may be used in vivo or in vitro to direct peptides through the secretory pathway.

Glycoproteins produced by the methods of the present invention can be isolated by techniques well-known in the art. The desired glycoproteins are purified and separated by methods such as fractionation, ion exchange, gel filtration, hydrophobic chromatography and affinity chromatography.

The following are examples which illustrate the compositions and methods of this invention. These examples should not be construed as limiting: the examples are included for the purposes of illustration only.

Example 1

Construction of Promoter Cassettes and Expression Vectors

The 800 bp promoter for the PpOCH1 gene was amplified using primers RCD48 (SEQ ID NO:15) (5'-TATGCGGC- CGCGGCTGATGATATTTGCTACGA-3') and RCD134 (SEQ ID NO:16) (5'-CCTCTCGAGTGGACACAG-GAGACTCAGAAACAG-3') and the 400 bp promoter for the PpSEC4 gene was amplified using primers RCD156 (SEQ ID NO:17) (5'-CTTCTCGAGGGAAGTAAAGTTGGC-GAAACTT-3') and RCD157 (SEQ ID NO:18) (5'-CT-TAGCGGCCGCGATTGTTCGTTTGAGTAGTTT-3'). The PCR products were cloned into the pCR2.1 cloning vector (Invitrogen) and sequenced. The OCH1 and SEC4 promoters were then subcloned into the vector pJN261 (Nett et al., Yeast. 2003 November; 20(15):1279-90) in place of the GAPDH promoter using the introduced XhoI/NotI restriction sites to create plasmids pRCD360 and pRCD362, respectively.

The PpHIS3 promoter was PCR amplified using primers RCD152 (SEQ ID NO:19) (5'-CTTCTCGAGGGCAT-TCAAAGAAGCCTTGGG-3') and RCD 153 (SEQ ID NO:20) (5'-CTTAGCGGCCGCTGAGTGGTCATGTGG-GAACTT-3'), cloned into plasmid pCR2.1 and sequenced. The XhoI/NotI sites were then used to subclone the PpHIS3 promoter into plasmid pTA18 to replace the PpPMA1 strong promoter with the weaker PpHIS3 promoter and create plasmid pRCD351, which is a $NAT^R$ plasmid that rolls into the PpHIS3 promoter.

A portion of the PpHIS3 gene was amplified using primers RCD301 (SEQ ID NO:21) (5'-CCTGGATCCAACAGAC-TACAATGACAGGAG-3') and RCD302 (SEQ ID NO:22) (5'-CCTGCATGCCTCGAGCTTGCCG-GCGTCTAAATAGCCGTTGAAG-3') and inserted into pUC19 using the BamHI/SphI restriction sites to create plasmid pRCD391. This vector contains a 1.2 Kb portion of the PpHIS3 locus as well as XhoI and NgoMIV sites engineered into the primer RCD302 (SEQ ID NO:22). The $G418^R$ gene was inserted as a BglII/SacI fragment from pUG6 (Wach et al., 1994) into the BamHI/SacI sites of pRCD391 to create pRCD392.

A 1.2 Kb portion of the PpTRP1 gene was amplified from P. pastoris genomic DNA with primers RCD307 (SEQ ID NO:23) (5'-CCTGTCGACGCTGCCGGCAAG CTCGAGTTTAAGCGGTGCTGC-3') and RCD308 (SEQ ID NO:24) (5'-CCT GGATCCTTTGGCAAAAACCAGCCCTGGTGAG-3'). The amplified fragment was inserted into pUC19 using BamHI/SalI sites to create plasmid pRCD399. The PAT gene conferring resistance to phosphinothricin was released from plasmid pAG29 (Goldstein and McCusker, 1999) using BglII/SacI and inserted into pRCD399 digested with BamHI/SacI to create the PpTRP1/PAT roll-in plasmid pRCD401.

Example 2

Cloning of Galactose Transporters

*Schizosaccharomyces pombe* UDP Galactose Transporter

The S. pombe gene encoding the UDP Galactose Transporter (SpGMS1+, Genbank AL022598) referred to as SpUGT was PCR amplified from S. pombe genomic DNA (ATCC24843) in two pieces to eliminate a single intron. Primers RCD164 (SEQ ID NO:7) (5'-CCTTGCGGCCG-CATGGCTGTCAAGGGCGACGATGTCAAA-3') and RCD177 (SEQ ID NO:8) (5'-ATTCGAGAATAGTTAAGT-GTCAAAATCAATGCACTATTT-3') were used to amplify the 5' 96 bp of the gene and primers RCD176 (SEQ ID NO:9) (5'-AAAATAGTGCATTGATTTTGACACT-TAACTATTCTCGAAT-3') and RCD 165 (SEQ ID NO:10) (5'-CCTTTTAATTAATTAATGCTTATGAT-CAACGTCCTTAGC-3') to amplify the 3' 966 bp. Subsequently, primers RCD164 (SEQ ID NO:7) and RCD165 (SEQ ID NO:10) were used to overlap the two amplified products into a single PCR fragment comprising one contiguous open reading frame with NotI and PacI sites introduced at the ends. This PCR product was cloned into the pCR2.1 vector (Invitrogen) and sequenced. The NotI and PacI sites were then used to subclone this gene into plasmid pJN335, which contains a cassette that fuses a gene downstream of the P. pastoris GAPDH promoter. The 400 bp PpOCH1 transcriptional terminator was then PCR amplified using primers RCD202 (SEQ ID NO:25) (5'-TCCTTAATTAAA-GAAAGCTAGAGTAAAATAGAT-3') and RCD203 (SEQ ID NO:26) (5'-TCCCTCGAGGATCATGTTGATCAACT-GAGACCG-3') and cloned into pCR2.1. Subsequently a triple ligation was performed to insert the GAPDH promoter/SpUGT gene fusion as an XhoI/PacI fragment and the PpOCH1-TT as a PacI/XhoI fragment into a single XhoI site in plasmid pTA18 to create plasmid pRCD257. The new plasmid, pRCD257, is a $NAT^R$ containing vector that contains the GAPDH-SpGALE-OCH1TT fusion along with a second cassette that contains a truncated version of the human GnTII gene fused to the ScVAN1 transmembrane domain driven by the PpPMA1 promoter.

The SpUGT gene was also inserted into the NotI/PacI sites of pRCD360 with the OCH1 promoter and pRCD362 with the SEC4 promoter to create plasmids pRCD385 and pRCD387, respectively. The $P_{OCH1}$-SpUGT-PpCYC1TT cassette from pRCD385 and $P_{SEC4}$-SpUGT-PpCYC1TT cassette from pRCD387 were inserted into the pRCD392 HIS3/$G418^R$ roll-in vector using XhoI/NgoMIV to create P. pastoris HIS3/$G418^R$ roll-in expression plasmids pRCD393 and pRCD394, respectively.

*Drosophila melanogaster* UDP Galactose Transporter

The D. melanogaster gene encoding the UDP Galactose Transporter (Genbank BAB62747) referred to as DmUGT was PCR amplified from a D. melanogaster cDNA library (UC Berkeley Drosophila Genome Project, ovary λ-ZAP library GM) and cloned into the pCR2.1 PCR cloning vector and sequenced. Primers DmUGT-5' (SEQ ID NO:11) (5'-GGCTCGAGCGGCCGCCACCATGAATAG-CATACACATGAACGCCAATACG-3') and DmUGT-3' (SEQ ID NO:12) (5'-CCCTCGAGTTAATTAACTA-GACGCGCGGCAGCAGCTTCTCCTCATCG-3') were used to amplify the gene, which introduced NotI and PacI sites at the 5' and 3' ends, respectively. The NotI and PacI sites were then used to subclone this gene fused downstream of the PpOCH1 and promoter at the NotI/PacI sites in pRCD393 to create plasmid pSH263.

*Homo sapiens* UDP Galactose Transporter

The H. sapiens genes encoding the UDP Galactose Transporter 1 (Genbank #BAA95615) and UDP Galactose Transporter 2 (Genbank #BAA95614) referred to as hUGT1 and hUGT2, respectively, were amplified from human prostate cDNA (marathon ready dDNA, Clontech). The hUGT1 gene was amplified with primers hUGT1-5' (SEQ ID NO:27) (5'-GGCTCGAGCGGCCGCCACCATGGCAGCG-GTTGGGGCTGGTGGTTC-3') and hUGT1-3' (SEQ ID NO:28) (5'-CCCTCGAGTTAATTAATCACTTCACCAG-CACTGACTTTGGCAG-3') and the hUGT2 gene was amplified with primers hUGT2-5' (SEQ ID NO:29) (5'-GGCTCGAGCGGCCGCCACCATGGCAGCG-GTTGGGGCTGGTGGTTC-3') and hUGT2-3' (SEQ ID NO:30) (5'-CCCTCGAGTTAATTAACTAGGAACCCT-TCACCTTGGTGAGCAAC-3'). The PCR products were cloned into the pCR2.1 vector (Invitrogen, Carlsbad, Calif.) and sequenced. The hUGT1 and hUGT2 genes were subsequently inserted into pRCD393 downstream of the PpOCH1 promoter using NotI/PacI to create plasmids pSH264 and pSH262, respectively.

Example 3

Cloning UDP-Galactose-4-Epimerase Genes

*S. cerevisiae* UDP-Galactose 4-Epimerase

The *S. cerevisiae* gene encoding UDP-galactose 4-epimerase (ScGAL10) was PCR amplified from *S. cerevisiae* genomic DNA using primers RCD270 (SEQ ID NO:31) (5'-TAGCGGCCGCATGACAGCTCAGTTA-CAAAGTGAAAG-3') and RCD271 (SEQ ID NO:32) (5'-CGTTAATTAATCAGGAAAATCTGTAGACAATCTTGG-3'). The resulting PCR product was cloned into pCR2.1 and sequenced.

The ScGAL10 gene was then subcloned using the NotI/PacI sites into plasmids pRCD393 and pRCD394 to create plasmids pRCD395 and pRCD396, respectively and also into plasmids pRCD402 and pRCD403 to create plasmids pRCD404 and pRCD405, respectively. Plasmids pRCD402 and pRCD403 are expression vectors containing the *P. pastoris* OCH1 and SEC4 promoters, respectively, and the PpCYC1 terminator and convenient restriction sites that were used to fuse the epimerases with these promoters and create a cassette that could be collectively moved into another plasmid.

*Homo sapiens* UDP-Galactose 4-Epimerase

The *H. sapiens* gene encoding UDP-galactose 4-epimerase (Thoden et al., (2001) JBC Vol. 276 (18) 15131-15136), referred to as hGALE was PCR amplified from human kidney cDNA (marathon ready cDNA, Clontech) using primers GD7 (SEQ ID NO:33) and GD8 (SEQ ID NO:34) with NotI and PacI sites respectively, cloned into pCR2.1 and sequenced. The hGALE gene was then subcloned using NotI/PacI sites into plasmids pRCD406 and pRCD407 to create plasmids pRCD427 and pRCD428, respectively.

*S. pombe* UDP-Galactose 4-Epimerase

Primers GALE2-L (SEQ ID NO:35) and GALE2-R (SEQ ID NO:36) were used to amplify the SpGALE gene from *S. pombe* (ATCC24843) genomic DNA. The amplified product was cloned into pCR2.1 and sequenced. Sequencing revealed the presence of an intron (175 bp) at the +66 position.

To eliminate the intron, upstream primer GD1 (SEQ ID NO:37) (94 bases) was designed. It has a NotI site, 66 bases upstream of the intron, followed by 20 bases preceding the intron. GD2 (SEQ ID NO:38) is the downstream primer and has a PacI site. Primers GD1 (SEQ ID NO:37) and GD2 (SEQ ID NO:38) were used to amplify the SpGALE intronless gene from the pCR2.1 subclone and the product cloned again into pCR2.1 and sequenced.

Example 4

Cloning of β-1,4-Galactosyltransferase Genes

*Homo sapiens* β-1,4-Galactosyltransferase I

The *H. sapiens* α-1,4-galactosyltransferase I gene (hGalTI, Genbank AH003575) was PCR amplified from human kidney cDNA (marathon ready cDNA, Clontech) using primers RCD192 (SEQ ID NO:1) (5'-GCCGCGACCT-GAGCCGCCTGCCCCAAC-3') and RCD186 (SEQ ID NO:2) (5'-CTAGCTCGGTGTCCCGATGTCCACTGT-3'). This PCR product was cloned into pCR2.1 vector (Invitrogen, Carlsbad, Calif.) and sequenced. From this clone, a PCR overlap mutagenesis was performed for three purposes: 1) to remove a NotI site within the open reading frame while maintaining the wild-type protein sequence, 2) to truncate the protein immediately downstream of the endogenous transmembrane domain, 3) and to introduce AscI and PacI sites at the 5' and 3' ends for modular cloning. To do this, the 5' end of the gene up to the NotI site was amplified using primers RCD198 (SEQ ID NO:3) (5'-CTTAGGCGCGCCGGCCGC-GACCTGAGCCGCCTGCCC-3') and RCD201 (SEQ ID NO:4) (5'-GGGGCATATCTGCCGCCCATC-3') and the 3' end was amplified with primers RCD200 (SEQ ID NO:5) (5'-GATGGGCGGCAGATATGCCCC-3') and RCD199 (SEQ ID NO:6) (5'-CTTCTTAATTAACTAGCTCGGT-GTCCCGATGTCCAC-3'). The products were overlapped together with primers 198 and 199 to resynthesize the ORF with the wild-type amino acid sequence while eliminating the NotI site. The new truncated hGalTI PCR product was cloned into pCR2.1 vector (Invitrogen, Carlsbad, Calif.) and sequenced. The introduced AscI/PacI sites were then used to subclone the fragment into plasmid pRCD259, which is a PpURA3/HYG$^R$ roll-in vector, to create pRCD260. A library of yeast targeting sequence transmembrane domains as described in WO 02/00879, which is incorporated by reference, was ligated into the NotI/AscI sites located upstream of the hGalTI gene to create plasmids pXB20-pXB67.

*Homo sapiens* β-1,4-Galactosyltransferase II

A truncated form of the *H. sapiens* β-1,4-galactosyltransferase II gene (hGalTII, Genbank AF038660) was PCR amplified from human kidney cDNA (marathon ready cDNA, Clontech) using primers RCD292 (SEQ ID NO:39) (5'-CTTAGGCGCGCCCAGCACCTGGCCTTCTTCAGC-3') and RCD293 (SEQ ID NO:40) (5'-CTTGTTAATTAATCAGC-CCCGAGGGGGCCACGACGG-3'), cloned into plasmid pCR2.1 and sequenced. This truncated clone, which eliminates part of the gene encoding the N-terminal transmembrane domain, was subcloned using the introduced AscI/PacI sites into vector pXB53 in place of hGalTI to create plasmid pRCD378. The plasmid, containing the gene fusion of the truncated hGalTII with the transmembrane domain/leader sequence-encoding portion of the *S. cerevisiae* MNN2 gene is driven by the PpGAPDH promoter.

*Homo sapiens* β-1,4-Galactosyltransferase III

A truncated form of the *H. sapiens* β-1,4-galactosyltransferase III gene (hGalTIII, Genbank AF038661) was PCR amplified from human kidney cDNA (marathon ready cDNA, Clontech) using primers RCD294 (SEQ ID NO:41) (5'-CTTAGGCGCGCCCGAAGTCTCAGTGCCCTATTTGGC-3') and RCD295 (SEQ ID NO:42) (5'-CTTGTTAATTAAT-CAGTGTGAACCTCGGAGGGCTGT-3'), cloned into plasmid pCR2.1 and sequenced. This truncated clone, which eliminates part of the gene encoding the N-terminal transmembrane domain, was subcloned using the introduced AscI/PacI sites into vector pXB53 in place of hGalTI to create plasmid pRCD381. This plasmid now contains a gene fusion of the truncated hGalTIII with the transmembrane domain/leader sequence-encoding portion of the *S. cerevisiae* MNN2 gene driven by the PpGAPDH promoter.

Example 5

Expression of hGalT1 with SpUGT in a Strain Producing Complex N-Glycans

The pRCD257 plasmid containing the human GnTII gene and the SpGMS1+ gene (SpUGT) was introduced into strain RDP27. RDP27 is a mutant strain of *P. pastoris* that has och1 and alg3 deletions, and that has been transformed with plasmids pSH49 and pPB104 which contain active fusion constructs of mouse Mannosidase IB and human GnTI, respectively as well as plasmid pPB103, which contains the *K. lactis* UDP-GlcNAc transporter and pBK64 which contains the reporter protein K3 (Choi et al. 2003). After selection on nourseothricin, 16 transformants were selected to determine the glycosylation of the expressed reporter protein K3. In two of these transformants, the expected complex human glycosylation structure $GlcNAc_2Man_3GlcNAc_2$ was observed and these strains were designated RDP30-10 (FIG. 8A) and RDP30-13. A portion of the hGalTI gene/leader fusion plasmid library was transformed into strain RDP30-10 and transformants were selected on minimal medium containing hygromycin. N-glycans released from K3 secreted by the resulting strains were analyzed on MALDI-TOF MS. A molecular shift in mass consistent with the addition of one galactose sugar was observed on N-glycans from transformants of two different leader constructs, pXB53 and pXB65. The first, pXB53 consists of hGalTI fused to the ScMnn2(s) leader (referred to here as ScMnn2(s)/hGalTI) and the other was a fusion with the ScMnn1(m) leader. Analysis of the N-glycans released from K3 from RDP37 (RDP30-10 transformed with pXB53) by MALDI-TOF revealed approximately 10-20% $GlcNAc_2Man_3GlcNAc_2$ being converted to $GalGlcNAc_2Man_3GlcNAc_2$ and a lesser amount (1-2%) to $Gal_2GlcNAc_2Man_3GlcNAc_2$ (pXB53, FIG. 8B). A lesser amount of conversion (3-5%) to $GalGlcNAc_2Man_3GlcNAc_2$ but no observable $Gal_2GlcNAc_2Man_3GlcNAc_2$ was observed for the second fusion (pXB65).

Example 6

Expression of hGalTI and ScGAL10 in a Strain Producing Hybrid N-Glycans

The ScGAL10 gene encoding UDP-galactose 4-epimerase was subcloned with NotI/PacI into the $NAT^R$ vectors pTA18 and pRCD351 in place of hGnTII, which inserts the epimerase gene in front of the strong PMA1 promoter and the weaker PpHIS3 promoter, respectively, to create plasmids pRCD331 ($P_{PMA1}$-ScGAL10) and pRCD352 ($P_{HIS3}$-ScGAL10), respectively. The plasmids were linearized (pRCD331 with SacI in the PpPMA1 promoter and pRCD352 with BglII in the PpHIS3 promoter) and transformed into strain PBP-3 (U.S. Pat. Appl. No. 20040018590). Strain PBP-3 is a mutant strain of *P. pastoris*, which has an och1 deletion and has been transformed with plasmids pSH49 and pPB104 which contain active fusion constructs of mouse Mannosidase IB and human GnTI, respectively as well as plasmid pPB103, which contains the *K. lactis* UDP-GlcNAc transporter and plasmid pBK64 which contains the reporter protein K3 (Choi et al.). This strain produces hybrid N-glycans of the structure $GlcNAcMan_5GlcNAc_2$ on secreted proteins. Resulting transformants selected on YPD medium containing Nourseothricin were analyzed by PCR with primers RCD285 (SEQ ID NO:43) (5'-TACGAGATTCCCAAATATGATTCC-3') and RCD286 (SEQ ID NO:44) (5'-ATAGTGTCTCCATATGGCTTGTTC-3') and by expressing the reporter protein K3 and analyzing the released N-glycans to ensure that the strains maintained the hybrid $GlcNAcMan_5GlcNAc_2$ glycan structure. One strain transformed with the pRCD352 ($P_{HIS3}$-ScGAL10) construct was designated RDP38-18. This strain was transformed with the plasmid pXB53 (containing the Mnn2(s)/hGalTI fusion construct and the $HYG^R$ and PpURA3 genes) after linearization with SalI (located in PpURA3). Transformants were selected on YPD medium with Hygromycin and screened by expressing K3 and determining the size of the N-glycans. A large portion (~⅔) of the N-glycans released from K3 purified from RDP39-6 strains (FIG. 10A) contained one additional hexose ($HexGlcNAcMan_5GlcNAc_2$) as compared with those from RDP38-18, which were mostly $GlcNAcMan_5GlcNAc_2$. Furthermore, the additional hexose residue could be removed by subsequent incubation with soluble β-1,4-galactosidase, but not α-1,3-galactosidase or α-1,2-mannosidase, indicating that the addition of a single galactose to the terminal GlcNAc with a specific linkage (β-1,4) was catalyzed by hGalTI in this strain.

Example 7

Expression of hGalTI and ScGAL10 in a Strain Producing Complex N-Glycans

The *P. pastoris* strain YSH-44 was constructed, which displays complex N-glycans with a $GlcNAc_2Man_3GlcNAc_2$ structure. YSH-44 is a mutant strain of *P. pastoris* deleted for och1 and transformed with plasmids pSH49, pPB104, pKD53, and pTC53 which contain active fusion constructs of mouse Mannosidase IB, human GnTI, *D. melanogaster* Mannosidase II, and human GnTII, respectively as well as plasmid pPB103, which contains the *K. lactis* UDP-GlcNAc transporter and plasmid pBK64 which contains the reporter protein K3 (Hamilton et al., Science. 2003 Aug. 29; 301(5637): 1244-6). This strain was transformed with the pXB53 plasmid containing a Mnn2(s)/hGalTI fusion construct and transformants were selected on YPD medium with hygromycin. Several transformants were analyzed by purifying K3 and analyzing the released N-glycans by MALDI-TOF MS. Each of the transformants analyzed yielded a majority of N-glycans with a $GlcNAc_2Man_3GlcNAc_2$ structure and a minority (~5%) consistent with a single hexose addition (YSH-71). However, although this peak always correlated with the introduction of hGalTI, it was completely recalcitrant to β-1,4-galactosidase. Subsequently, several of these strains were transformed with plasmids pRCD395 and pRCD396 (PpHIS3/$G418^R$ plasmids containing $P_{OCH1}$-ScGAL10 and $P_{SEC4}$-ScGAL10, respectively) after linearization with BglII, selected on G418, and the resulting strains were named YSH-83 and YSH-84, respectively. N-glycans released from secreted K3 were analyzed by MALDI-TOF MS. The resulting transformants were selected on YPD medium containing G418 and N-glycans released from purified, secreted K3 from these strains were analyzed by MALDI-TOF MS. A majority of N-glycans from these transformants were of three structures, $Gal_2GlcNAc_2Man_3GlcNAc_2$ (~0-25%) or $GalGlcNAc_2Man_3GlcNAc_2$ (~40-50%), with the rest of the N-glycans retaining the $GlcNAc_2Man_3GlcNAc_2$ structure displayed by the parental YSH-44 strain. The relative amount of N-glycans remained unchanged irrespective of whether the ScGAL10 epimerase gene was driven by the PpOCH1 promoter (YSH-83) or the PpSEC4 promoter (YSH-84). FIG. 9B shows a MALDI-TOF MS of the N-glycans released from YSH-84.

Example 8

Construction of a Epimerase/Transferase Fusion Construct

The SpGALE gene was amplified using primers RCD326 (SEQ ID NO:45) (5'-CTT

GGCGCGCCATGACTGGTGTTCATGAAGGGACT-3') and RCD329 (SEQ ID NO:46) 5'-CCT GGATCCCTTATATGTCTTGGTATGGGTCAG-3'), cloned into the pCR2.1 vector (Invitrogen) and sequenced. A truncated portion of the hGalTI gene eliminating the first 43 amino acid (hGalTIΔ43) was amplified using primers RCD328 (SEQ ID NO:47) (5'-CTTGGATCCGGTGGTG GCCGCGACCTGAGCCGCCTGCCC-3') and RCD199 (SEQ ID NO:48) (5'-CTTC TTAATTAACTAGCTCGGTGTCCCGATGTCCAC-3') cloned into the pCR2.1 vector (Invitrogen) and sequenced. The SpGALE clone was then digested with AscI/BamHI and the hGalTI clone digested with BamHI/PacI and both were inserted into pRCD452 digested with AscI/PacI. The plasmid pRCD452 contains the G418 resistance marker and GAPDH/CYC1 cassette with the ScMNN2(s)/hGalTI fusion. The AscI/BamHI SpGALE and BamHI/PacI hGalTIΔ43 fragments were ligated in place of the AscI/PacI released hGalTI to create pRCD461. This new plasmid, pRCD461 contains a ScMNN2(s)/SpGALE/hGalTI fusion where the SpGalE and hGalTI proteins are encoded in a single polypeptide separated by a four amino acid (GSGG) linker (SEQ ID NO: 68) containing the BamHI site, and driven by the PpGAPDH promoter.

Example 9

Expression of a Galactosyl Transferase, Epimerase and Transporter in a Strain Producing Complex N-Glycans Plasmids pXB53, containing the active hGalTI-53 gene fusion, and pRCD378, containing an hGalTII-53 fusion, were linearized with XhoI adjacent to the HYG$^R$ marker and blunted with T4 DNA polymerase (New England Biolabs, Beverly, Mass.). Plasmid pRCD381, containing a hGalTIII-53 gene fusion, was linearized with HindIII adjacent to the URA3 gene and blunted with T4 polymerase. The three epimerase genes ScGAL10, SpGALE and hGALE were then digested from plasmids pRCD404, pRCD406, and pRCD427, respectively, with XhoI/SphI, blunted with T4 DNA polymerase, and inserted into the three linearized transferase plasmids. This generated nine new double transferase/epimerase HYG$^R$ plasmids: pRCD424 with hGalTI-53 and ScGAL10, pRCD425 with hGalTI-53 and SpGALE, pRCD438 with hGalTI-53 and hGALE, pRCD439 with hGalTII-53 and ScGAL10, pRCD440 with hGalTII-53 and SpGALE, pRCD441 with hGalTII-53 and hGALE, pRCD442 with hGalTIII-53 and ScGAL10, pRCD443 with hGalTIII-53 and SpGALE, and pRCD447 with hGalTIII-53 and hGALE. Subsequently, the strain YSH44 was transformed sequentially with these double HYG$^R$ plasmids (linearized with XbaI) and the G418$^R$ plasmids pRCD393, pSH262, pSH263 and pSH264 containing the SpUGT, hUGT2, DmUGT, and hUGT1 UDP-Gal transporter encoding genes, respectively (linearized with AgeI). Thus, a series of strains was created that each contained a different combination of transferase, epimerase and transporter. First, the different UDP-Gal transporters were compared in strains that contained hGalTI-53 and SpGALE. The introduction of the DmUGT gene resulted in virtually all of the complex glycans having two terminal galactose residues ($Gal_2GlcNAc_2Man_3GlcNAc_2$), whereas the other three transporter genes resulted in a profile of complex glycans virtually identical to that obtained with only the transferase and epimerase (FIG. 11A-11E). Second, the epimerase genes were compared in strains with the hGalTI-53 fusion and active DmUGT gene by introducing pSH263 into strains with pRCD424, pRCD425 or pRCD438. The combinations of Gal genes with each of the three epimerase genes were equivalent in generating $Gal_2GlcNAc_2Man_3GlcNAc_2$ complex N-glycans on secreted K3. Finally, the three human transferase fusion constructs hGalTI-53, hGalTII-53, and hGalTIII-53 were compared in strains with DmUGT and SpGALE by introducing pRCD425, pRCD440 and pRCD443 into strains transformed with pSH263. Here, hGalTII-53 was slightly less efficient in transferring Gal as approximately 10% of the complex N-glycans in the strain with hGalTI-53 had only a single galactose (GalGlcNAc$_2$Man$_3$GlcNAc$_2$) where as all the observable complex N-glycans in the strain with hGalTI-53 were bi-galactosylated $Gal_2GlcNAc_2Man_3GlcNAc_2$ (FIG. 12A-12B). Moreover, hGalTIII-53, was significantly less efficient than either hGalTI-53 or hGalTII-53 as 60-70% of the complex N-glycans contained 0-1 galactose residues (GlcNAc$_2$Man$_3$GlcNAc$_2$ or GalGlcNAc$_2$Man$_3$GlcNAc$_2$) whereas only 30-40% were $Gal_2GlcNAc_2Man_3GlcNAc_2$ (FIG. 12A-12C).

Example 10

Expression of a Galactosyl Transferase, Epimerase and Transporter Using a Single Plasmid Construct The G418$^R$ plasmid containing P$_{OCH1}$-DmUGT, pSH263, was linearized by digesting with SacI, then blunted with T4 DNA polymerase (New England Biolabs). The P$_{SEC4}$-SpGALE gene was digested from plasmid pRCD405 with XhoI/SphI and blunted with T4 DNA polymerase. The blunt SpGALE was then inserted into the blunt SacI site of pSH263 to create plasmid pRCD446, which is a double transporter/epimerase G418$^R$ plasmid. pRCD446 was then linearized with EcoRI and blunted with T4 DNA polymerase. The P$_{GAPDH}$ScMNN2(s)/hGalTI fusion construct was released from pXB53 with BglII/BamHI and blunted with T4 DNA polymerase. The blunt ScMNN2(s)/hGalTI was then inserted into the blunt EcoRI site of pRCD446 to create plasmid pRCD465, which is a triple G418$^R$ plasmid containing ScMNN2(s)/hGalTI, SpGALE, and DmUGT. P. pastoris YSH-44, transformed with pRCD465 was designated RDP80. The N-glycan profile showed a single peak at 1663 m/z corresponding to the mass of $Gal_2GlcNAc_2Man_3GlcNAc_2$ [C] (FIG. 14A).

The HYG$^R$ plasmid containing hGalTI-53 and SpGALE, pRCD425, was linearized with AflII and blunted with T4 DNA polymerase. The DmUGT gene was released from pSH263 with NotI/PacI and inserted into plasmid pRCD405 digested with NotI/PacI to create plasmid pRCD468, which contains a P$_{SEC4}$-DmUGT-CYC1-TT fusion that can be released as a single cassette. pRCD468 was digested with XhoI/SalI to release the DmUGT cassette and blunted with T4 DNA polymerase. The blunted DmUGT was inserted into the blunt AflII site of pRCD425 to create plasmid pRCD466, which is a HYG$^R$ triple plasmid with hGalTI-53, SpGALE, and DmUGT.

The HYG$^R$ plasmid containing hGalTI-53 and hGALE pRCD438 was linearized with AflII and blunted with T4 DNA polymerase. pRCD468 was digested with XhoI/SalI to release the DmUGT cassette and blunted with T4 DNA polymerase. The blunted DmUGT was inserted into the blunt AflII site of pRCD438 to create plasmid pRCD467, which is a HYG$^R$ triple plasmid with hGalTI-53, hGALE, and DmUGT.

In Vitro β-Galactosidase Digest

N-glycans (2 μg) from P. pastoris strain RDP80 were incubated with 3 mU β1,4 galactosidase (QA bio, San Mateo, Calif.) in 50 mM $NH_4HCO_3$, pH6.0 at 37° C. for 16-20 hours. N-glycan analysis in FIG. 14B shows a predominant peak at 1430 m/z [A], which corresponds to the mass of the N-glycan $GlcNAc_2Man_3GlcNAc_2$, confirming galactose transfer in FIG. 14A.

In Vitro Sialyltransferase Reaction

K3 purified from strain RDP80 (200 µg) was incubated with 50 µg CMP-sialic acid and 15 mU rat recombinant α(2,6)-(N)-sialyltransferase (Calbiochem) in 50 mM $NH_4HCO_3$, pH6.0 at 37° C. for 16-20 hours. N-glycan were then released by PNGaseF digest and detected on MALDI-TOF MS. The spectrum of the glycans showed an increase in mass following sialyltransferase treatment (FIG. 14C) when compared with those from RDP80 (FIG. 14A). The spectrum as shown in FIG. 14C depicts a predominant peak at 2227 m/z [X], which corresponds to the mass of the N-glycan $NANA_2Gal_2GlcNAc_2Man_3GlcNAc_2$ further confirming that the N-glycans produced by strain RDP80 is human-type $Gal_2GlcNAc_2Man_3GlcNAc_2$.

Example 11

Epimerase Sequence Alignment

Sequence alignment of epimerases was performed using CLUSTAL. The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST (Basic Local Alignment Search Tool). (See, e.g., Altschul, S. F. (1993) J. Mol. Evol 36:290-300; and Altschul et al. (1990) J. Mol. Biol. 215:403-410.)

BLAST produced alignments of both nucleotide and amino acid sequences to determine sequence similarity. Other algorithms could have been used when dealing with primary sequence patterns and secondary structure gap penalties. (See, e.g., Smith, T. et al. (1992) Protein Engineering 5:35-51.)

Example 12

Materials

MOPS, sodium cacodylate, manganese chloride, UDP-galactose and CMP-N-acetylneuraminic acid were from Sigma. TFA was from Aldrich. β1,4-galactosyltransferase from bovine milk were from Calbiochem. Protein N-glycosidase F, mannosidases, and oligosaccharides were from Glyko (San Rafael, Calif.). DEAE ToyoPearl resin was from TosoHaas. Metal chelating "HisBind" resin was from Novagen (Madison, Wis.). 96-well lysate-clearing plates were from Promega (Madison, Wis.). Protein-binding 96-well plates were from Millipore (Bedford, Mass.). Salts and buffering agents were from Sigma (St. Louis, Mo.). MALDI matrices were from Aldrich (Milwaukee, Wis.).

Shake-Flask Cultivations

A single colony was picked from an YPD plate (<2 weeks old) containing the strain of interest and inoculated into 10 ml of BMGY media in a 50 ml "Falcon" centrifuge tube. The culture was grown to saturation at 24° C. (approx. 48 hours). The seed culture is transferred into a 500 ml baffled volumetric flask containing 150 ml of BMGY media and grown to $OD_{600}$ of 5±2 at 24° C. (approx. 18 hours). The growth rate of the cells was determined as the slope of a plot of the natural logarithm of $OD_{600}$ against time. The cells were harvested from the growth medium (BMGY) by centrifugation at 3000 g for 10 minutes, washed with BMMY and suspended in 15 ml of BMMY in a 250 ml baffled volumetric flask. After 24 hours, the expression medium flask is harvested by centrifugation (3000 g for 10 minutes) and the supernatant analyzed for K3 production.

Bioreactor Cultivations

A 500 ml baffled volumetric flask with 150 ml of BMGY media was inoculated with 1 ml of seed culture (see flask cultivations). The inoculum was grown to an $OD_{600}$ of 4-6 at 24° C. (approx 18 hours). The cells from the inoculum culture was then centrifuged and resuspended into 50 ml of fermentation media (per liter of media: $CaSO_4.2H_2O$ 0.30 g, $K_2SO_4$ 6.00 g, $MgSO_4.7H_2O$ 5.00 g, Glycerol 40.0 g, $PTM_1$ salts 2.0 ml, Biotin $4×10^{-3}$ g, $H_3PO_4$ (85%) 30 ml, PTM1 salts per liter: $CuSO_4.H_2O$ 6.00, NaI 0.08 g, $MnSO_4.7H_2O$ 3.00 g, $NaMoO_4.2H_2O$ 0.20 g, $H_3BO_3$ 0.02 g, $CoCl_2.6H_2O$ 0.50 g, $ZnCl_2$ 20.0 g, $FeSO_4.7H_2O$ 65.0 g, Biotin 0.20 g, $H_2SO_4$ (98%) 5.00 ml).

Fermentations were conducted in 3 liter dished bottom (1.5 liter initial charge volume) Applikon bioreactors. The fermentors were run in a fed-batch mode at a temperature of 24° C., and the pH was controlled at 4.5±0.1 using 30% ammonium hydroxide. The dissolved oxygen was maintained above 40% relative to saturation with air at 1 atm by adjusting agitation rate (450-900 rpm) and pure oxygen supply. The air flow rate was maintained at 1 vvm. When the initial glycerol (40 g/l) in the batch phase is depleted, which is indicated by an increase of DO, a 50% glycerol solution containing 12 ml/l of $PTM_1$ salts was fed at a feed rate of 12 ml/l/h until the desired biomass concentration was reached. After a half an hour starvation phase, the methanol feed (100% Methanol with 12 ml/l $PTM_1$) is initiated. The methanol feed rate is used to control the methanol concentration in the fermentor between 0.2 and 0.5%. The methanol concentration is measured online using a TGS gas sensor (TGS822 from Figaro Engineering Inc.) located in the offgass from the fermentor. The fermentors were sampled every eight hours and analyzed for biomass ($OD_{600}$, wet cell weight and cell counts), residual carbon source level (glycerol and methanol by HPLC using Aminex 87H) and extracellular protein content (by SDS page, and Bio-Rad protein assay).

Reporter protein expression, purification and release of N-linked glycans

The K3 domain, under the control of the alcohol oxidase 1 (AOX1) promoter, was used as a model protein and was purified using the 6× Histidine (SEQ ID NO: 71) tag as reported previously (Choi et al., Proc Natl Acad Sci USA. 2003 Apr. 29; 100(9):5022-7). The glycans were released and separated from the glycoproteins by a modification of a previously reported method (Papac and Briggs 1998). After the proteins were reduced and carboxymethylated, and the membranes blocked, the wells were washed three time with water. The protein was deglycosylated by the addition of 30 µl of 10 mM NH4HCO3 pH 8.3 containing one milliunit of N-glycanase (Glyko). After 16 hr at 37° C., the solution containing the glycans was removed by centrifugation and evaporated to dryness.

Protein Purification

Kringle 3 was purified using a 96-well format on a Beckman BioMek 2000 sample-handling robot (Beckman/Coulter Ranch Cucamonga, Calif.). Kringle 3 was purified from expression media using a C-terminal hexa-histidine tag. The robotic purification is an adaptation of the protocol provided by Novagen for their HisBind resin. Briefly, a 150 uL (μL) settled volume of resin is poured into the wells of a 96-well lysate-binding plate, washed with 3 volumes of water and charged with 5 volumes of 50 mM NiSO4 and washed with 3 volumes of binding buffer (5 mM imidazole, 0.5M NaCl, 20 mM Tris-HCL pH7.9). The protein expression media is diluted 3:2, media/PBS (60 mM PO$_4$, 16 mM KCl, 822 mM NaCl pH7.4) and loaded onto the columns. After draining, the columns are washed with 10 volumes of binding buffer and 6 volumes of wash buffer (30 mM imidazole, 0.5M NaCl, 20 mM Tris-HCl pH7.9) and the protein is eluted with 6 volumes of elution buffer (1M imidazole, 0.5M NaCl, 20 mM Tris-HCl pH7.9). The eluted glycoproteins are evaporated to dryness by lyophilyzation.

Release of N-Linked Glycans

The glycans are released and separated from the glycoproteins by a modification of a previously reported method (Papac, et al. A. J. S. (1998) Glycobiology 8, 445-454). The wells of a 96-well MultiScreen IP (Immobilon-P membrane) plate (Millipore) are wetted with 100 uL of methanol, washed with 3×150 uL of water and 50 uL of RCM buffer (8M urea, 360 mM Tris, 3.2 mM EDTA pH8.6), draining with gentle vacuum after each addition. The dried protein samples are dissolved in 30 uL of RCM buffer and transferred to the wells containing 10 uL of RCM buffer. The wells are drained and washed twice with RCM buffer. The proteins are reduced by addition of 60 uL of 0.1M DTT in RCM buffer for 1 hr at 37° C. The wells are washed three times with 300 uL of water and carboxymethylated by addition of 60 uL of 0.1M iodoacetic acid for 30 min in the dark at room temperature. The wells are again washed three times with water and the membranes blocked by the addition of 100 uL of 1% PVP 360 in water for 1 hr at room temperature. The wells are drained and washed three times with 300 uL of water and deglycosylated by the addition of 30 uL of 10 mM NH$_4$HCO$_3$ pH 8.3 containing one milliunit of N-glycanase (Glyko). After 16 hours at 37° C., the solution containing the glycans was removed by centrifugation and evaporated to dryness.

Miscellaneous: Proteins were separated by SDS/PAGE according to Laemmli (Laemmli 1970).

Matrix Assisted Laser Desorption Ionization Time of Flight Mass Spectrometry

Molecular weights of the glycans were determined using a Voyager DE PRO linear MALDI-TOF (Applied Biosciences) mass spectrometer using delayed extraction. The dried glycans from each well were dissolved in 15 uL of water and 0.5 uL spotted on stainless steel sample plates and mixed with 0.5 uL of S-DHB matrix (9 mg/mL of dihydroxybenzoic acid, 1 mg/mL of 5-methoxysalicilic acid in 1:1 water/acetonitrile 0.1% TFA) and allowed to dry.

Ions were generated by irradiation with a pulsed nitrogen laser (337 nm) with a 4 ns pulse time. The instrument was operated in the delayed extraction mode with a 125 ns delay and an accelerating voltage of 20 kV. The grid voltage was 93.00%, guide wire voltage was 0.10%, the internal pressure was less than 5×10-7 torr, and the low mass gate was 875 Da. Spectra were generated from the sum of 100-200 laser pulses and acquired with a 2 GHz digitizer. Man$_5$GlcNAc$_2$ oligosaccharide was used as an external molecular weight standard. All spectra were generated with the instrument in the positive ion mode. The estimated mass accuracy of the spectra was 0.5%.

What is claimed is:

1. A recombinant yeast or filamentous fungus host cell producing recombinant glycoproteins, the host cell genetically engineered to produce N-linked oligosaccharides having terminal GlcNAc residues and comprising a nucleic acid encoding a fusion protein that in the host cell transfers a galactose residue from UDP-galactose onto a terminal GlcNAc residue of an N-linked oligosaccharide branch of an N-glycan of a glycoprotein, wherein the N-linked oligosaccharide branch is selected from the group consisting of GlcNAcβ1,2-Manα1; GlcNAcβ1,4-Manα1,3, GlcNAcβ1,2-Manα1,6, GlcNAcβ1,4-Manα1,6 and GlcNAcβ1,6-Manα1,6, wherein the host cell is diminished or depleted in dolichyl-P-Man:Man5GlcNAc2-PP-dolichyl alpha-1,3 mannosyltransferase activity, and wherein the host cell produces a glycoprotein having one or more galactose residues.

2. The host cell of claim 1, wherein the host cell is a yeast.

3. The host cell of claim 1, wherein the host cell is a methylotrophic yeast.

4. The host cell of claim 1, wherein the host cell is selected from the group consisting of *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia sp., Saccharomyces cerevisiae, Saccharomyces sp., Hansenula polymorpha, Kluyveromyces sp., Kluyveromyces lactis, Candida albicans, Aspergillus nidulans, Aspergillus niger, Aspergillus oryzae, Trichoderma reesei, Chrysosporium lucknowense, Fusarium sp., Fusarium gramineum, Fusarium venenatum,* and *Neurospora crassa.*

5. The host cell of claim 1, wherein the host cell is *Pichia pastoris.*

6. The host of claim 1, wherein the host cell is impaired in initiating α1,6 mannosyltransferase activity with respect to the glycan on the glycoprotein.

7. The host cell of claim 1, wherein the host cell further expresses one or more N-acetylglucosamine transferase (GnT) activities selected from the group consisting of GnTII, GnTIII, GnTIV, GnTV, GnTVI and GnTIX.

8. The host cell of claim 1, wherein the host cell further expresses a GnT II activity.

9. The host cell of claim 1, wherein the host cell produces a glycoprotein selected from the group consisting of: GalGlcNAcMan3GlcNAc2, GalGlcNAc2Man3GlcNAc2, Gal2GlcNAc2Man3GlcNAc2, GalGlcNAc3Man3GlcNAc2, Gal2GlcNAc3Man3GlcNAc2, Gal3GlcNAc3Man3GlcNAc2, GalGlcNAc4Man3GlcNAc2, Gal2GlcNAc4Man3GlcNAc2, Gal3GlcNAc4Man3GlcNAc2, Gal4GlcNAc4Man3GlcNAc2 GalGlcNAcMan5GlcNAc2, GalGlcNAc2Man5GlcNAc2, Gal2GlcNAc2Man5GlcNAc2, GalGlcNAc3Man5GlcNAc2, Gal2GlcNAc3Man5GlcNAc2 and Gal3GlcNAc3Man5GlcNAc2.

10. A recombinant yeast or filamentous fungus host cell producing recombinant glycoproteins, the host cell genetically engineered to produce N-linked oligosaccharides having terminal GlcNAc residues and comprising a nucleic acid encoding a fusion protein that in the host cell transfers a galactose residue from UDP-galactose onto a terminal GlcNAc residue of an N-linked oligosaccharide branch of an N-glycan of a glycoprotein, wherein the N-linked oligosaccharide branch is selected from the group consisting of GlcNAcβ1,2-Manα1,3, GlcNAcβ1,4-Manα1,3, GlcNAcβ1,2-Manα1,6, GlcNAcβ1,4-Manα1,6 and GlcNAcβ1,6-Manα1,6, wherein the fusion protein consists of a catalytic domain of a galactosyltransferase (GalT) and a targeting peptide that targets the fusion protein to the endoplasmic reticulum (ER) or Golgi of the host cell, and wherein the host cell produces a glycoprotein having one or more galactose residues.

11. The host cell of claim 10, wherein the host cell is a yeast.

12. The host cell of claim 10, wherein the host cell is a methylotrophic yeast.

13. The host cell of claim 10, wherein the host cell is selected from the group consisting of *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia sp., Saccharomyces cerevisiae, Saccharomyces sp., Hansenula polymorphs, Kluyveromyces sp., Kluyveromyces lactis, Candida albicans, Aspergillus nidulans, Aspergillus niger, Aspergillus oryzae, Trichoderma reesei, Chrysosporium lucknowense, Fusarium sp., Fusarium gramineum, Fusarium venenatum, Physcomitrclla patens* and *Neurospora crassa.*

14. The host cell of claim 10, wherein the host cell is *Pichia pastoris.*

15. The host of claim 10, wherein the host cell is impaired in initiating α-1,6 mannosyltransferase activity with respect to the glycan on the glycoprotein.

16. The host cell of claim 10, wherein the host cell further expresses one or more N-acetylglucosamine transferase (GnT) activities selected from the group consisting of GnTII, GnTIII, GnTIV, GnTV, GnTVI and GnTIX.

17. The host cell of claim 10, wherein the host cell further expresses a GnT II activity.

18. The host cell of claim 10, wherein the host cell produces a glycoprotein selected from the group consisting of: GalGlcNAcMan3GlcNAc2, GalGlcNAc2Man3GlcNAc2, Gal2GlcNAc2Man3GlcNAc2, GalGlcNAc3Man3GlcNAc2, Gal2GlcNAc3Man3GlcNAc2, Gal3GlcNAc3Man3GlcNAc2, GalGlcNAc4Man3GlcNAc2, Gal2GlcNAc4Man3GlcNAc2, Gal3GlcNAc4Man3GlcNAc2, Gal4GlcNAc4Man3GlcNAc2 GalGlcNAcMan5GlcNAc2, GalGlcNAc2Man5GlcNAc2, Gal2GlcNAc2Man5GlcNAc2, GalGlcNAc3Man5GlcNAc2, Gal2GlcNAc3Man5GlcNAc2 and Gal3GlcNAc3Man5GlcNAc2.

19. A recombinant yeast or filamentous fungus host cell producing recombinant glycoproteins, the host cell genetically engineered to produce N-linked oligosaccharides having terminal GlcNAc residues and comprising a nucleic acid encoding a fusion protein that in the host cell transfers a galactose residue from UDP-galactose onto a terminal GlcNAc residue of an N-linked oligosaccharide branch of an N-glycan of a glycoprotein, wherein the N-linked oligosaccharide branch is selected from the group consisting of GlcNAcβ1,2-Manα1,3, GlcNAcβ1,4-Manα1,3, GlcNAcβ1,2-Manα1,6, GlcNAcβ1,4-Manα1,6 and GlcNAcβ1,6-Manα1,6, wherein the fusion consists of comprises a UDP-galactose 4-epimerase catalytic domain and a β1,4-galactosyltransferase (β1,4-GalTI) catalytic domain activity and a targeting peptide that targets the fusion protein to the endoplasmic reticulum (ER) or Golgi of the host cell, and wherein the host cell produces a glycoprotein having one or more galactose residues.

20. The host cell of claim 19, wherein the host cell is a yeast.

21. The host cell of claim 19, wherein the host cell is a methylotrophic yeast.

22. The host cell of claim 19, wherein the host cell is selected from the group consisting of *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorphs, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum,* and *Neurospora crassa.*

23. The host cell of claim 19, wherein the host cell is *Pichia pastoris.*

24. The host of claim 19, wherein the host cell is impaired in initiating α-1,6 mannosyltransferase activity with respect to the glycan on the glycoprotein.

25. The host cell of claim 19, wherein the host cell further expresses one or more N-acetylglucosamine transferase (GnT) activities selected from the group consisting of GnTII, GnTIII, GnTIV, GnTV, GnTVI and GnTIX.

26. The host cell of claim 19, wherein the host cell further expresses a GnT II activity.

27. The host cell of claim 19, wherein the host cell produces a glycoprotein selected from the group consisting of: GalGlcNAcMan3GlcNAc2, GalGlcNAc2Man3GlcNAc2, Gal2GlcNAc2Man3GlcNAc2, GalGlcNAc3Man3GlcNAc2, Gal2GlcNAc3Man3GlcNAc2, Gal3GlcNAc3Man3GlcNAc2, GalGlcNAc4Man3GlcNAc2, Gal2GlcNAc4Man3GlcNAc2, Gal3GlcNAc4Man3GlcNAc2, Gal4GlcNAc4Man3GlcNAc2 GalGlcNAcMan5GlcNAc2, GalGlcNAc2Man5GlcNAc2, Gal2GlcNAc2Man5GlcNAc2, GalGlcNAc3Man5GlcNAc2, Gal2GlcNAc3Man5GlcNAc2 and Gal3GlcNAc3Man5GlcNAc2.

28. A recombinant yeast or filamentous fungus host cell genetically engineered to be diminished or depleted in a dolichyl-P-Man:Man5GlcNAc2-PP-dolichyl alpha-1,3 mannosyltransferase activity and comprising an α-1,2 mannosidase activity, N-acetylglucosamine transferase I (GnT I) activity, and a β-galactosyltransferase activity, wherein the host cell is capable of producing glycoproteins comprising recombinant N-glycans that have one or more galactose residues.

29. The host cell of claim 28, wherein the host cell further expresses one or more N-acetylglucosamine transferase (GnT) activities selected from the group consisting of GnTII, GnTIII, GnTIV, GnTV, GnTVI and GnTIX.

30. The host cell of claim 28, wherein the host cell further expresses a GnT II activity.

31. The host cell of claim 28, wherein the host cell is a yeast.

32. The host cell of claim 28, wherein the host cell is a methylotrophic yeast.

33. The host cell of claim 28, wherein the host cell is a *Pichia pastoris.*

34. The host of claim 28, wherein said host cell is impaired in initiating α-1,6 mannosyltransferase activity with respect to the glycan on the glycoprotein.

35. The host cell of claim 28, wherein the host cell is selected from the group consisting of *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum,* and *Neurospora crassa.*

36. The host cell of claim 28, wherein the host cell is capable of producing a glycoprotein selected from the group consisting of: GalGlcNAcMan3GlcNAc2, GalGlcNAc2Man3GlcNAc2, Gal2GlcNAc2Man3GlcNAc2, GalGlcNAc3Man3GlcNAc2, Gal2GlcNAc3Man3GlcNAc2, Gal3GlcNAc3Man3GlcNAc2, GalGlcNAc4Man3GlcNAc2, Gal2GlcNAc4Man3GlcNAc2, Gal3GlcNAc4Man3GlcNAc2, Gal4GlcNAc4Man3GlcNAc2 GalGlcNAcMan5GlcNAc2, GalGlcNAc2Man5GlcNAc2, Gal2GlcNAc2Man5GlcNAc2, GalGlcNAc3Man5GlcNAc2, Gal2GlcNAc3Man5GlcNAc2 and Gal3GlcNAc3Man5GlcNAc2.

\* \* \* \* \*